US011398305B2

(12) United States Patent
Girardeau et al.

(10) Patent No.: US 11,398,305 B2
(45) Date of Patent: Jul. 26, 2022

(54) PATIENT REQUEST SYSTEM AND METHOD

(71) Applicant: Hill-Rom Services, Inc., Batesville, IN (US)

(72) Inventors: David M. Girardeau, Pittsboro, IN (US); Kiana M. Dezelon, Batesville, IN (US); Patrice Etchison, Cary, NC (US); Whitney C. Bergman, Raleigh, NC (US); Sherrod L. Faulks, Durham, NC (US)

(73) Assignee: Hill-Rom Services, Inc., Batesville, IN (US)

( * ) Notice: Subject to any disclaimer, the term of this patent is extended or adjusted under 35 U.S.C. 154(b) by 0 days.

(21) Appl. No.: 16/857,291

(22) Filed: Apr. 24, 2020

(65) Prior Publication Data
US 2020/0365264 A1 Nov. 19, 2020

Related U.S. Application Data

(60) Provisional application No. 62/914,753, filed on Oct. 14, 2019, provisional application No. 62/846,828, filed on May 13, 2019.

(51) Int. Cl.
| G16H 40/63 | (2018.01) |
| G16H 40/20 | (2018.01) |
| G16H 80/00 | (2018.01) |
| G06F 3/0482 | (2013.01) |
| G06F 3/16 | (2006.01) |

(52) U.S. Cl.
CPC ........... *G16H 40/63* (2018.01); *G06F 3/0482* (2013.01); *G06F 3/167* (2013.01); *G16H 40/20* (2018.01); *G16H 80/00* (2018.01)

(58) Field of Classification Search
CPC ........ G16H 40/63; G16H 40/20; G16H 80/00; G16H 40/67; G06F 3/0482; G06F 3/167; G06F 3/04817; G06F 16/9577; H04W 4/029; H04W 4/33
See application file for complete search history.

(56) References Cited

U.S. PATENT DOCUMENTS

| 5,592,153 A | 1/1997 | Welling et al. |
| 5,838,223 A | 11/1998 | Gallant et al. |
| 5,867,821 A | 2/1999 | Ballantyne et al. |

(Continued)

OTHER PUBLICATIONS

Screen captures from YouTube video clip entitled Starling Bedside Communication Demonstration, 16 pages.†

(Continued)

*Primary Examiner* — Pei Yong Weng
(74) *Attorney, Agent, or Firm* — Barnes & Thornburg LLP

(57) ABSTRACT

A patient request system includes a tablet computer that configured for entry of patient requests. The tablet computer is configured to display a first menu corresponding to basic request categories for a patient. The tablet computer is configured to display a second menu that corresponds to specific patient requests falling under the basic request category selected by the patient using the first menu. A server is configured to receive a specific patient request made by the patient. A notification device is configured to display the specific patient request to a caregiver. A patient request method is also disclosed.

20 Claims, 45 Drawing Sheets

(56) References Cited

U.S. PATENT DOCUMENTS

| | | | |
|---|---|---|---|
| 5,877,675 A | 3/1999 | Rebstock et al. |
| 6,998,978 B2 | 2/2006 | Kirkeby |
| 7,154,397 B2 | 12/2006 | Zerhusen et al. |
| 7,263,669 B2 | 8/2007 | Denholm |
| 7,769,598 B2 | 8/2010 | Denholm |
| 7,904,312 B2 | 3/2011 | Denholm |
| 8,183,987 B2 | 5/2012 | Traughber et al. |
| 8,591,411 B2 | 11/2013 | Banet et al. |
| 8,607,388 B1 | 12/2013 | Flanagan et al. |
| 8,612,248 B2 | 12/2013 | Denholm |
| 8,727,977 B2 | 5/2014 | Banet et al. |
| 9,230,421 B2 | 1/2016 | Reeder et al. |
| 9,361,769 B2 | 6/2016 | Traughber et al. |
| 9,489,466 B2 | 11/2016 | Costantino et al. |
| 9,492,341 B2 | 11/2016 | Huster et al. |
| 9,519,724 B2 | 12/2016 | Costantino et al. |
| 9,861,321 B2 | 1/2018 | Collins, Jr. et al. |
| 9,922,168 B2 | 3/2018 | Taughber et al. |
| 9,996,789 B2 | 6/2018 | Costantino et al. |
| 10,068,461 B2 | 9/2018 | Wildman et al. |
| 10,083,391 B2 | 9/2018 | Costantino et al. |
| 10,176,297 B2 | 1/2019 | Zerhusen et al. |
| 10,213,159 B2 | 2/2019 | Moon et al. |
| 10,278,645 B2 | 5/2019 | Moon |
| 10,290,071 B2 | 5/2019 | Heil et al. |
| 10,474,808 B2 | 11/2019 | Huster |
| 10,658,081 B2 | 5/2020 | Taughber et al. |
| 2006/0049936 A1 | 3/2006 | Collins, Jr. et al. |
| 2007/0061266 A1* | 3/2007 | Moore .............. G06Q 50/00 705/51 |
| 2008/0168267 A1* | 7/2008 | Bolen .............. H04M 1/72457 713/100 |
| 2008/0288279 A1 | 11/2008 | Henley et al. |
| 2011/0112866 A1 | 5/2011 | Gerrans |
| 2011/0224498 A1 | 9/2011 | Banet et al. |
| 2011/0224499 A1 | 9/2011 | Banet et al. |
| 2011/0224500 A1 | 9/2011 | Banet et al. |
| 2011/0224556 A1 | 9/2011 | Moon et al. |
| 2011/0224564 A1 | 9/2011 | Moon et al. |
| 2011/0246231 A1 | 10/2011 | Sie et al. |
| 2012/0166222 A1 | 6/2012 | Howard et al. |
| 2012/0169467 A1 | 7/2012 | Condra |
| 2012/0278104 A1* | 11/2012 | Traughber .......... G08B 25/016 705/3 |
| 2012/0323592 A1 | 12/2012 | Bechtel et al. |
| 2013/0179920 A1* | 7/2013 | Esaka ............... H04N 21/4821 725/39 |
| 2015/0012287 A1 | 1/2015 | Vucovich et al. |
| 2016/0027289 A1 | 1/2016 | Hargis |
| 2016/0104062 A1 | 4/2016 | Costantino et al. |
| 2016/0335686 A1 | 11/2016 | AthuluruTlrumala et al. |
| 2017/0124276 A1 | 5/2017 | Tee |
| 2017/0193186 A1 | 7/2017 | Tapadar et al. |
| 2017/0300931 A1 | 10/2017 | Gerrans |
| 2018/0005335 A1 | 1/2018 | Parente et al. |
| 2018/0158555 A1 | 6/2018 | Cashman et al. |
| 2018/0181719 A1 | 6/2018 | Balian |
| 2019/0108908 A1 | 4/2019 | Faulks |
| 2020/0118680 A1* | 4/2020 | Rao .................. G16H 40/40 |

OTHER PUBLICATIONS

Screen captures from YouTube video clip entitled PillowCase, 3 pages.†

Patient Experience, 11 pages.†

\* cited by examiner

† cited by third party

9:41 WED JUN 8 ...ııı 🛜 100% 🔋

TODAY

— 112

114 — GOOD MORNING, LIDA
7:00 AM
TUESDAY, JANUARY 10, 2019

116 — WEATHER NEAR YOU
67°F
PARTLY SUNNY

118 — GET STARTED WITH VOALTE PATIENT ENGAGEMENT    JUST NOW

VOALTE PATIENT ENGAGEMENT PUTS YOU IN CONTROL DURING YOUR HOSPITAL STAY. COMMUNICATE WITH YOUR CARE TEAM, VIEW EDUCATIONAL MATERIALS YOUR PROVIDER SHARES WITH YOU, AND MORE. TAP TO LEARN MORE.

130 — MAKE A REQUEST

122 — TODAY    124 — MY STAY    126 — MY REQUESTS    128 — LEARN

PATIENT REQUEST SYSTEM AND METHOD

The present application claims the benefit, under 35 U.S.C. § 119(e), of U.S. Provisional Application No. 62/846,828, filed May 13, 2019, and U.S. Provisional Application No. 62/914,753, filed Oct. 14, 2019, both of which are hereby incorporated by reference herein in their entirety.

BACKGROUND

The present disclosure relates to systems used by patients to make requests during their stays in healthcare facilities. More particularly, the present disclosure relates to systems and methods that enhance patient satisfaction and increase caregiver productivity.

Nurse call systems in which patients press a nurse call button on a handheld pillow speaker unit or on a hospital bed are known. In response to placing a nurse call, a caregiver responds to the patient to find out why the patient has placed the nurse call. Once the reason for the nurse call is known, the caregiver can take appropriate action to address the patient's request. Caregivers and patients would appreciate a system that permits patient requests to be made and addressed in a more efficient manner. Patients would also appreciate knowing a status of the requests they've placed with caregivers.

SUMMARY

A method, system or apparatus may comprise one or more of the features recited in the appended claims and/or the following features which, alone or in any combination, may comprise patentable subject matter:

According to a first aspect of the present disclosure, a patient request system may include a tablet computer that may be configured for entry of patient requests. The tablet computer may be configured to display a first menu that may correspond to basic request categories for a patient in response to selection of a make a request input on a predecessor screen of the tablet computer. The tablet computer may be configured to display a second menu that may correspond to specific patient requests that may fall under the basic request category selected by the patient using the first menu. A server may be configured to receive a specific patient request made by the patient. A notification device may be configured to display the specific patient request to a caregiver.

In some embodiments, the tablet computer may be configured to display a list of specific patient requests that may be made by the patient and a status of each specific patient request. Optionally, the tablet computer may be configured to display a list of caregivers that may be assigned to the patient. Further optionally, the tablet computer may be configured to display weather information that may be based on a periodically received weather feed.

In some embodiments, the basic categories that may be included in first menu may include one or more of the following options: I'm thirsty. I'm hungry, I feel, help me with, services, room, bring me, or mother/baby. In response to selection of the I'm thirsty option on the first menu, the specific patient requests appearing on the second menu may include one or more of the following options: water, ice, juice, ginger ale, cola, diet cola, clear soda, clear diet soda, nutritional drink, or other drink. In response to selection of the I'm hungry option on the first menu, the specific patient requests appearing on the second menu may include one or more of the following options: crackers, meal, Jell-O, other snack, or popsicle.

In response to selection of the I feel option on the first menu, the specific patient requests appearing on the second menu may include one or more of the following options: sick, pain, hot/cold, cold feet, can't sleep, or other need. In response to selection of the help me with option on the first menu, the specific patient requests appearing on the second menu may include one or more of the following options: get up/move, bandage problem, clothes/gown, blood sugar check, IV hurts, get a bath, bathroom, brush teeth, walk, collect bathroom specimen, or other problem. In response to selection of the services option on the first menu, the specific patient requests appearing on the second menu may include one or more of the following options: translator, chaplain/clergy, case manager/social worker, visitor information, or other service.

In response to selection of the room option on the first menu, the specific patient requests appearing on the second menu may include one or more of the following options: I can't reach, room hot/cold, TV/remote control issue, adjust bed, machine is beeping, noisy, lights on/off, sheet change, spill, or other environmental. In response to selection of the bring me option on the first menu, the specific patient requests appearing on the second menu may include one or more of the following options: pen/paper, ice pack, pillow, blanket, or other need. In response to selection of the mother/baby option on the first menu, the specific patient requests appearing on the second menu may include one or more of the following options: pacifier, baby to/from nursery/bassinet, baby care, swaddling, breastfeeding, breast pump, pad, bottle/formula, diaper, baby wipes, skin time/kangaroo care, baby blanket, other need mother, or other need baby.

In some embodiments, the patient request system may further include locating equipment that may be operable to determine a location of the tablet computer in a healthcare facility and the first menu may be altered based on the location. For example, if the tablet computer is determined to be located in a maternity ward, then a maternity option may be included in the first menu, and if the tablet computer is determined not to be located in the maternity ward, then the maternity option may be omitted from the first menu.

Optionally, after the patient makes the specific patient request using the tablet computer, the tablet computer may be operable to display a status of the specific patient request while the specific patient request may be pending. Further optionally, the status may include fields that are highlighted to indicate that the specific patient request has been submitted, that the specific patient request has been accepted by a caregiver, and that the specific patient request has been completed.

If desired, the tablet computer may be configured to permit the patient to make specific patient requests by voice. Alternatively or additionally, the tablet computer may be configured to permit the patient to make and receive phone calls and video calls. Further alternatively or additionally, the tablet computer may be configured to display each of the following: visitor hours, parking information, a cafeteria menu, hospital activities, and a TV channel list.

According to a second aspect of the present disclosure, a patient request method may include providing a tablet computer to a patient after configuring the tablet computer for entry of patient requests. The method also include displaying on the tablet computer a first menu that may correspond to basic request categories for a patient in response to selection of a make a request input on a predecessor screen of the tablet computer and receiving a selection on the tablet computer by the patient of one of the basic request categories. Still further, the method may include displaying on the tablet computer a second menu that may correspond to specific patient requests that may fall under the basic request category selected by the patient using the first menu. The method may further include receiving a selection on the tablet computer by the patient of one of the specific patient requests and transmitting the specific patient request selected by the patient to a server that may be configured to receive the specific patient request made by the patient.

In some embodiments, the method may further include displaying on the tablet computer a list of specific patient requests made by the patient and a status of each specific patient request. Alternatively or additionally, the method may further include displaying on the tablet computer a list of caregivers assigned to the patient. Further alternatively or additionally, the method may further include displaying on the tablet computer weather information that may be based on a periodically received weather feed.

Optionally, the basic categories that may be included in first menu may include one or more of the following options: I'm thirsty, I'm hungry, I feel, help me with, services, room, bring me, or mother/baby. The method may include, in response to selection of the I'm thirsty option on the first menu, displaying one or more of the following options as the second menu: water, ice, juice, ginger ale, cola, diet cola, clear soda, clear diet soda, nutritional drink, or other drink. The method may include, in response to selection of the I'm hungry option on the first menu, displaying one or more of the following options as the second menu: crackers, meal, Jell-O, other snack, or popsicle.

The method may include, in response to selection of the I feel option on the first menu, displaying one or more of the following options as the second menu: sick, pain, hot/cold, cold feet, can't sleep, or other need. The method may also include, in response to selection of the help me with option on the first menu, displaying one or more of the following options as the second menu: get up/move, bandage problem, clothes/gown, blood sugar check, IV hurts, get a bath, bathroom, brush teeth, walk, collect bathroom specimen, or other problem. The method may further include, in response to selection of the services option on the first menu, displaying one or more of the following options as the second menu: translator, chaplain/clergy, case manager/social worker, visitor information, or other service.

In some embodiments, the method may include, in response to selection of the room option on the first menu, displaying one or more of the following options as the second menu: I can't reach, room hot/cold, TV/remote control issue, adjust bed, machine is beeping, noisy, lights on/off, sheet change, spill, or other environmental. The method may also include, in response to selection of the bring me option on the first menu, displaying one or more of the following options as the second menu: pen/paper, ice pack, pillow, blanket, or other need. The method may further include, in response to selection of the mother/baby option on the first menu, displaying one or more of the following options as the second menu: pacifier, baby to/from nursery/bassinet, baby care, swaddling, breastfeeding, breast pump, pad, bottle/formula, diaper, baby wipes, skin time/kangaroo care, baby blanket, other need mother, or other need baby.

If desired, the method may include providing locating equipment that may be operable to determine a location of the tablet computer in a healthcare facility and altering the first menu based on the location. For example, if the tablet computer is determined to be located in a maternity ward, including a maternity option in the first menu may be part of the method, and if the tablet computer is determined not to be located in the maternity ward, then omitting the maternity option the first menu may be part of the method.

In some embodiments, the method may include, after the patient makes the specific patient request using the tablet computer, displaying on the tablet computer a status of the specific patient request while the specific patient request is pending. For example, the status may include fields that are highlighted to indicate that the specific patient request has been submitted, that the specific patient request has been accepted by a caregiver, and that the specific patient request has been completed.

Optionally, the method may include receiving at the tablet computer voice input from the patient to make specific patient requests. Alternatively or additionally, the tablet computer may be configured to permit the patient to make and receive phone calls and video calls. Further alternatively or additionally, the method may further include displaying on the tablet computer a third menu including each of the following: visitor hours, parking information, a cafeteria menu, hospital activities, and a TV channel list. If desired, the method may further include displaying on a notification device of at least one caregiver the specific patient request made by the patient.

Additional features, which alone or in combination with any other feature(s), such as those listed above and those listed in the claims, may comprise patentable subject matter and will become apparent to those skilled in the art upon consideration of the following detailed description of various embodiments exemplifying the best mode of carrying out the embodiments as presently perceived.

BRIEF DESCRIPTION OF THE DRAWINGS

The detailed description particularly refers to the accompanying figures, in which:

FIG. 11 is a screen shot of a first today screen that appears on the tablet once it has been successfully assigned to a patient;

FIG. 19 is a screen shot of a second make a request screen that has a set of four icons on a menu for making a request by the patient;

DETAILED DESCRIPTION

Figure 1:
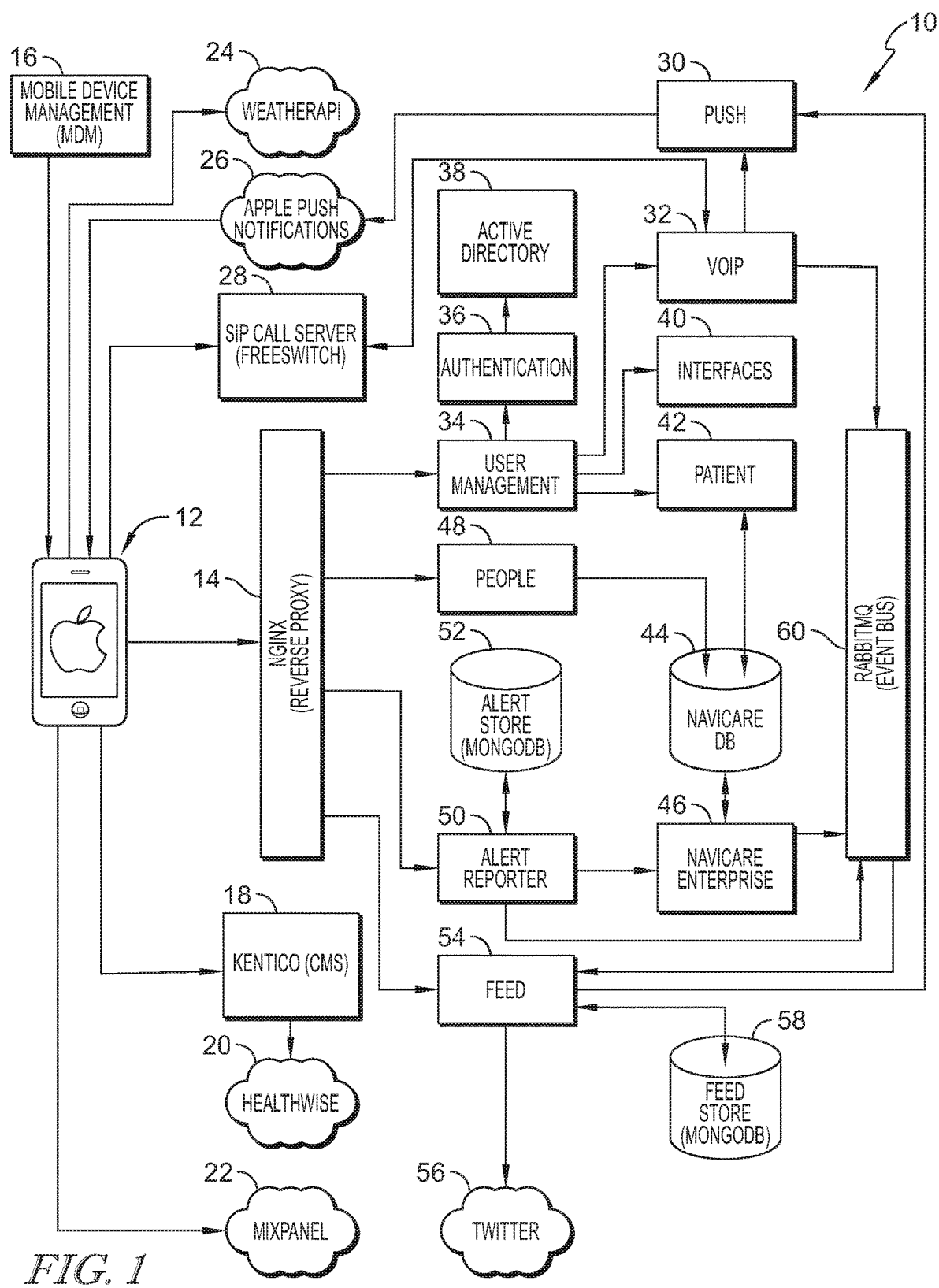
FIG. 1 is a block diagram of a patient request system showing a tablet that is used by a patient to send requests using a patient engagement software application.

A system 10 includes a tablet computer 12 coupled to a server 14 as shown in FIG. 1. Tablet computer 12 is provided by a healthcare facility to a patient during their stay at the healthcare facility. As discussed in further detail below, tablet computer 12 is configured with patient engagement software to permit the patient to make specific requests to caregivers. Server 14 manages the routing of patient requests to other computer devices of the system 10. In some embodiments, server 14 is a reverse proxy server available from NGINX of San Francisco, Calif. Although FIG. 1 shows a single tablet computer 12, system 10 includes a multitude of tablet computers 12 that are provided to the various patients at the healthcare facility. Thus, the description below of features of one tablet computer 12 is applicable to all of the tablet computers 12 of system 10 unless specifically noted otherwise. Tablet computer 12 is sometimes referred to herein as just tablet 12.

Tablet computer 12 is coupled to a mobile device management (MDM) system 16. MDM system 16 is a locally hosted system used to provide a reference version of the patient engagement software, which in some embodiments is an iOS application, along with configuration information for the operation of tablet computer 12 within the healthcare facility. The configuration information includes information pertaining to the server and port associated with the reverse proxy server 14 and the identifier of the patient. The identifier of the patient is used by a content management solution (CMS) 18 to determine a source of operational configuration for the tablet computer 12. In the illustrative example, the CMS 18 is a software solution available from Kentico Software, LLC of Bedford, N.H.

The CMS 18 operates to organize content on a patient-by-patient basis, including a HIPAA disclaimer presented to the patient at first login, visiting hours, dining menus, TV channel listings, educational content via HealthWise 20. HealthWise 20 is a cloud-based health content and education provider of text and video materials. During the course of care and treatment, patients have access to a library of material from HealthWise 20 to help the patient understand what to expect as part of the patient's care and recovery.

Tablet computer 12 is also coupled to MixPanel 22 which is a business analytics company located in San Francisco, Calif. MixPanel operates a cloud-based user behavior analysis application used to measure the value of features included within the patient engagement software of tablet computers 12. Data collected by MixPanel 22 is used to help develop plans to improve the usability of the patient engagement software. Tablet computer 12 is further in communication with Weather API 24 which is a cloud-based source of weather information including local temperature and conditions.

Tablet computer 12 is configured to receive Apple Push Notifications (APNS) 26. APNS 26 deliver asynchronous events to the patient engagement software of tablet computer 12. In some embodiments, APNS 26 are used to wake the patient engagement software as part of the initiation of voice communications over a SIP call server 28 which provides secure voice communications between a caregiver and a patient. System 10 includes various Service Fabric software modules available from Microsoft Azure of Seattle, Wash. For example, a push Service Fabric micro service module 30 is used to initiate APNS requests to tablet computer 12 and a VoIP Service Fabric micro service module 32 is used to allocate/deallocate SIP endpoints used by the patient engagement software of tablet computer 12. Module 32 is engaged by a VoIP call server to send APNS notifications to tablet computer 12 as part of the establishment of a voice call.

A user management Service Fabric micro service module 34 is coupled to server 14 and is used to establish a client session and gather initial data pertinent to an authenticated user. Internally, module 34 processes a login pipeline specific to a client application, to gather information to minimize the amount of time between login and useful client operation of tablet computer 12. Module 34 communicates with an authentication Service Fabric micro service module 36 which provides user authentication via an active directory 38 of the healthcare facility. The active directory 38 provides user authentication (username/password) for caregivers attempting to access the patient engagement software of tablet computer 12. The active directory 38 is used by the authentication service module 36 to verify that the credentials provided by the user are correct. The authentication service module 36 is also used by module 34 to obtain a session token used for interactions of the patient using tablet computer 12.

User management module 34 also communicates with VoIP module 32, an interfaces Service Fabric micro service module 40, and a patient Service Fabric micro service module 42. Module 40 is used by client applications to determine the set of available routes for patient requests. Routes included in the response collection are given a mnemonic identifier that a client uses to match a resource to its associated routes/URL's. Block 40 in FIG. 1 is representative of the various endpoint devices to which patient requests are transmitted and displayed. For example, block 40 represents mobile devices (e.g., smart phones, tablets, telephone handsets with graphical displays, etc.) assigned to, and carried by, caregivers in the healthcare facility. Block 40 also represents status boards, master nurse stations computers, administrator computers, and the like on which patient requests may be displayed at the discretion of the designer of system 10.

Module 42 is used to obtain patient details for presentation in the patient engagement software of tablet computer 12 after login. The patient details is obtained by module 42 from a nurse call system database 44. In the illustrative example, the nurse call system is the NAVICARE® nurse call system available from Hill-Rom Company, Inc. of Batesville, Ind. Database 44 also has information regarding staff, alerts, and organization of system 10. Database 44 is coupled to or included in a nurse call enterprise server 46. Database 44 also receives information from a people Service Fabric micro service module 48 which interfaces with server 14. Module 48 is used to determine the list of available patients for impersonation by a care team member during authentication.

Still referring to FIG. 1, an alert reporter Service Fabric micro service module 50 is coupled to nurse call server 46 and also interfaces with server 14. Module 50 facilitates integrating the healthcare enterprise (IHE) alert communication management (ACM) compliant alert reporting on behalf of the patient engagement software of tablet computer 12. The computer tablet 12 provides a patient care device PCD-04 compliant alert request via a representational state transfer (RESTful) application program interface (API) which is sent to the nurse call server 46 for further processing. Upon successful alert creation, the alert reported module 50 provides the client with an associated identifier which is used for matching against alert status changes. Module 50 is coupled to an alert store database 52 which in some embodiments is available from MongoDB, Inc. of New York, N.Y. Database 52 stores information about each of the alerts that are generated in system 10 by tablet computer 12 and is used for managing the lifecycle of each alert.

A feed Service Fabric micro service module 54 interfaces with server 14 and is used to relay an event stream to tablet computer 12. Module 54 listens for updates to staff care assignments, updates to alerts in the nurse call system, audio call events from staff to patients, while polling for changes from a Twitter feed 56 to provide news and information to the patient via tablet computer 12. Module 54 is coupled to a feed store database 58 which in some embodiments is available from MongoDB, Inc. of New York, N.Y. Database 58 stores information about each of the feeds that are generated in system 10. Module 54 is also coupled to module 30 for pushing events to the tablet computer 12 as APNS. Modules 32, 50, 54 and nurse call server 46 are coupled to an event bus 60 which in some embodiments comprises a RabbitMQ open source message broker available from Pivotal Software, Inc. of San Francisco, Calif.

Server 14 includes a Service Fabric guest application that manages the routing of patient RESTful requests over hypertext transfer protocol secure (HTTPS) to the associated Service Fabric micro service of modules 30, 32, 34, 36, 40, 42, 48, 50, 54. Some or all of modules 30, 32, 34, 36, 40, 42, 48, 50, 54 may be stored in server 14 or in other servers of system 10. Thus, modules 30, 32, 34, 36, 40, 42, 48, 50, 54 are software modules that are distributed within computer devices such as servers in some embodiments of system 10. Database 44 may be stored in server 46 in some embodiments, and database 52 may be stored in the same server in which module 50 is stored in some embodiments.

Figure 2:
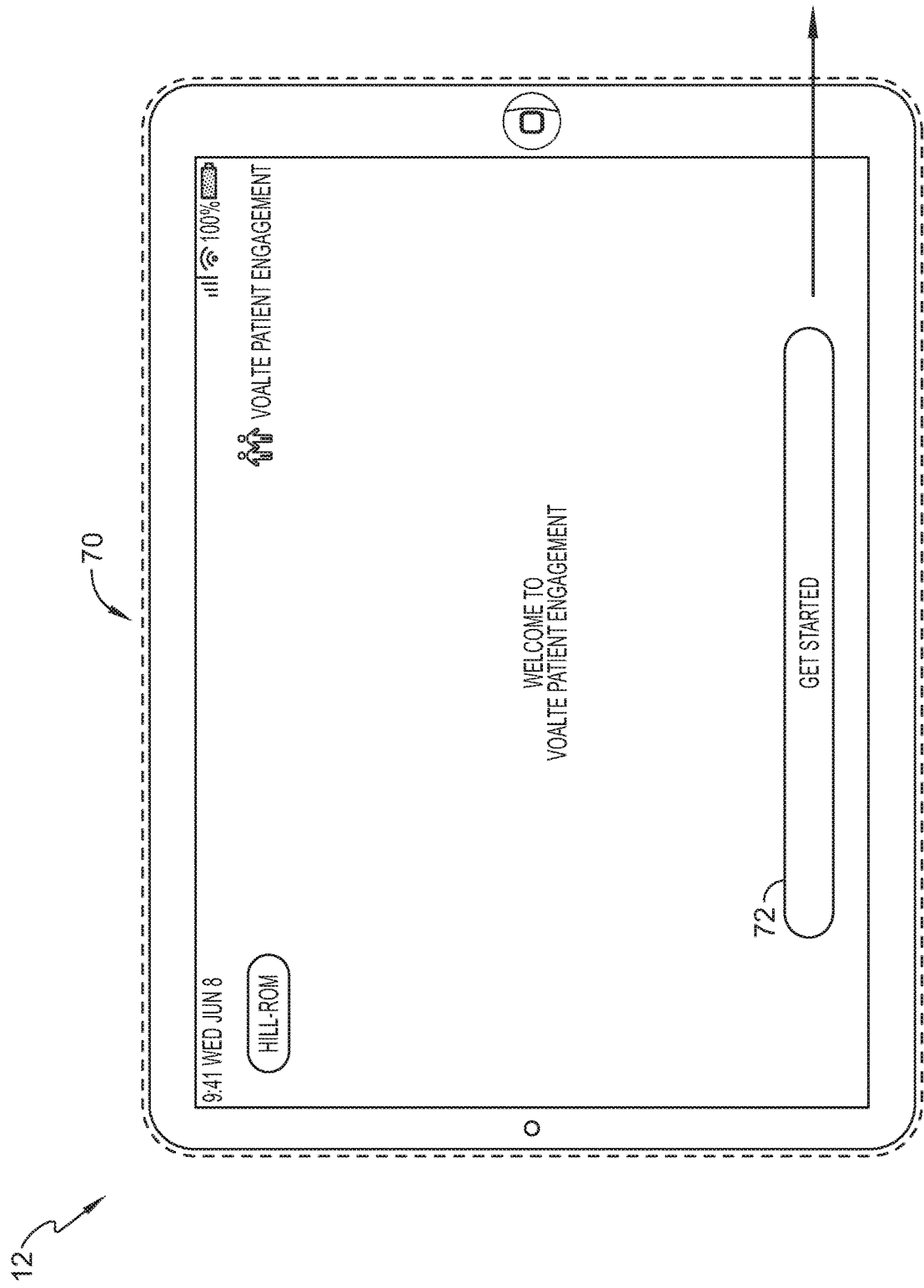
FIG. 2 is a screen shot of a first set up screen that is used by a caregiver to set up the tablet for use by a patient.
Figure 3:
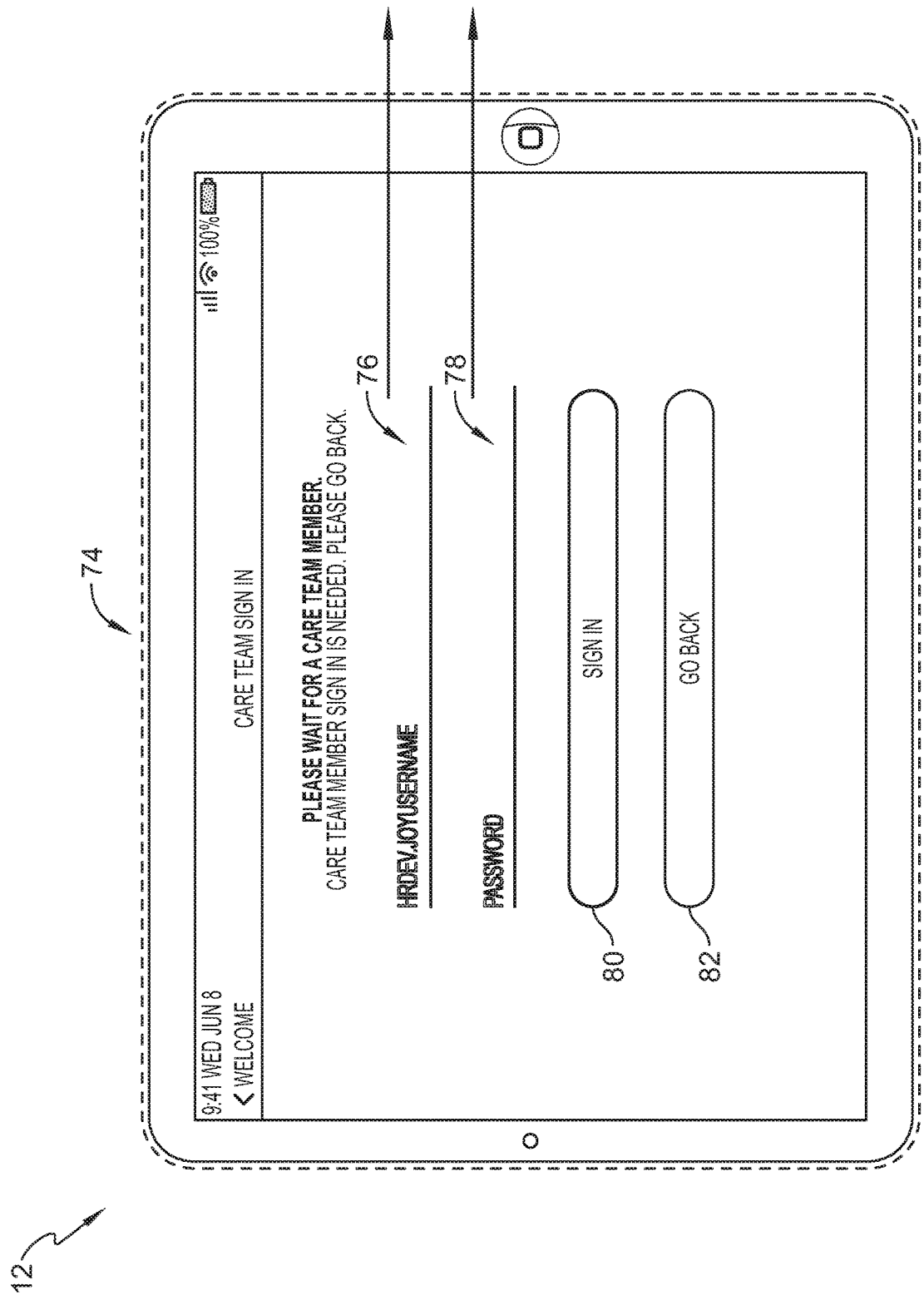
FIG. 3 is a screen shot of a first sign in screen that is used by the caregiver to sign in to the patient request system.
Figure 4:
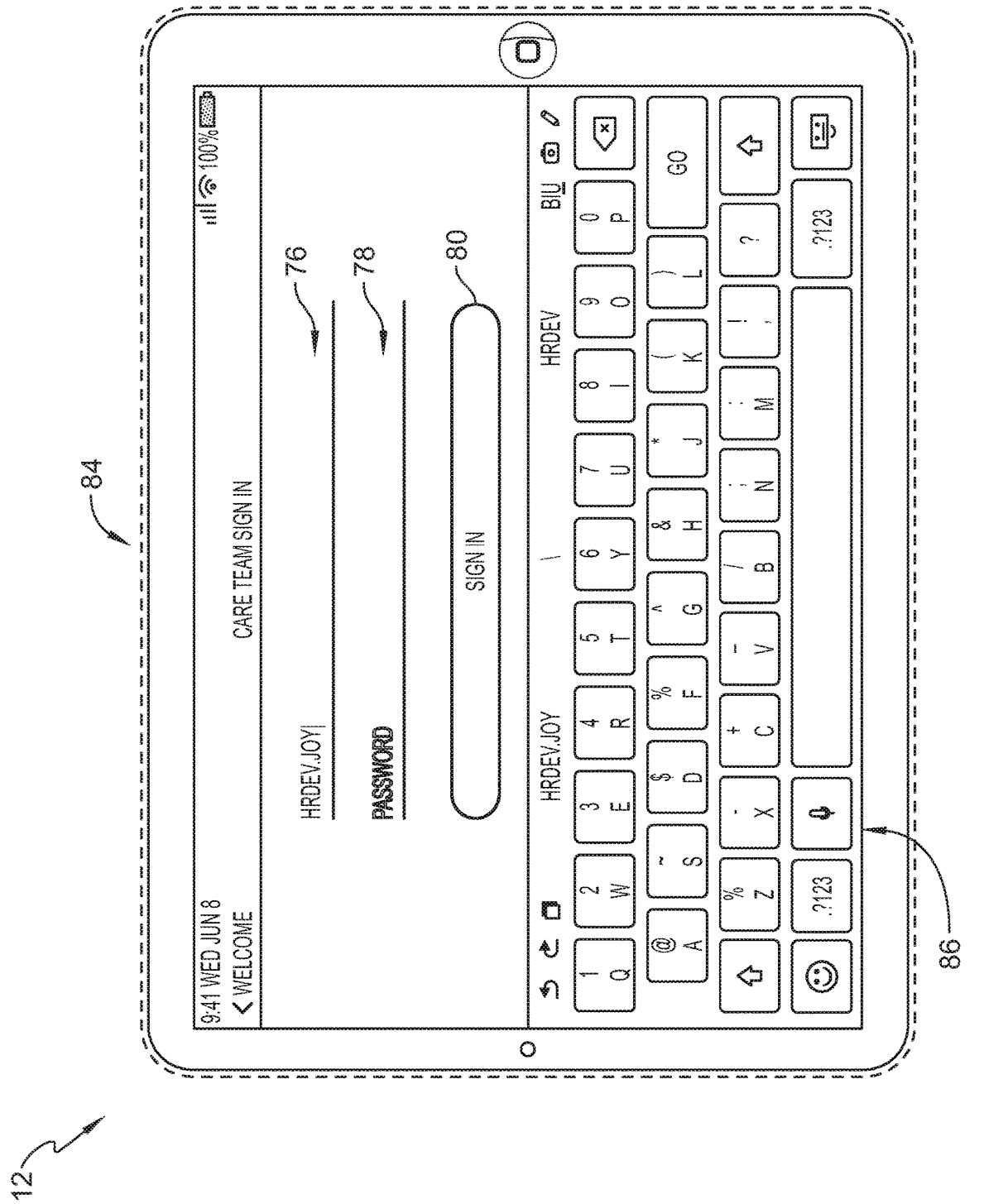
FIG. 4 is a screen shot of a second sign in screen that is used by the caregiver to sign in to the patient request system.

Referring now to FIG. 2, a first set up screen 70 appears on tablet computer 12 upon initial startup and is used by a caregiver to begin the process of setting up the tablet 12 for use by a patient. Screen 70 has a get started button 72 that, when selected by the caregiver, causes a first sign in screen 74, shown in FIG. 3, to appear on the tablet 12. Screen 74 includes a user name field 76 and a password field 78. Beneath fields 76, 78 are a sign in button 80 and a go back button 82. In response to the caregiver touching one of fields 76, 78, a second sign in screen 84 appears on tablet 12 as shown in FIG. 4. Screen 84 includes a keyboard 86 for use by the caregiver in entering the user name and password information in fields 76, 78, respectively. After fields 76, 78 are filled in, the caregiver selects the sign in button 80. If the caregiver does not wish to sign in, the caregiver can select the go back button on screen 74 to return to screen 70.

Figure 5:
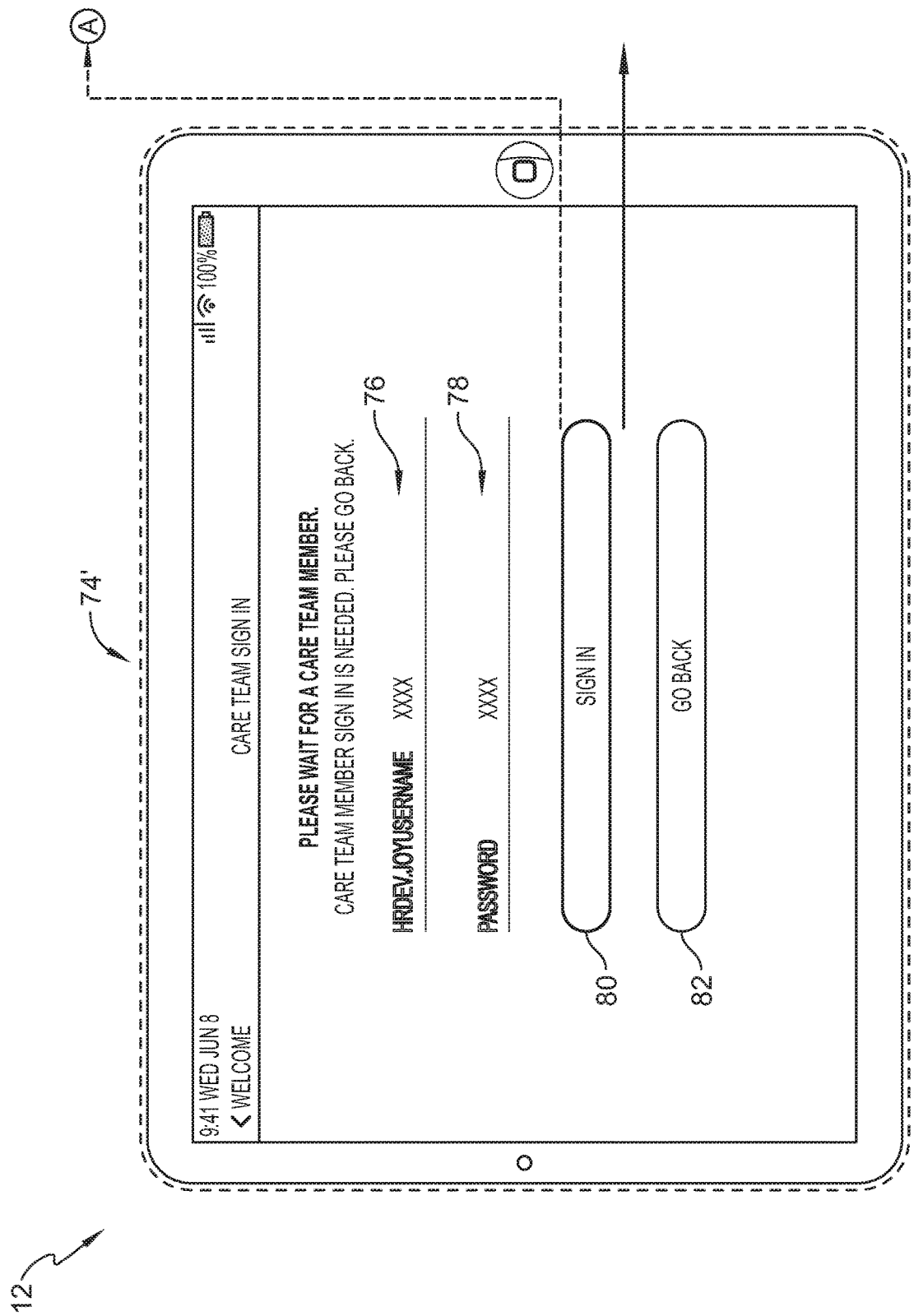
FIG. 5 is a screen shot of a third sign in screen that is used by the caregiver to sign in to the patient request system.
Figure 6:
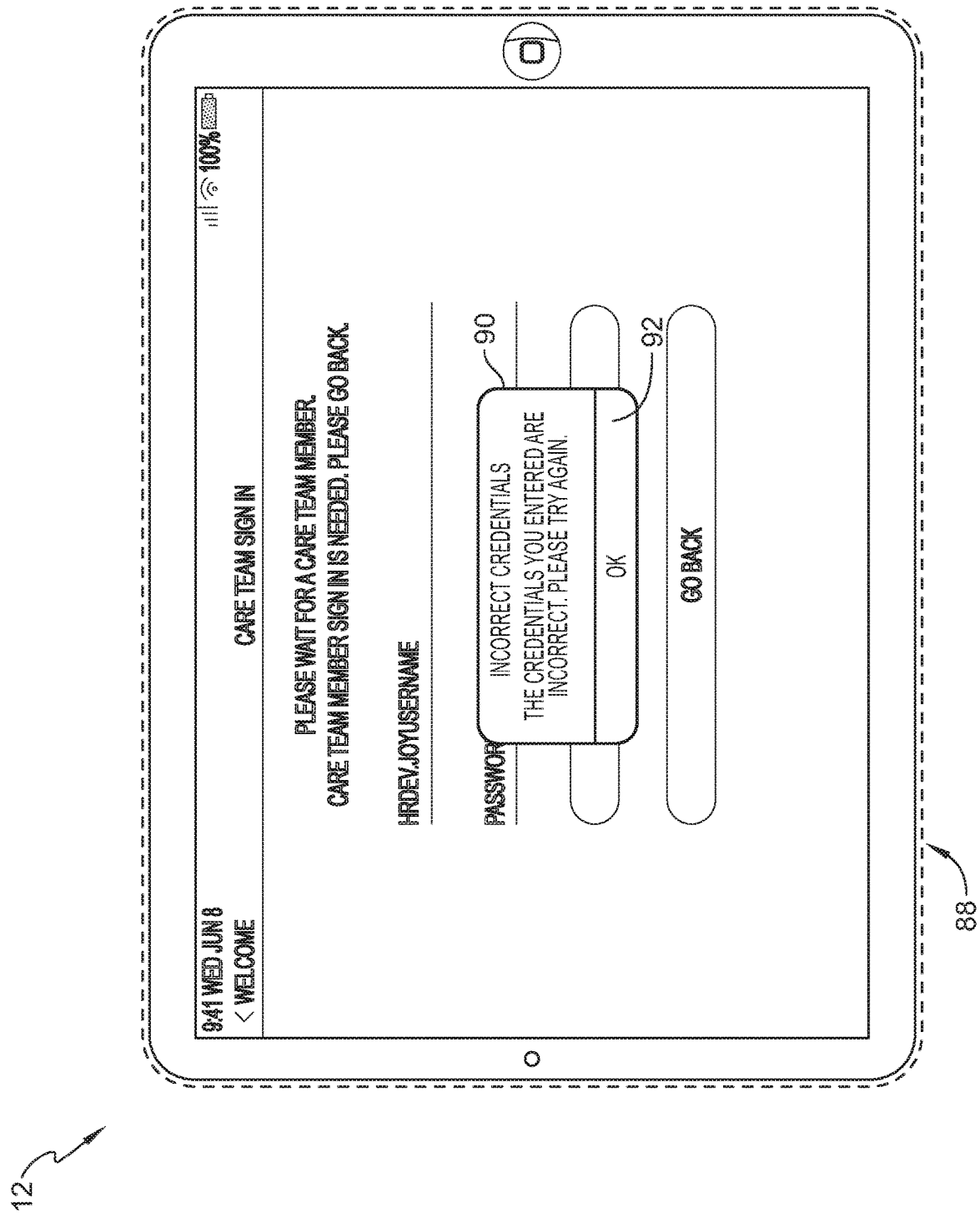
FIG. 6 is a screen shot of a sign in error alert screen that appears if incorrect credentials are entered by the caregiver when attempt to sign in to the patient request system.
Figure 7:
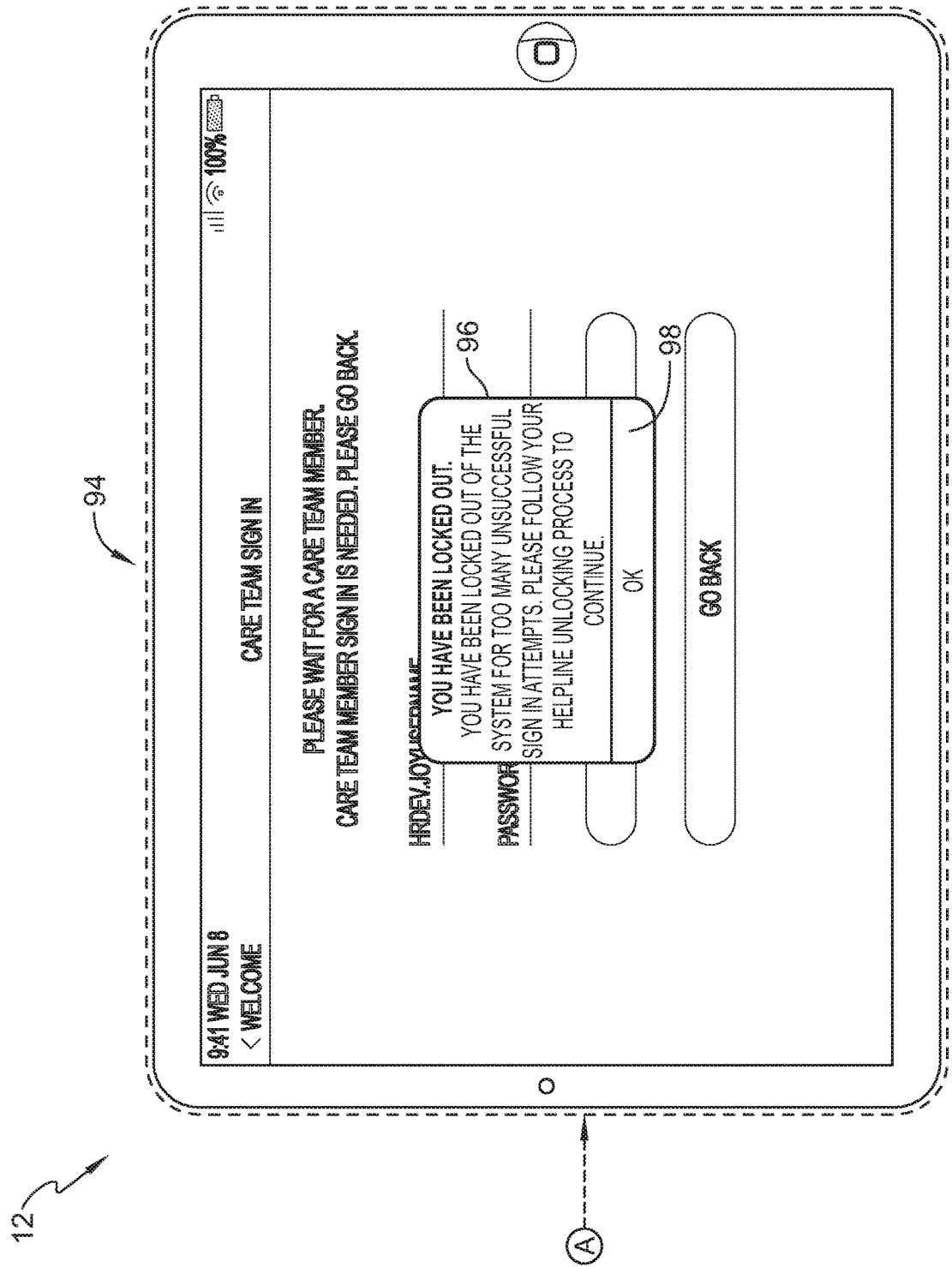
FIG. 7 is a screen shot of a lock out alert screen that appears if incorrect credential are entered multiple times by the caregiver when attempting to sign in to the patient request system.

If an incorrect user name is entered in field 76 or if an incorrect password is entered in field 78, as suggested in third sign in screen 74' of FIG. 5, then in response to selection of the sign in button 80, an error alert screen 88 appears on tablet 12 as shown in FIG. 6. Screen 88 includes a text box 90 which includes a message warning the caregiver that incorrect credentials have been entered and informing the caregiver to try again. An OK button 92 is provided at the bottom of box 90 for selection by the caregiver to return back to screen 74 to make another attempt at entering the proper user name and password credentials. If the caregiver enters incorrect credentials in one or both of fields 76, 78 too many times (e.g., two or three times), then in response to selection of the sign in button 80, a lock out alert screen 94 appears on the tablet 12 as shown in FIG. 7. Screen 94 includes a text box 96 that advises the caregiver that they have been locked out from tablet 12 and that the caregiver needs to follow the healthcare facilities lock out process to continue. An OK button 98 is provided at the bottom of box 94 and is selected by the caregiver to acknowledge the lock out alert.

Figure 8:
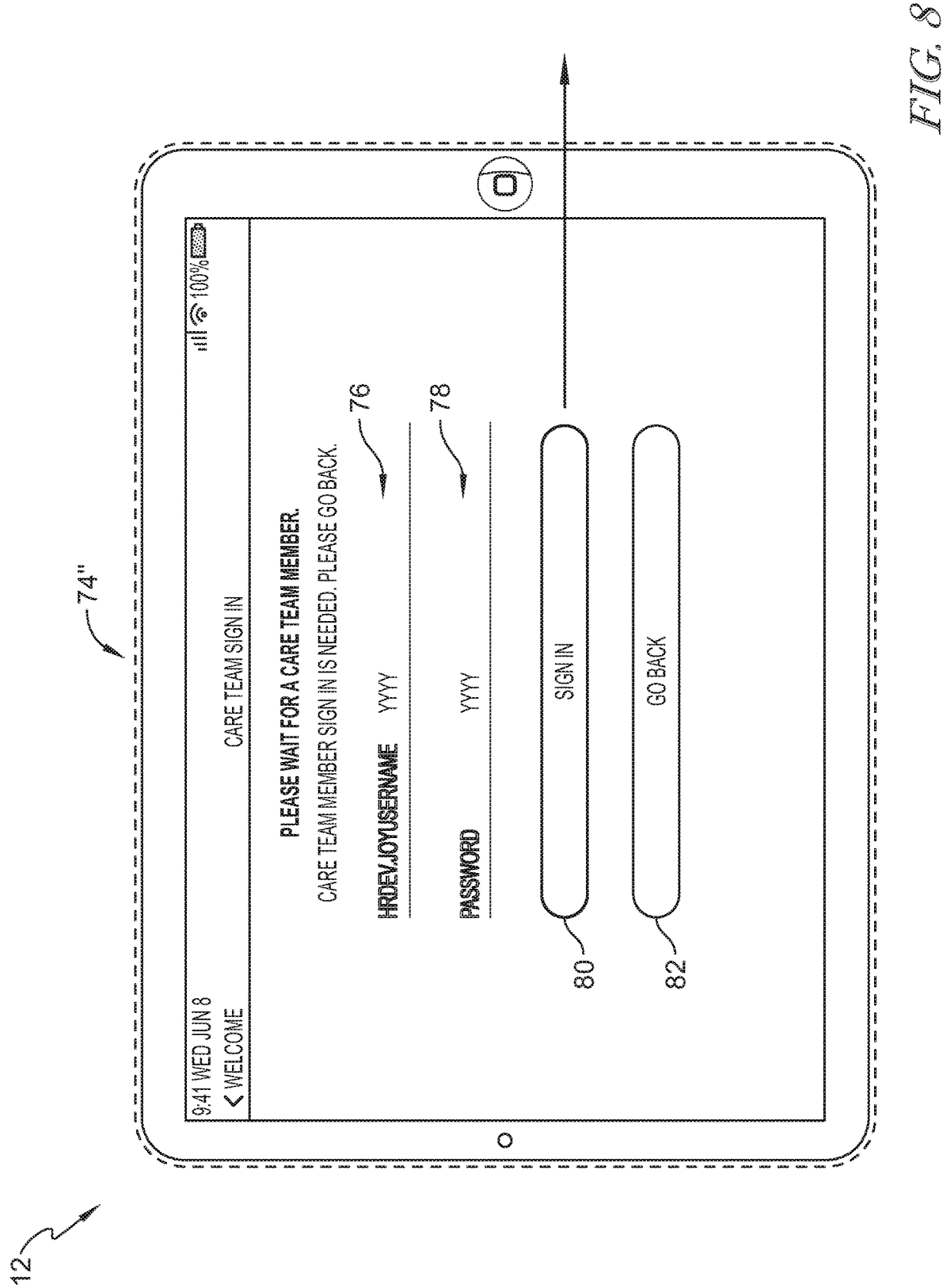
FIG. 8 is a duplicate of FIG. 5 but with proper credentials entered.
Figure 9:
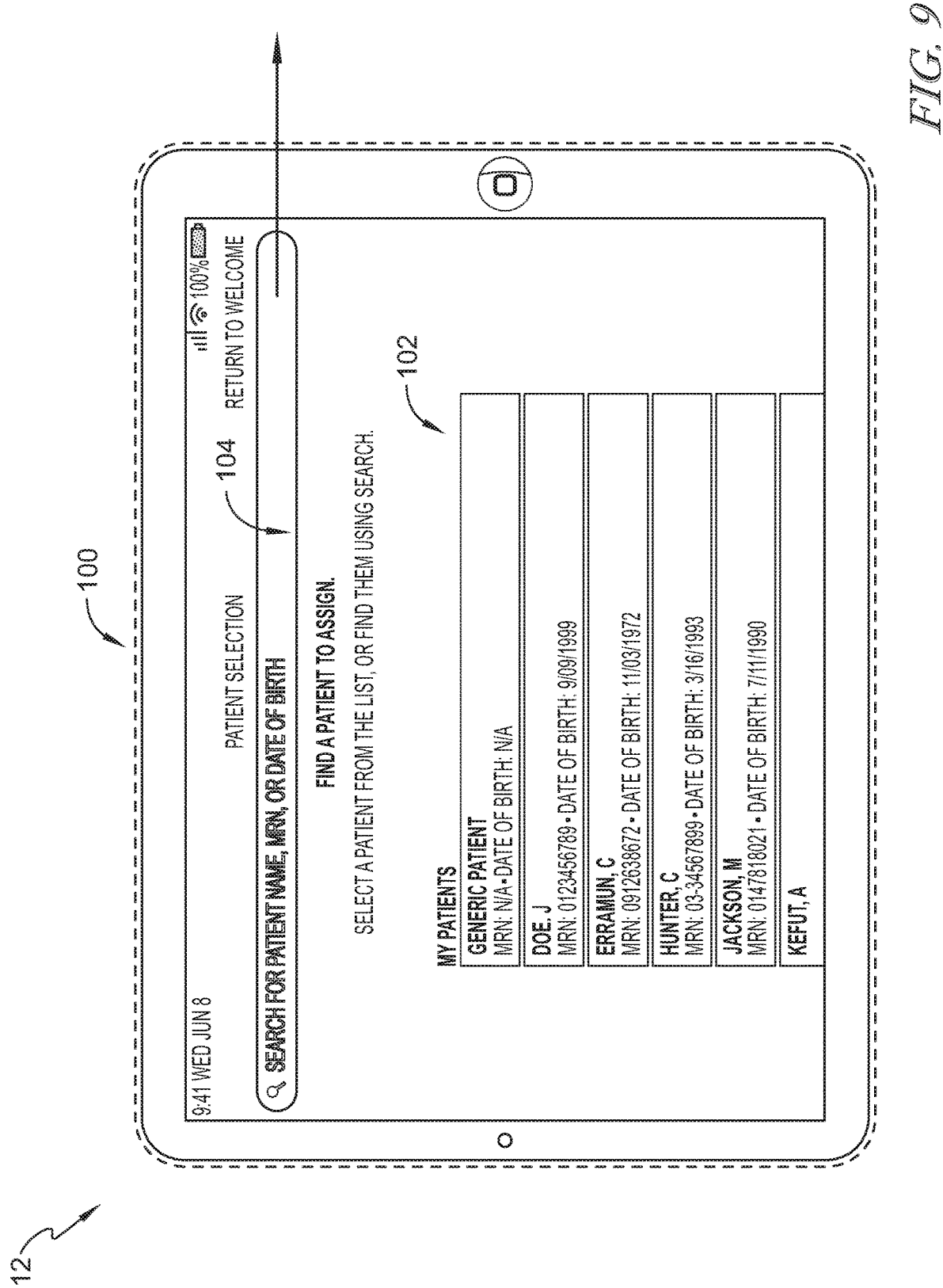
FIG. 9 is a screen shot of a patient selections screen listing the patients that are assigned to the caregiver.
Figure 10:
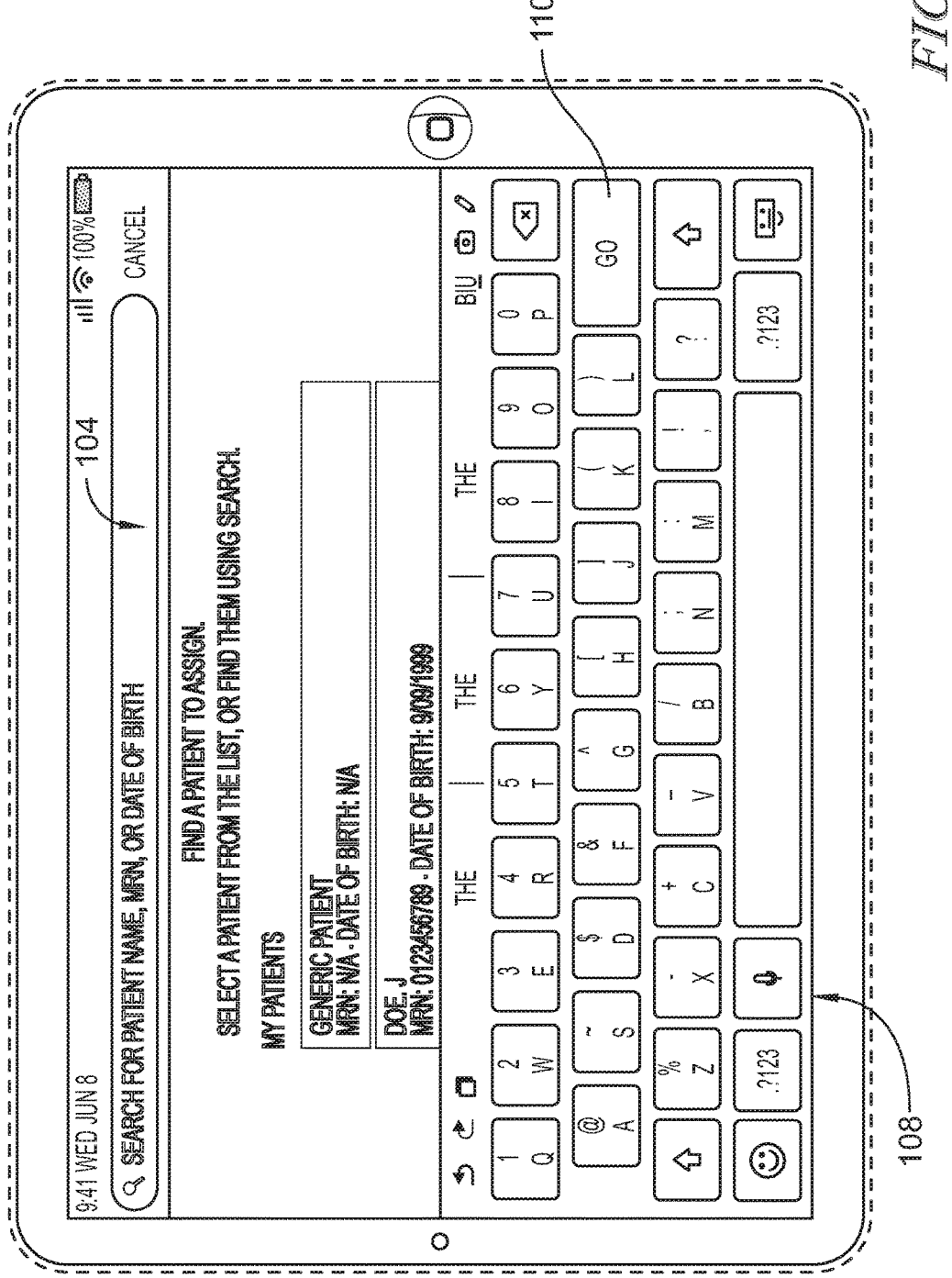
FIG. 10 is a screen shot of a patient search screen that the caregiver uses to search for a particular patient to which the tablet is to be assigned.

If a correct user name is entered in field 76 and if a correct password is entered in field 78, as suggested in screen 74" of FIG. 8, then in response to selection of the sign in button 80, a patient selections screen 100 appears on the tablet 12 as shown in FIG. 9. Screen 100 includes a listing 102 of the patients that are assigned to the caregiver. The caregiver can select a patient from listing 102 to which the tablet 12 is to be assigned, or the caregiver can select a search field 104 to cause a patient search screen 106 to appear on the tablet 12 as shown in FIG. 10. Screen 106 includes a keyboard 108 that is used by the caregiver to enter a patient's name, or a portion thereof, in the search field 104 to search for a particular patient to which the tablet is to be assigned. A go button 110 is provided on keyboard 108 and is selected by the caregiver once the search string has been entered in field 104 to conduct the search for the desired patient.

Referring now to FIG. 11, an example of a first today screen 112 that appears on the tablet 12 after the patient has been successfully assigned to tablet 12 and uses the tablet 12 for the first time. Screen 112 includes a date and time text box 114 that shows the date and time. Screen 112 also includes a weather text box 116 that shows the temperature and weather status (e.g., partly sunny). Box 116 is populated by information obtained from the weather API 24. Screen 112 further includes an informational text box 118 that provides information about the patient engagement software of tablet 12. Screen 112 includes a main menu 120 at the bottom of the screen. Main menu 120 includes a today icon or button 122, a my stay icon 124, a my requests icon 126, and a learn icon 128. The terms button and icon are used interchangeably herein. Finally, screen 112 includes a make a request button 130 that is selected by the patient when the patient wishes to make a specific request to one or more of the patient's assigned caregivers.

Figure 12:
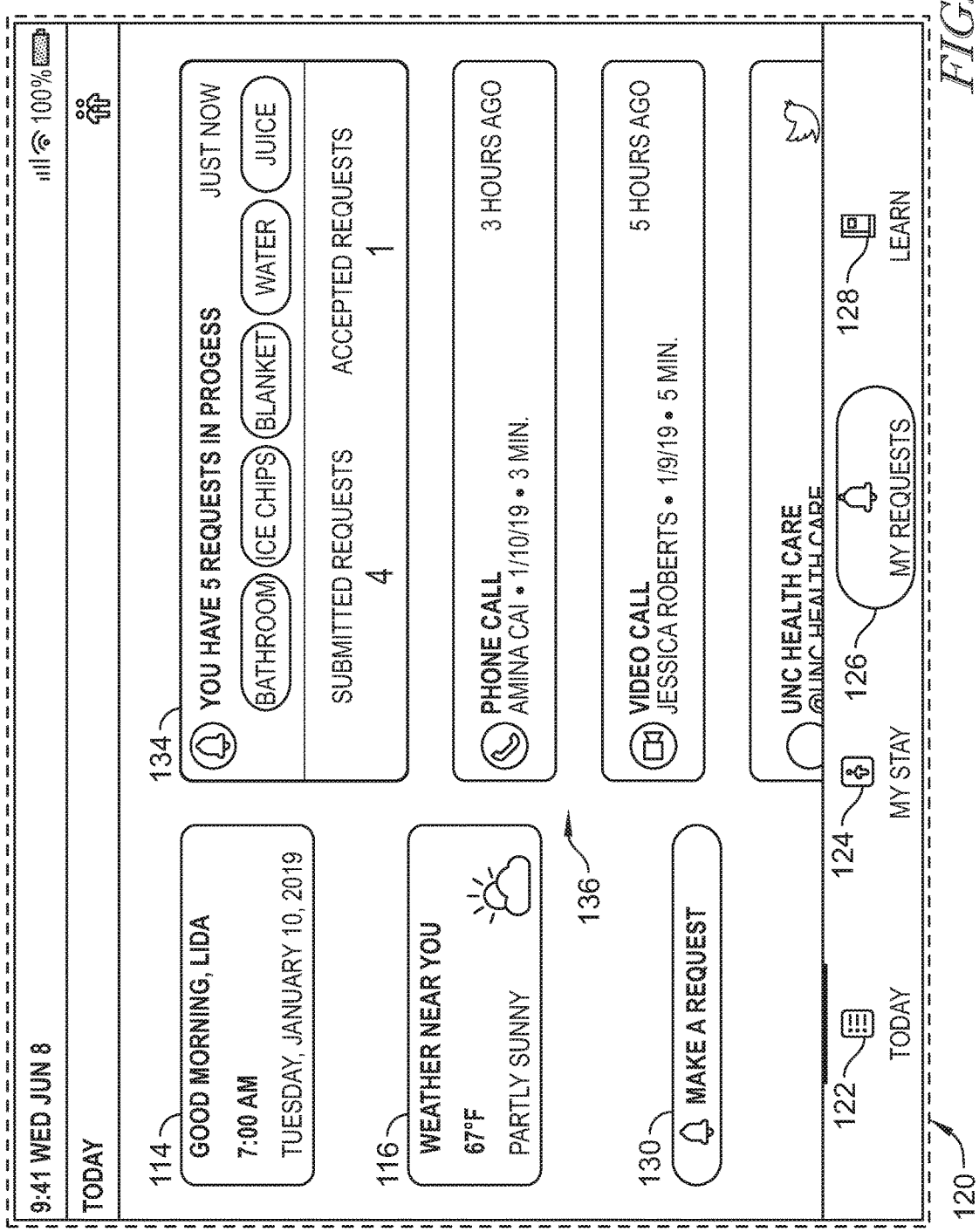
FIG. 12 is a screen shot of a second today screen that appears on the tablet to provide information about the requests that are in progress for the patient.
Figure 13:
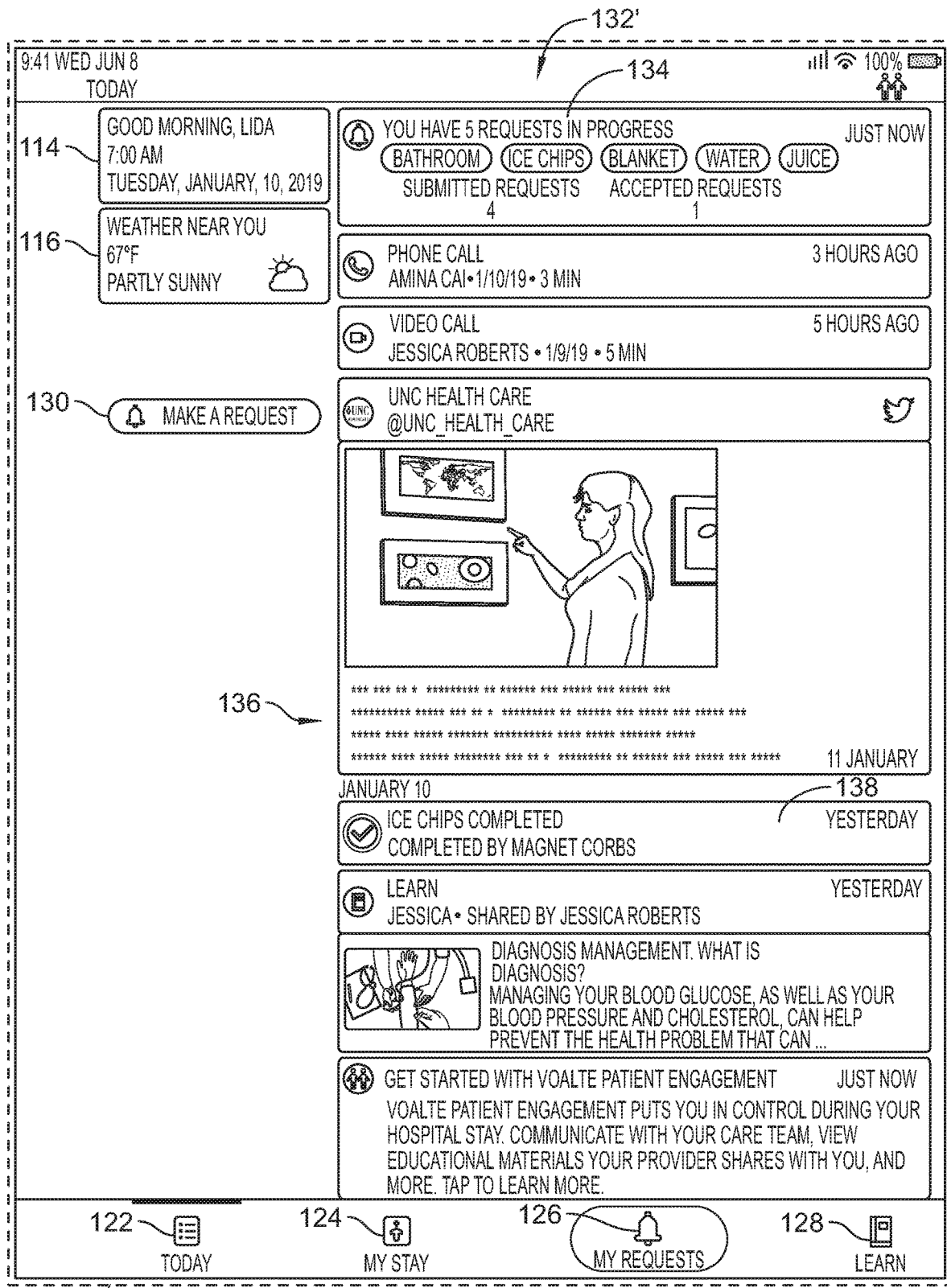
FIG. 13 is a screen shot of a third today screen showing a newsfeed that appears on the tablet if the patient decides to scroll on the tablet.

Referring now to FIG. 12, an example of a second today screen that appears on the tablet 12 after the patient has used various features of the patient engagement software of the tablet 12. Screen 132 includes a requests in progress text box 134 that provides information about the requests that are in progress for the patient. Box 134 indicates that the patient has five requests in progress. Four of the requests have been submitted and one of the requests has been accepted. Box 134 contains icons indicating that the five requests are bathroom, ice chips, blanket, water, and juice. Beneath box 134, is an activity list 136 indicating that the patient used tablet 12 to participate in a phone call three hours ago, to participate in a video call five hours ago, and to receive a tweet message from UNC Health Care. FIG. 13 shows an expanded today screen 132' in which more information about newsfeeds of activity list 136 appears and can be viewed on the tablet 12 if the patient decides to scroll on the tablet 12. Screen 132' also has a text box 138 which indicates that an ice chips request was completed on Jan. 10. The name of the caregiver who completed the ice chips request is also listed in box 138. Screens 112, 132, 132' of FIGS. 11-13, respectively, appear on the tablet when today icon 122 of main menu 120 is selected.

Figure 14:
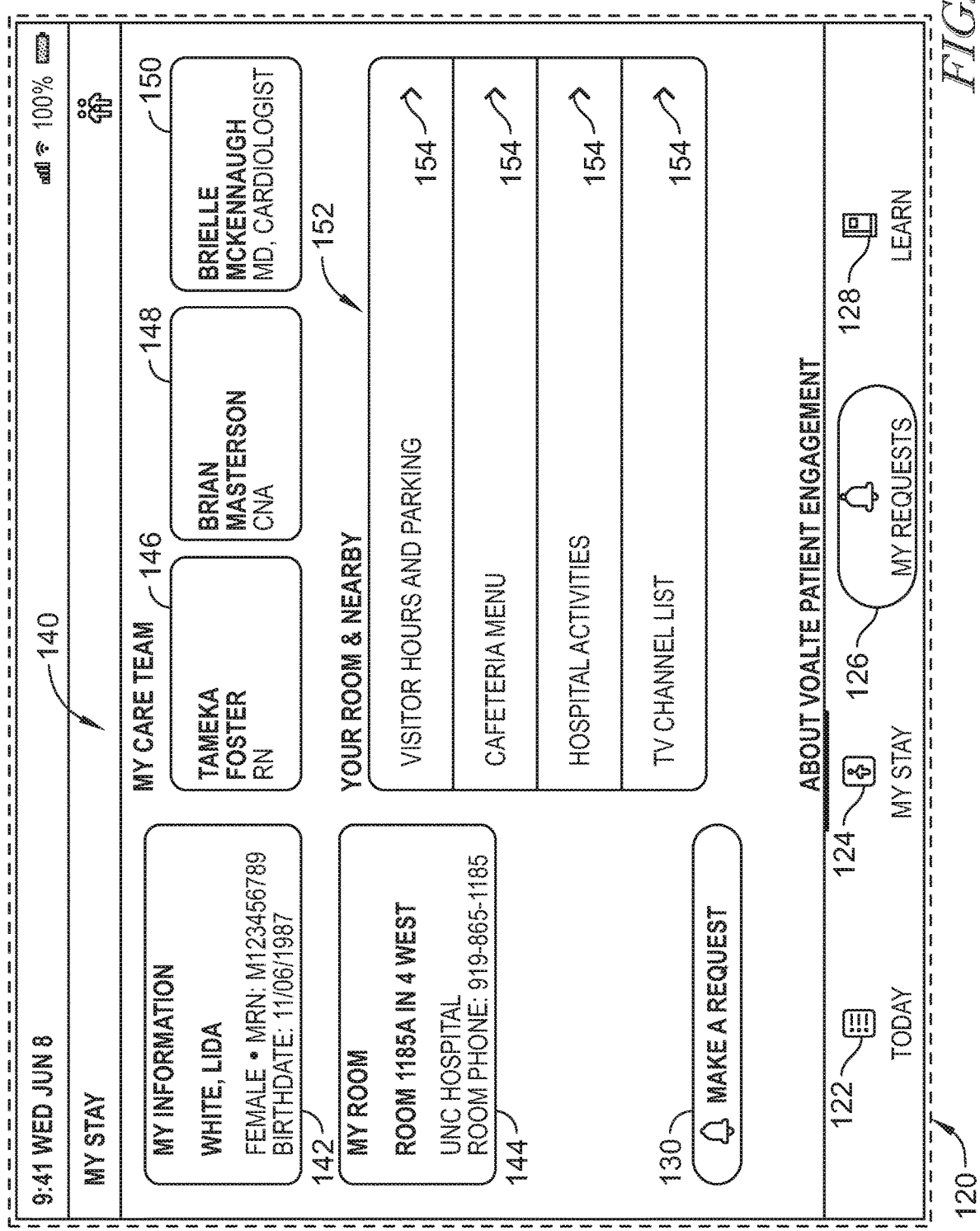
FIG. 14 is a screen shot of a first my stay page that appears on the tablet in response to the patient selecting a my stay button on a menu at the bottom of the tablet.

Referring now to FIG. 14, an example of a first my stay page or screen 140 appears on the tablet 12 in response to the patient selecting the my stay button 124 on menu 120 at the bottom of the tablet 12. Screen 140 includes a my information text box 142 that includes the patient's name (Lida White in the illustrative example), sex (male or female), medical record number (MRN), and birthdate. Beneath box 142 is a my room text box 144 that includes the patient's room number and wing (Room 1185A in 4 West in the illustrative example), the name of the hospital or healthcare facility, and the room phone number. Screen 140 also includes first, second, and third my care team boxes 146, 148, 150 which lists the name and role of the caregivers assigned to the patient. Boxes 146, 148, 150 are updated when a caregiver shift ends and a new caregiver is assigned to the patient.

Figure 15:
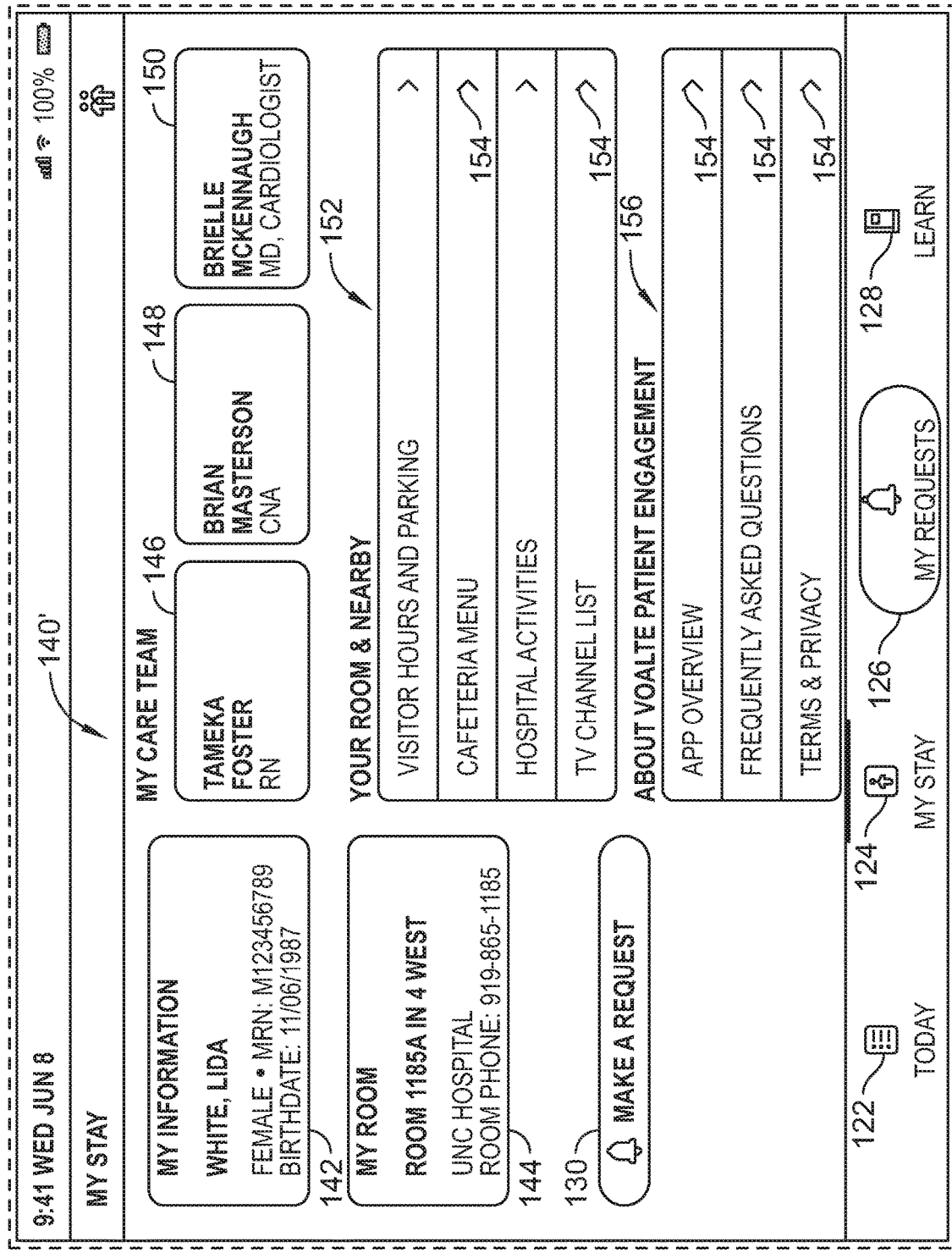
FIG. 15 is a screen shot of a second my stay page that appears on the tablet if the patient decides to scroll on the tablet.

Screen 140 also includes a table 152 with rows having arrow icons 154 that the patient can select to obtain more information about the particular item in each of the rows. In the illustrative example, table 152 includes the following text in the rows from top to bottom: Visitor Hours and Parking, Cafeteria Menu, Hospital Activities, and TV Channel List. FIG. 15 shows an expanded my stay screen 140' in which a software information table 156 appears and can be viewed on the tablet 12 if the patient decides to scroll on the tablet 12. Table 156 also includes arrow icons 154 that the patient can select to obtain more information about the particular item in reach row of table 156. In the illustrative example, table 156 includes the following text in the rows from top to bottom: App Overview, Frequently Asked Questions, and Terms & Privacy.

Figure 16:
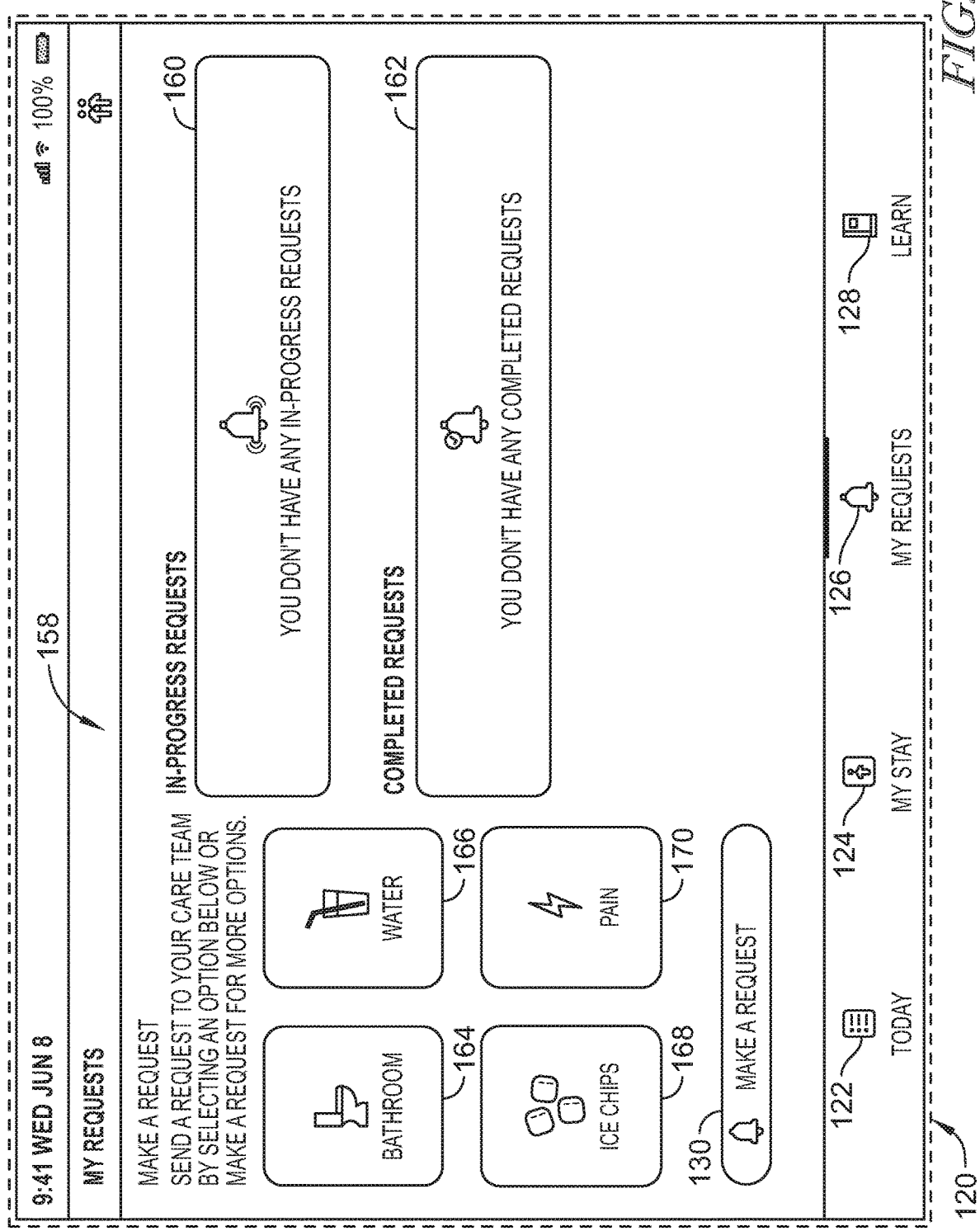
FIG. 16 is a screen shot of a first my requests screen that appears on the tablet in response to the patient selecting my requests button at the bottom of the tablet.

Referring now to FIG. 16, an example of a first my requests screen 158 that appears on the tablet in response to the patient selecting the my requests button 126 on the menu 120 at the bottom of the tablet 12. In the illustrative example of screen 158, an in-progress requests text box 160 indicates that the patient does not have any in-progress requests that have been made previously and a completed requests text box 162 indicates that the patient does not have any completed requests that have been fulfilled by caregivers previously. At the left side of screen 158 four request icons or buttons appear, namely, a bathroom icon 164 that the patient selects to request assistance in going to the bathroom, a water icon 166 that the patient selects to request water, an ice chips icon 168 that the patient selects to request ice chips, and a pain icon 170 that the patient selects to request pain medication or other help in dealing with pain.

Icons 164, 166, 168, 170 on screen 158 relate to highly requested items for the healthcare facility. The four icons relating to highly requested items may vary by unit such as for example, the four icons on screen 158 may be programmed by a system administrator to be different for a maternity unit that for a med/surg unit. It is also contemplated by the present disclosure that server 14 or another server of system 10, such as server 46, can monitor patient requests over time and automatically change the four icons appearing on screen 158 to match the four most common requests that are made based on historical data for the healthcare facility or the particular unit of the healthcare facility.

Figure 17:
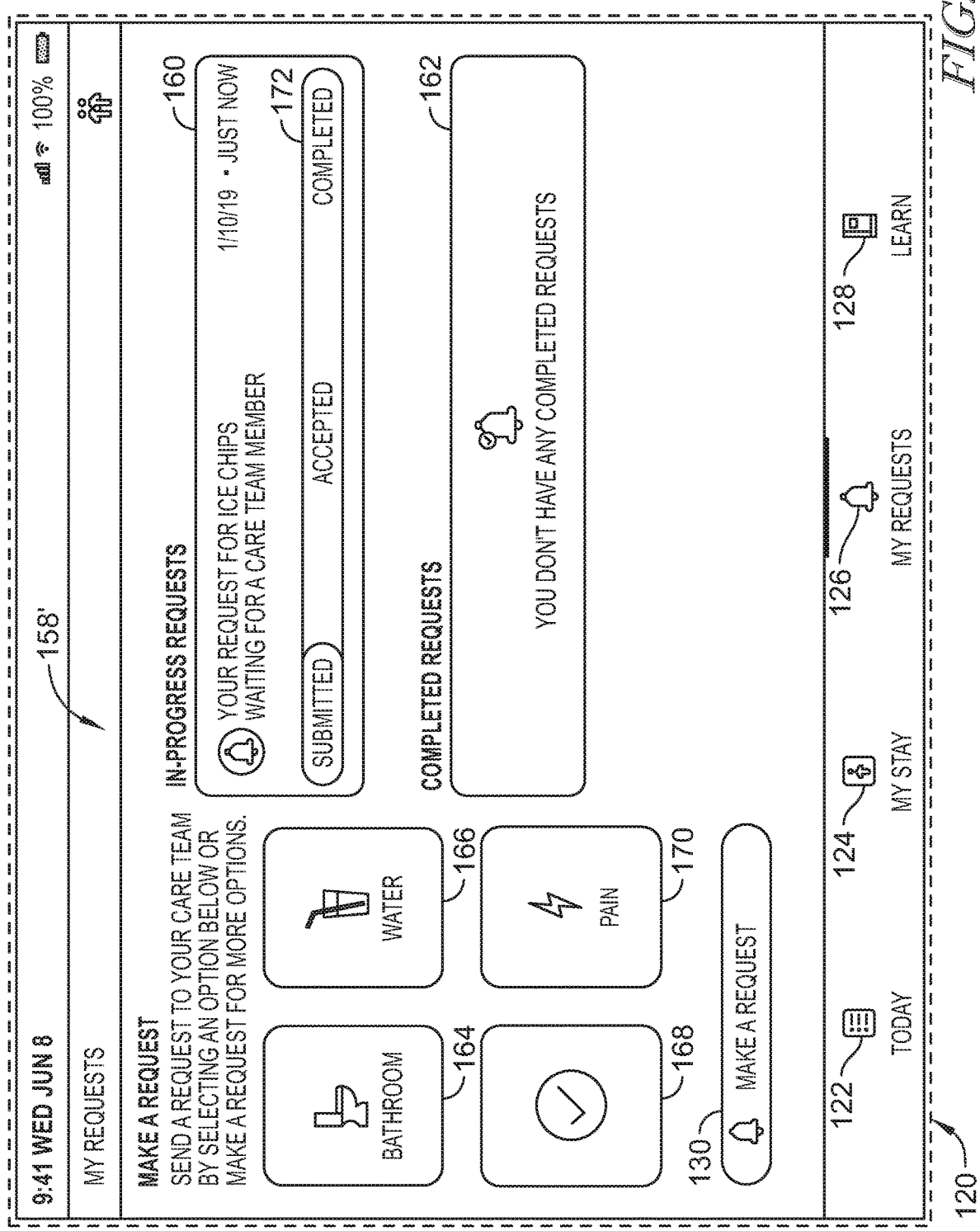
FIG. 17 is a screen shot of a second my requests screen that appears on the tablet after the patient has requested ice chips.

A message appearing on screen 158 above icons 164, 166 advises the patient that, if desired, he or she can select one of the four icons 164, 166, 168, 170 to make the respective request, or the patient has the option of selecting the make a request button 130 to see more request options. As shown in FIG. 17, an example of a second my requests screen 158' appears on the tablet 12 after the patient has requested ice chips via selection of button 168 on screen 158. In-progress requests text box 160 is updated to indicate that the patient has made the request for ice chips and the ice chips button 168 is updated to include a check mark indicia to indicate that button 168 has an active request pending or in-progress. In the illustrative example, a message is also provided in box 160 indicating that system 10 is waiting for a caregiver to accept the request.

A request progress bar 172 is shown in box 160 of screen 158' with the words submitted, accepted, and completed. The current status of the request in box 160 is communicated to the patient by highlighting the appropriate word. In the illustrative example, the word submitted is highlighted to indicate that the request has been submitted. After one of the patient's assigned caregivers accepts the request, such as by pressing an accept icon on the caregiver's mobile device, then the word accepted becomes highlighted on bar 172 of box 160. After the request is completed by the caregiver and the caregiver logs the completion into system 10 such as by pressing a completed button on the caregiver's mobile device, the word completed becomes highlighted on bar 172 of box 160 and the completed request is then moved to the completed requests box 162.

Figure 18:
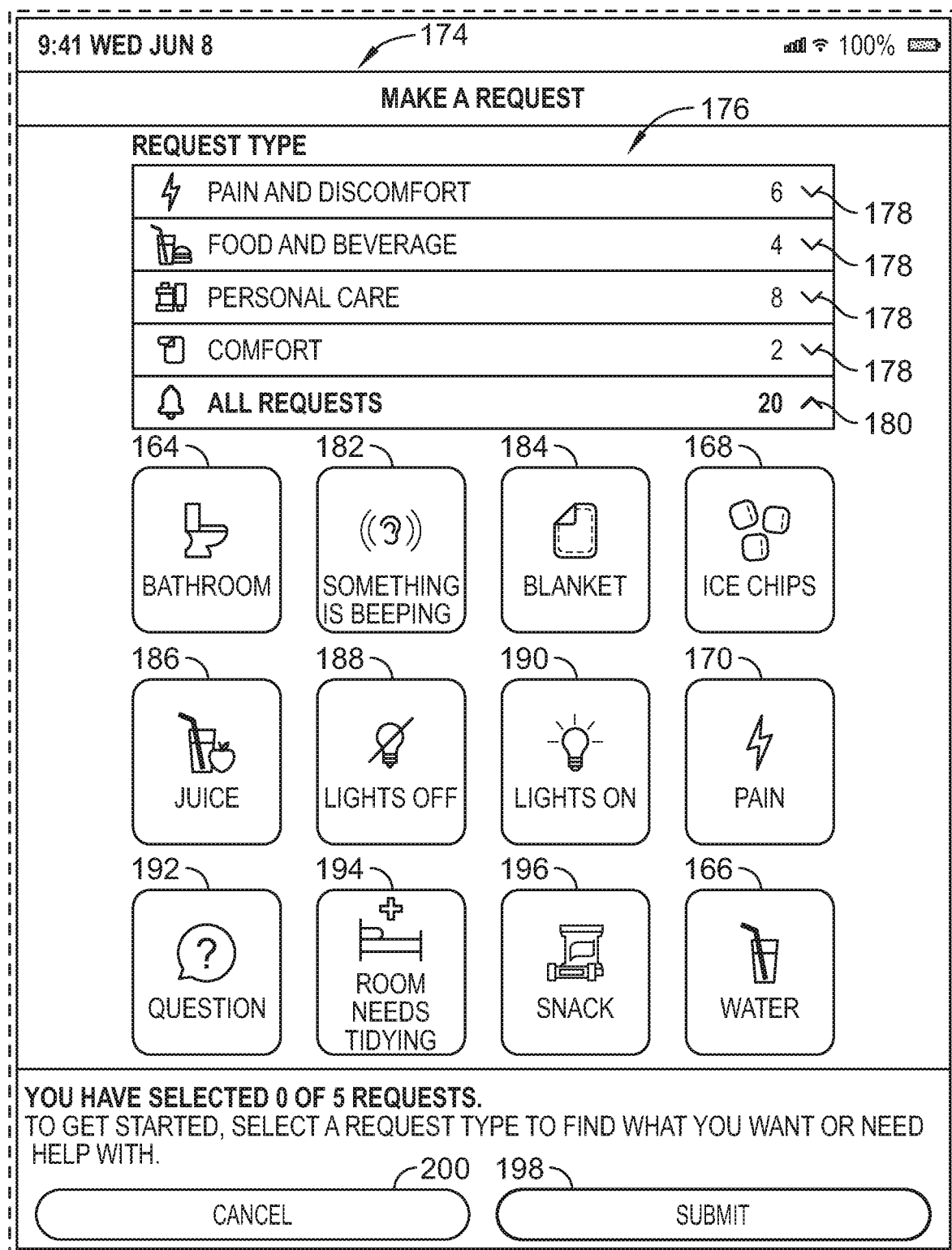
FIG. 18 is a screen shot of a first make a request screen that has a set of twelve icons on a menu for making a request by the patient.

Referring now to FIG. 18, a first make a request screen 174 that appears on the display screen of tablet 12 in response to the patient selecting button 130 on any of the screens discussed above having button 130. Screen 174 includes a table 176 having rows that show a first menu of basic categories of requests. In the illustrative example, the rows of table 176 from top to bottom include the following basic request types or categories: pain and discomfort, food and beverage, personal care, comfort, and all requests. A down arrow icon 178 appears at the right side of the first four rows of table 176 and is selectable by the patient to see a second menu of request options. Thus, the second menu corresponds to specific patient requests that fall under the basic request category selected by the patient using the first menu of table 176.

A numerical value indicating the number of specific patient request options that fall under each basic category of table 176 is shown just to the left of the down arrow icons 178. Thus, in the illustrative example, the second menu corresponding to the pain and discomfort basic category has six specific patient request options, the second menu corresponding to the food and beverage basic category has four specific patient request options, the second menu corresponding to the personal care basic category has eight specific request options, and the second menu corresponding to the comfort basic category has two specific request options.

In the illustrative example of screen 174 in FIG. 18, the all requests basic category has been selected by the patient and so the second menu appears corresponding to the all requests basic category appears on screen 174 as a set of specific patient request icons. An up arrow icon 180 is shown at the right side of the all requests row and is selectable by the patient to collapse the second menu of icons that currently appear on screen 174. In the illustrative example, the numerical value 20 appears on screen 174 just to the left of up arrow icon 180 to indicate that the total number (6+4+8+2=20) of second menu options corresponding to the basic categories of the first four rows of table 176.

Screen 174 of FIG. 18 shows a set of twelve specific patient request icons on the second menu corresponding to the all requests basic category, thereby indicating that the patient needs to scroll on tablet 12 to uncover the remaining eight specific patient request icons. The twelve specific patient request icons appearing in the second menu of screen 174 include the four icons 164, 166, 168, 170 discussed previously, plus the following eight additional specific patient request icons: a something is beeping icon 182 that is selected by the patient when a piece of equipment in the patient room, such as an intravenous (IV) pump, starts beeping; a blanket icon 184 that the patient selects to request a blanket; a juice icon 186 that the patient selects to request juice; a lights off icon 188 that the patient selects to request that the room lights be turned off; a lights on icon 190 that the patient selects to request that the room lights be turned on; a question icon 192 that the patient selects to ask a question of a general nature not corresponding with any of the other icons of the second menu of screen 174; a room needs tidying icon 194 that the patient selects to request that the room be cleaned; and a snack icon 196 icon that the patient selects to request a snack.

At the bottom of screen 174 beneath the icons of the second menu, the following text appears, "You have selected 0 of 5 requests. To get started, select a request type to find what you want or need help with." This text is shown on screen 174 in lieu of the second menu when the patient has not yet selected any basic category from table 176. In other words. FIG. 18 shows the text at the bottom of screen 174 appearing at the same time as the second menu, but in real world embodiments, these are mutually exclusive on screen 174. Screen 174 also has a submit button 198 and a cancel button 200 beneath the second menu. Thus, if desired, the patient is able to select multiple ones of buttons 164, 166, 168, 170, 182, 184, 186, 188, 190, 192, 194, 196 on the second menu and then select the submit button 198 to submit the multiple specific patient requests simultaneously through system 10. In some embodiments, the multiple number of simultaneous requests that can be made on screen 174 using tablet 12 is limited to a maximum number, such as five requests in the illustrative example. If the patient decides not to submit any specific patient requests while viewing screen 174, the patient selects the cancel button 200 to return back to the previous screen on which button 130 was originally selected.

Figure 19:
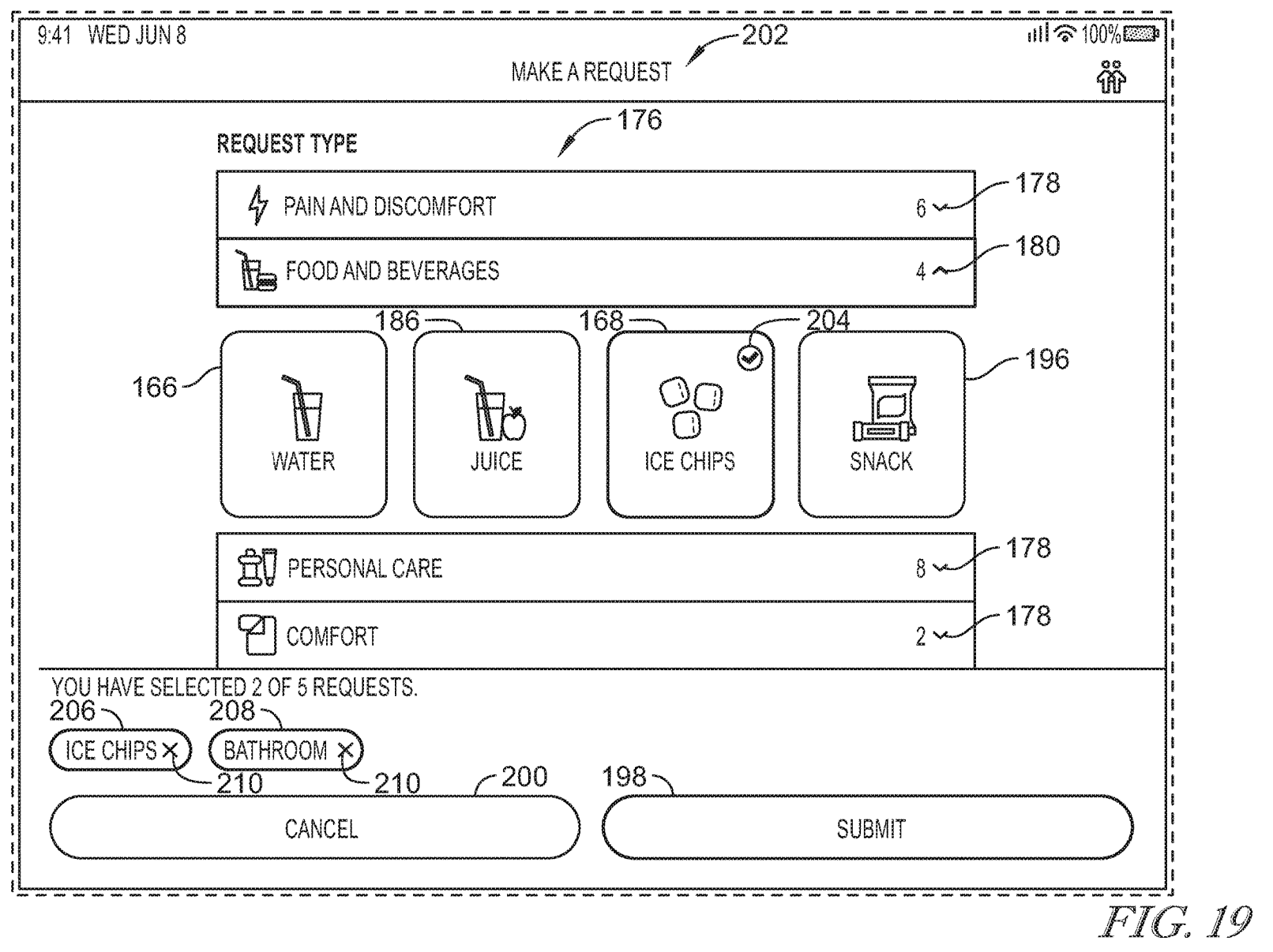

Referring now to FIG. 19 an example of a second make a request screen 202 shows that the food and beverage basic category of table 176 has been selected by the patient and a set of four icons, namely, icons 166, 168, 186, 196 discussed above, are shown beneath the food and beverage row. Thus, icons 166, 168, 186, 196 correspond to the second menu of specific patient request options that are associated with the food and beverage basic category of the first menu of table 176. In the illustrative example, the ice chips button 168 has been selected and a check mark indicia 204 appears in the upper right corner of button 168 to indicate the selection. A border around button 168 is also highlighted to further indicate the selection. Down arrow icons 178 and up arrow icon 180 are also shown in the appropriate rows of table 176 of screen 202 for selection by the patient to reveal or hide, as the case may be, the second menu buttons corresponding to the basic category rows of table 176.

Beneath table 176 of screen 202, the text "You have selected 2 of 5 requests" is displayed to indicate that the patient has selected two specific patient requests out of the five maximum possible patient requests that are permitted to be submitted simultaneously in the illustrative embodiment. An ice chips button 206 and a bathroom button 208 appears beneath the text to indicate which two requests have been made by the patient. A cancel icon 210 (illustratively, an "x") appears in each button 206, 208 and is selectable to cancel the corresponding patient request while leaving the other patient requests active for submission. If the patient desires to cancel all listed requests, the patient selects cancel button 200. After the patient has made all of the desired specific patient request selections using the first menu of table 176 and the corresponding second menus, up to a maximum of five specific patient requests, the patient selects the submit button 198 to submit the multiple specific patient requests simultaneously through system 10.

Figure 20:
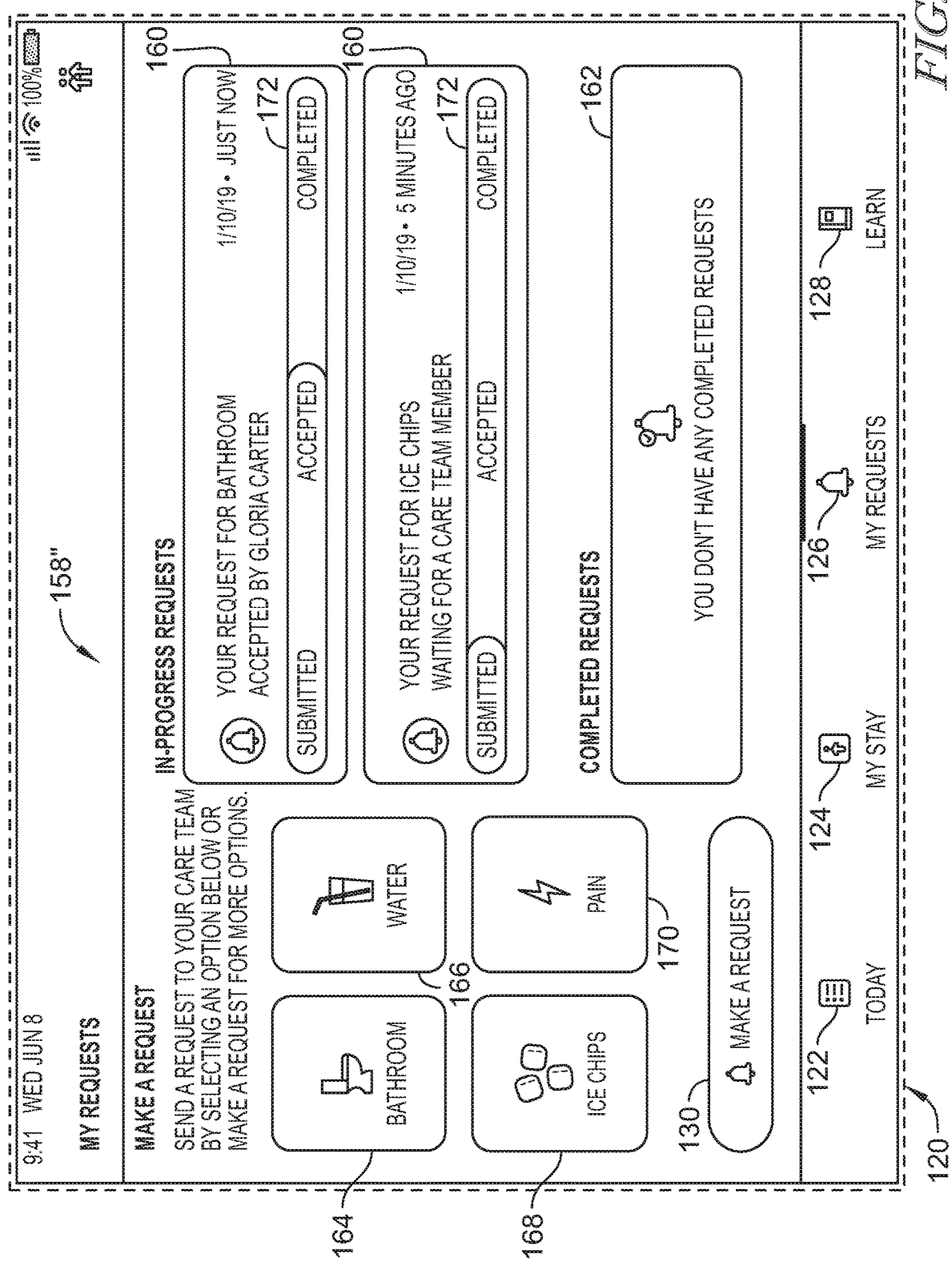
FIG. 20 is a screen shot of an in-progress requests screen showing a list of requests that have been made by the patient but not yet completed.

Referring now to FIG. 20, another example of an in-progress requests screen 158" shows two requests appearing in corresponding in-progress requests text boxes 160. The two specific patient requests shown on screen 158" are for bathroom assistance and for ice chips, but neither of the requests have been completed. The status bar 172 of the upper text box 160 of screen 158" indicates via highlighting that the request for bathroom assistance has been submitted and accepted and the status bar 172 of the lower text box 160 of screen 158" indicates via highlighting that the request for ice chips has been submitted but not yet accepted. For the accepted bathroom assistance request, the upper text box 160 indicates the name of the caregiver that accepted the request (Gloria Carter in the illustrative example). The discussion above of screen 158 of FIG. 16 and of screen 158' of FIG. 17 is equally applicable to screen 158", except where noted otherwise, and similar reference numbers are used in each of these screens.

As indicated on screen 158" of FIG. 20, the most recent patient request appears as the uppermost text box 160 and the oldest patient request appears as the lowermost text box 160 in the list of text boxes 160. In the illustrative example, the two patient requests were submitted separately by the patient and in particular, the bathroom request was submitted "just now" and the ice chips request was submitted "5 minutes ago." If the patient submits multiple requests simultaneously, such as discussed above in connection with FIGS. 18 and 19, then an arbitrary listing scheme is used for the patient requests such as listing them alphabetically or listing them in the same order that the patient selected them using the first menu of table 176 and corresponding second menus as discussed above in connection with FIGS. 18 and 19.

Figure 21:
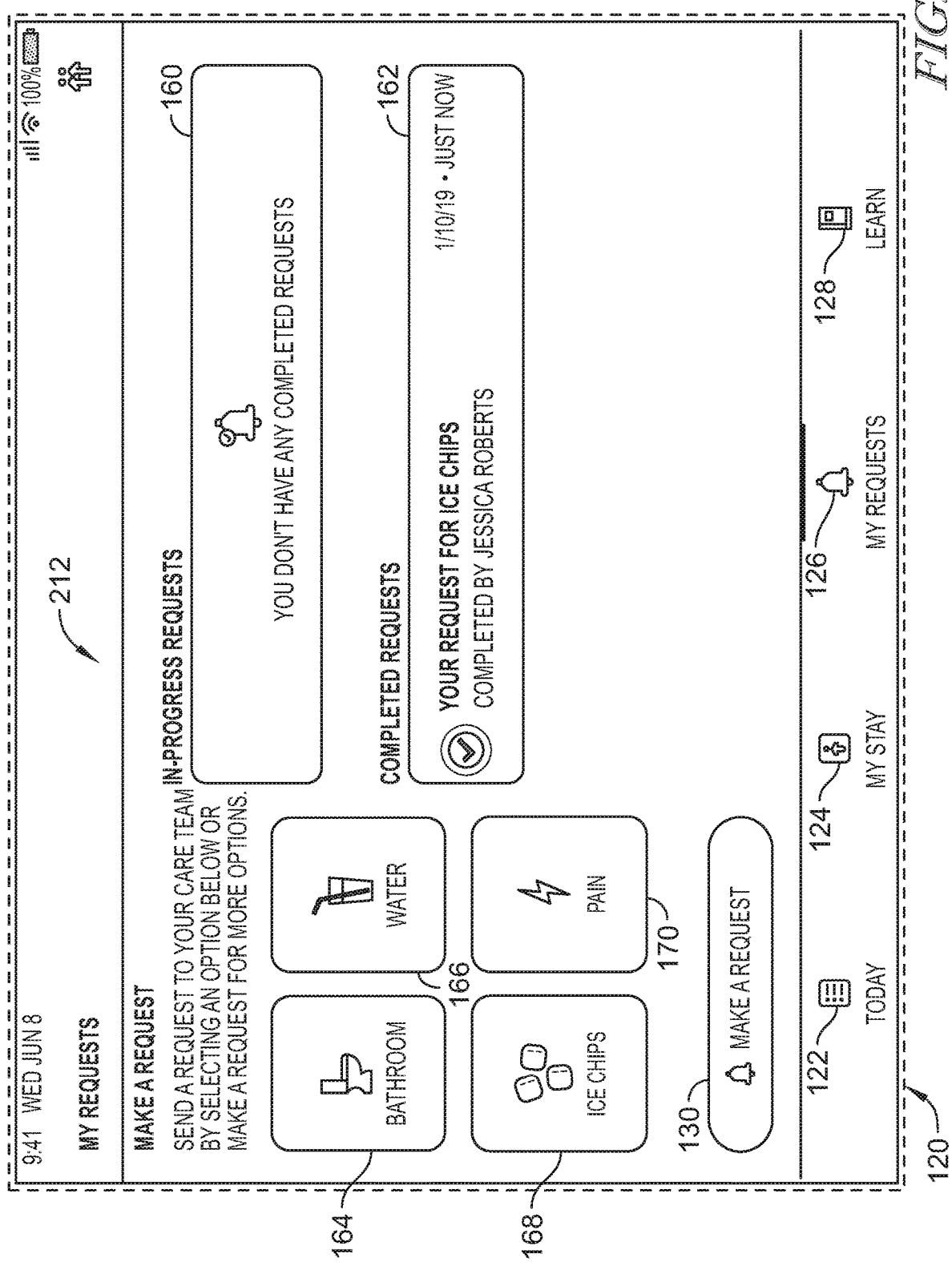
FIG. 21 is a screen shot of a completed requests screen showing a list of requests that have been completed.

Referring now to FIG. 21, an example of a completed requests screen 212 is shown in which completed requests text box 162 indicates that the patient request for ice chips has been completed. Text box 162 also indicates the name of the caregiver that completed the request (Jessica Roberts in the illustrative example). If multiple requests are completed, then all such completed requests appear in further text boxes 162 under the Completed Requests heading. In some embodiments, the most recent completed request appears as the uppermost text box 162 and the oldest completed request appears as the lowermost text box 162 in the list of text boxes 162. The list of completed requests shows all requests completed during a set period of time such as for a day or a shift or a predetermined rolling period of time (e.g., eight hours, four hours, etc.) at the discretion of the designer or programmer of system 10. After the set period of time, the completed requests are removed from the list.

In some embodiments, the available requests of the patient engagement software are based on first and second menus such as those discussed above. The first menu provides a list of basic request categories on the display screen of tablet 12. Selection of one of the choices from the first menu causes the second menu to appear on the display screen of tablet 12. The second menu includes specific patient requests that fall under the basic request category selected by the patient using the first menu. Table 1 below shows an alternative embodiment of first and second menus that are implements in the patient engagement software of tablet 12. In particular, Table 1 lists the request category (aka first menu) as the first column and lists the request item (aka second menu) as the second menu.

TABLE 1

| Request Category (first menu) | Request Item (second menu) |
| --- | --- |
| I'm Thirsty | Water |
| I'm Thirsty | Ice |
| I'm Thirsty | Juice |
| I'm Thirsty | Ginger Ale |
| I'm Thirsty | Cola |
| I'm Thirsty | Diet Cola |
| I'm Thirsty | Clear Soda |
| I'm Thirsty | Clear Diet Soda |
| I'm Thirsty | Nutritional Drink |
| I'm Thirsty | Other Drink |
| I'm Hungry | Crackers |
| I'm Hungry | Meal |
| I'm Hungry | Jell-O |
| I'm Hungry | Other Snack |
| I'm Hungry | Popsicle |
| I Feel | Sick |
| I Feel | Pain |
| I Feel | Hot/Cold |
| I Feel | Cold Feet |
| I Feel | Can't sleep |
| I Feel | Other Need |
| Help Me With . . . | Get Up/Move |
| Help Me With . . . | Bandage Problem |
| Help Me With . . . | Clothes/Gown |
| Help Me With . . . | Blood Sugar Check |
| Help Me With . . . | IV Hurts |
| Help Me With . . . | Get a Bath |
| Help Me With . . . | Bathroom |
| Help Me With . . . | Brush Teeth |
| Help Me With . . . | Walk |
| Help Me With . . . | Collect Bathroom Specimen |
| Help Me With . . . | Other Problem |
| Services | Translator |
| Services | Chaplain/Clergy |
| Services | Case Manager/Social Worker |
| Services | Visitor Information |
| Services | Other Service |
| Room | I Can't Reach . . . |
| Room | Room Hot/Cold |
| Room | TV/Remote Control issue |
| Room | Adjust Bed |
| Room | Machine is Beeping |
| Room | Noisy |
| Room | Lights On/Off |
| Room | Sheet Change |
| Room | Spill |
| Room | Other Environmental |
| Bring Me . . . | Pen/Paper |
| Bring Me . . . | Ice Pack |

TABLE 1-continued

| Request Category (first menu) | Request Item (second menu) |
|---|---|
| Bring Me . . . | Pillow |
| Bring Me . . . | Other NEED |
| Bring Me . . . | Blanket |
| Bring Me . . . | Other Need |
| Mother/Baby | Pacifier |
| Mother/Baby | Baby To/From Nursery/Bassinet |
| Mother/Baby | Baby Care |
| Mother/Baby | Swaddling |
| Mother/Baby | Breastfeeding |
| Mother/Baby | Breast Pump |
| Mother/Baby | Pad |
| Mother/Baby | Bottle/formula |
| Mother/Baby | Diaper |
| Mother/Baby | Baby Wipes |
| Mother/Baby | Skin Time/Kangaroo Care |
| Mother/Baby | Baby Blanket |
| Mother/Baby | Other Need Mother |
| Mother/Baby | Other Need Baby |

In some embodiments of system 10, the mother/baby category of the first menu only appears on tablets 12 that are located in a maternity ward or that are assigned to patients in a maternity ward. In some embodiments, therefore, system 10 includes locating and tracking equipment that is used to determine the locations of tablets 12. For example, received signal strength at wireless access points can be used to determine the locations of tablets 12. As another example, wireless locating tags (e.g., radio frequency identification (RFID) tags, ultra wideband tags, infrared tags, etc.) attached to tablets 12 can send wireless signals to receivers of a locating system to determine the locations of tablets 12 in a healthcare facility. The receivers and wireless access points are in communication with a locating server which processes the data (e.g., tablet ID, tag ID, wireless access point ID, receiver ID, etc.) to determine the locations of tablets 12.

Figure 22:
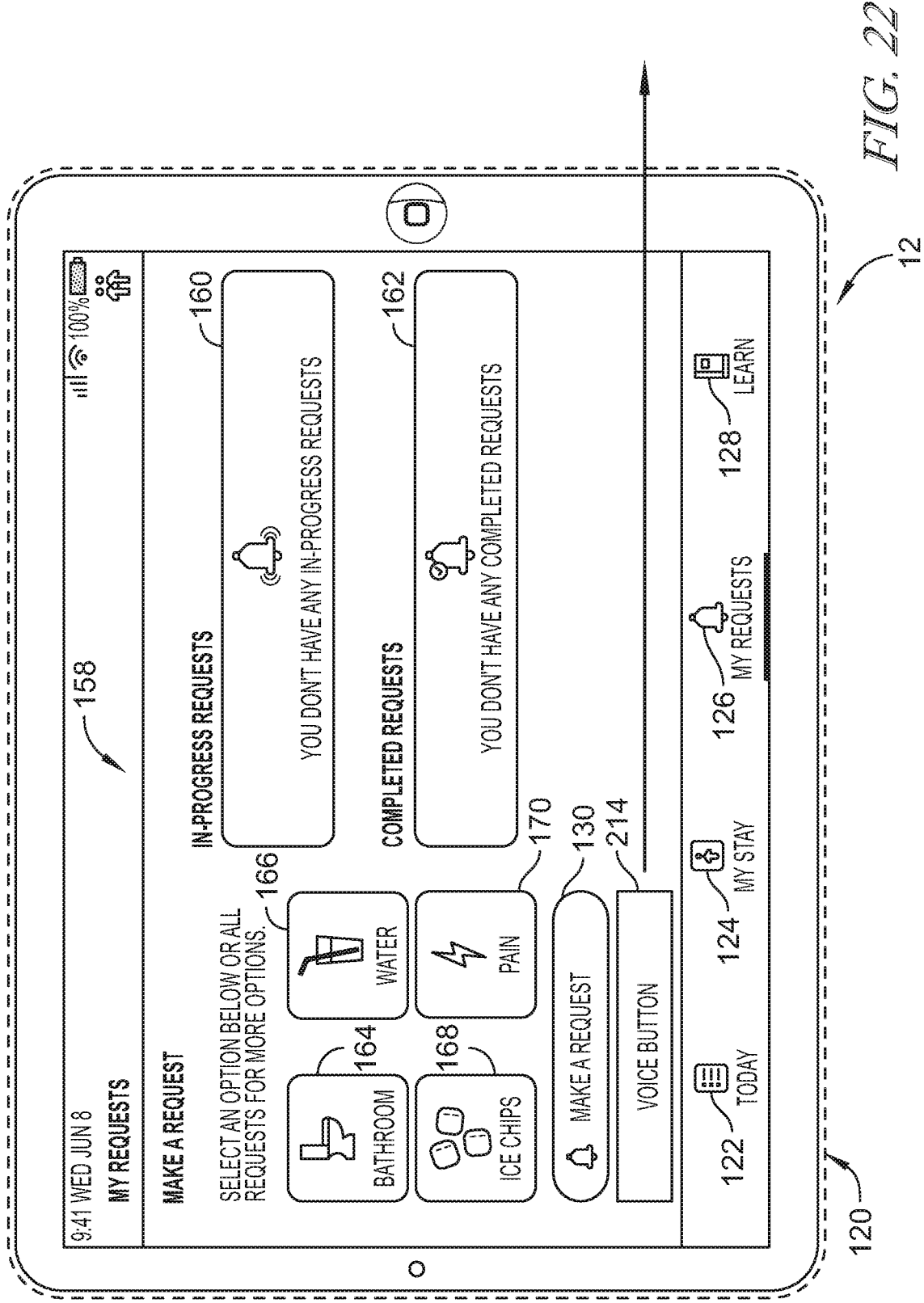
FIG. 22 is a screen shot of a my requests screen having a voice button that is selectable to permit the patient to make a request by voice.

According to some embodiments of system 10 contemplated herein, tablets 12 are configured to receive voice commands from patients in connection with making specific patient requests. In such embodiments, the may requests screen 158 includes a voice button 214 as shown in FIG. 22. The remainder of screen 158 of FIG. 22 is the same as screen 158 of FIG. 16 and so the same reference numbers are used to denote like portions of FIGS. 16 and 22. Thus, the description above FIG. 16 is equally applicable to FIG. 22 except where noted otherwise (e.g., inclusion of button 214 on screen 158 of FIG. 22).

Figure 23:
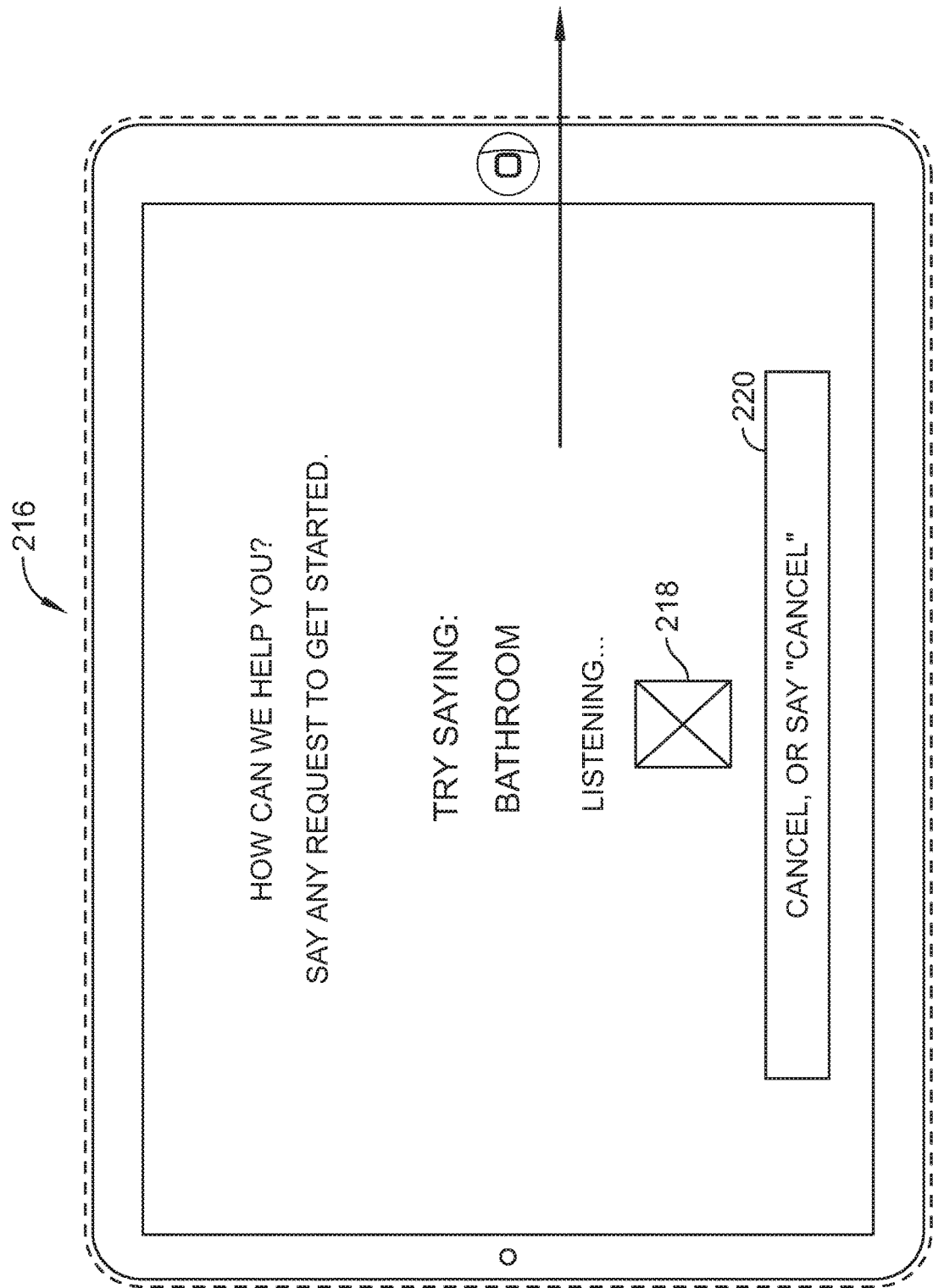
FIG. 23 is a screen shot of a voice request screen that appears in response to the voice button of FIG. 22 being selected.

In response to selection of the button on screen 158 of FIG. 22, the tablet 12 responds with a voice request screen 216 as shown in FIG. 23. Screen 216 includes the following text in the illustrative example: "How can we help you? Say any request to get started. Try saying Bathroom." Beneath the text on screen 216, a listening icon 218 appears to indicate to the patient that the tablet 12 is listening for a patient request made by voice command. More particularly, after selection of button 214, a microphone of tablet 12 is activated to receive vocal input from the patient. Screen 216 also includes a cancel, or say "cancel" button 220. If the patient decides not to make any patient requests by voice, the patient can either select button 220 on the display screen of tablet 12 or say the word "cancel" to return back to screen 158 of FIG. 22.

Figure 24:
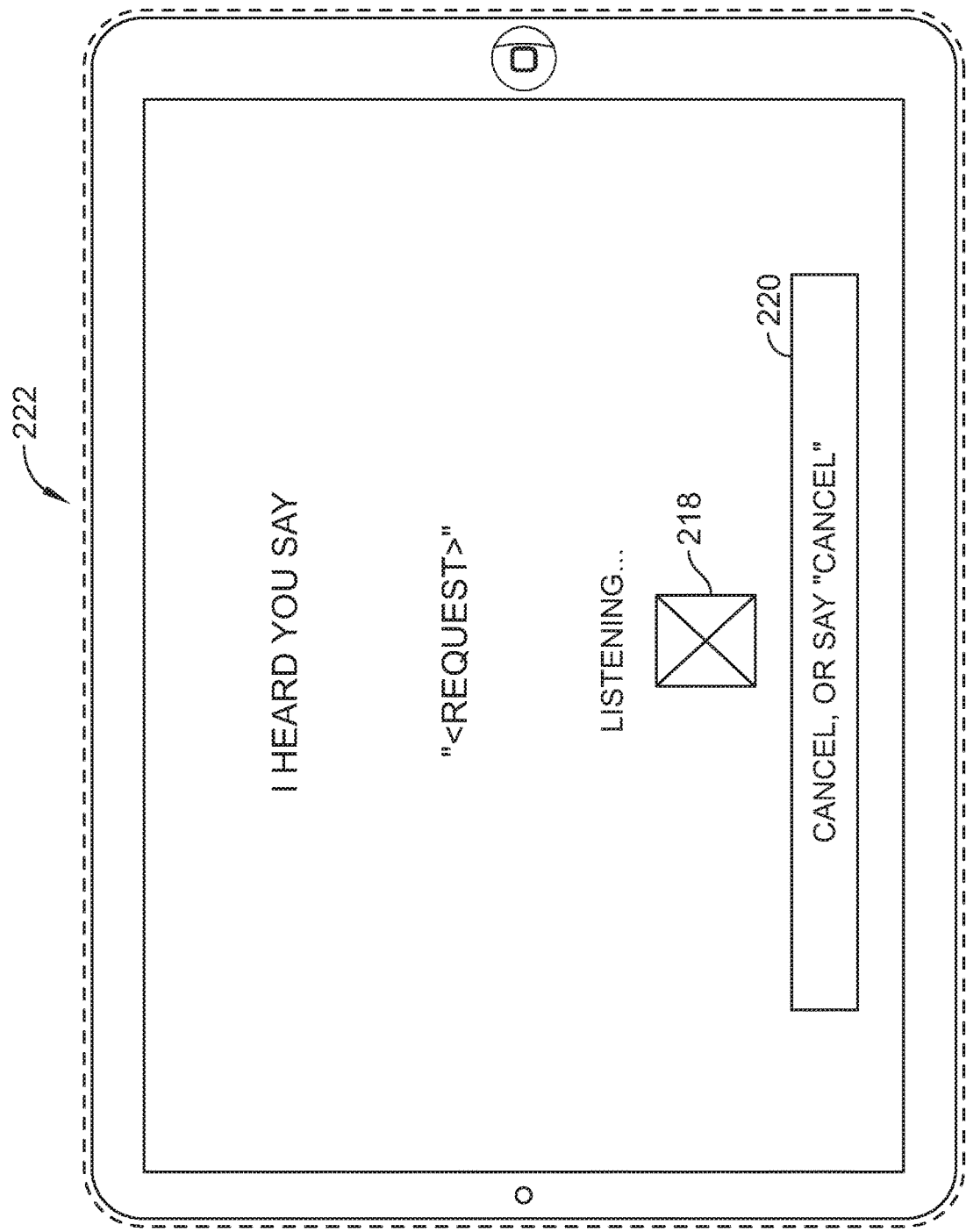
FIG. 24 is a screen shot of a first voice confirmation screen that appears in response to the patient making a voice request while viewing the voice request screen of FIG. 23.
Figure 25:
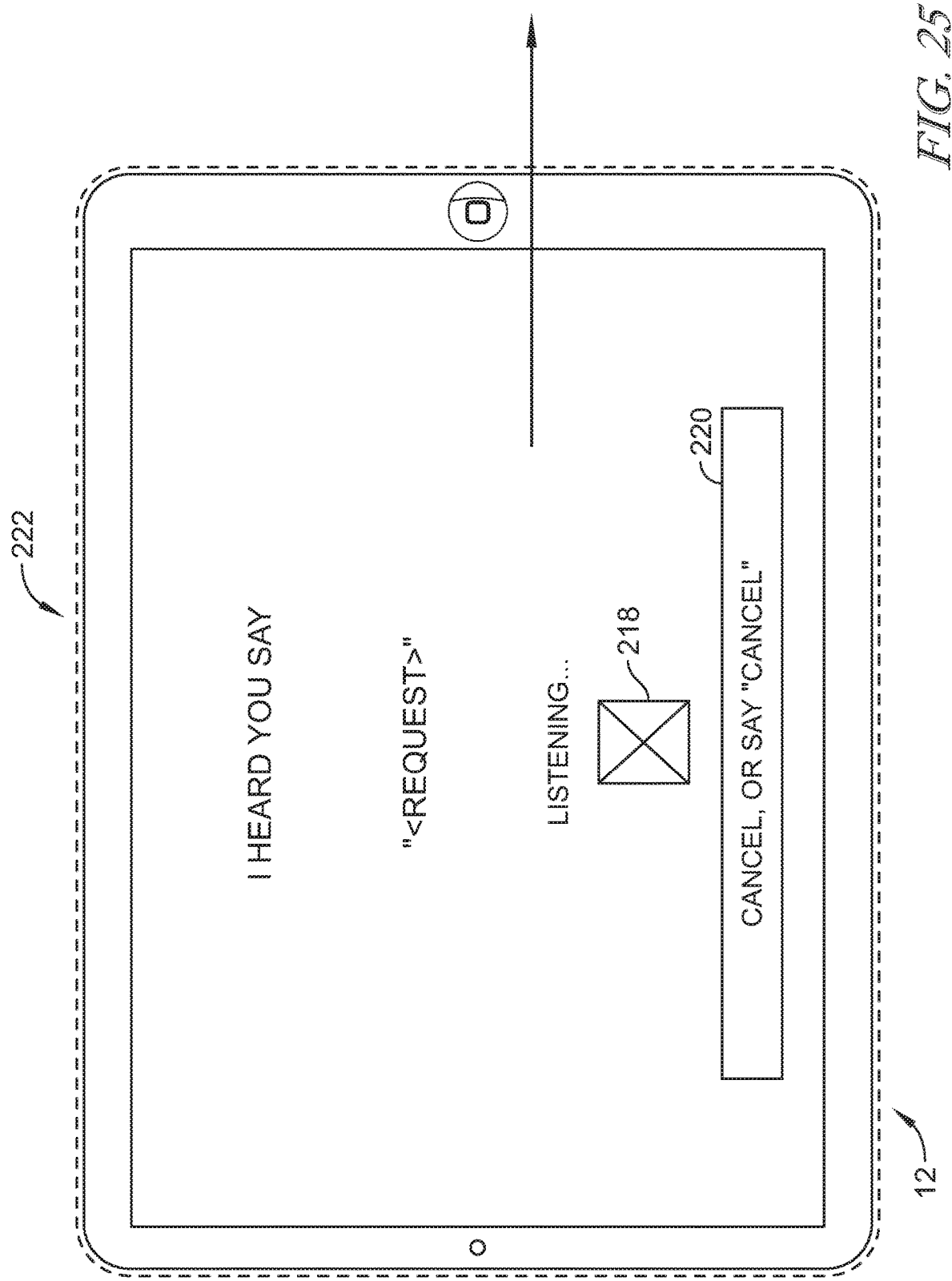
FIG. 25 is a duplicate of FIG. 24.

After the patient says a specific patient request vocally, a first voice confirmation screen 222 appears on tablet 12 as shown in FIG. 24. Screen 222 includes the text "I heard you say '<Request>'" with <Request> being a placeholder for the voice command that the patient actually stated. Screen also includes the listening icon 218 and the cancel, or say "cancel" button 220 that are used in the same manner as described in connection with screen 216 to return the patient back to screen 158 of FIG. 22 if the patient decides to cancel the patient request made by voice. FIG. 25 is a duplicate of FIG. 24 but is shown on the next drawing sheet for ease of reference.

Figure 26:
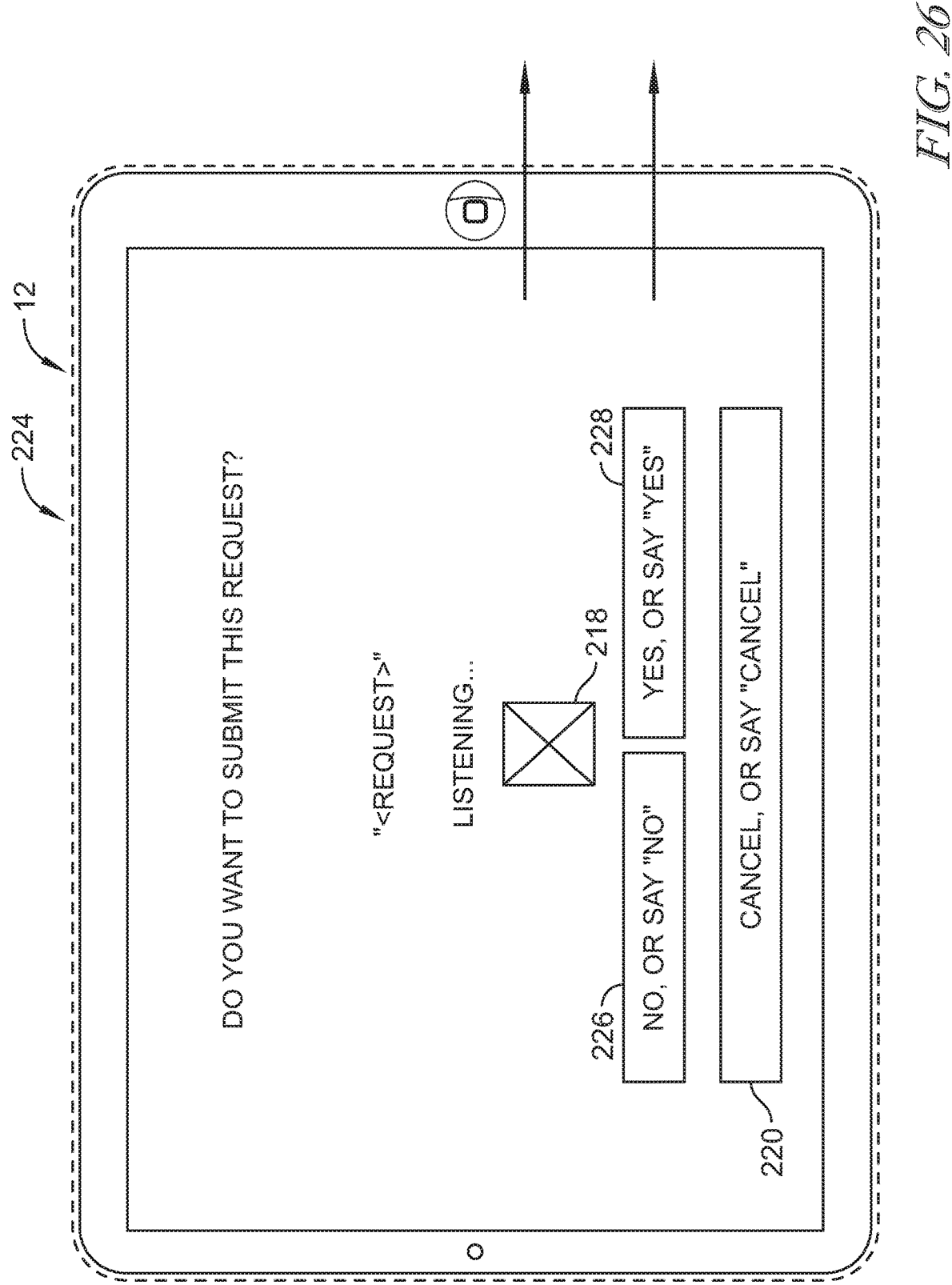
FIG. 26 is a screen shot of a second voice confirmation screen that permits the patient to submit the voice request or cancel the voice request.

After screen 222 appears for a preset amount of time (e.g., ten seconds, twenty seconds, one minute, two minutes, etc.) without the patient canceling the request using button 220 or saying "cancel," then tablet 12 displays a second voice confirmation screen 224 as shown in FIG. 26. Screen 224 includes the text "Do you want to submit this request?" and lists the "<Request>" that the patient verbally entered using tablet 12. Screen 224 also includes the listening icon 218 and cancel, or say "cancel" button 220 that are used in the same manner as described above. Screen 224 further includes a no, or say "no" button 226 and a yes, or say "yes" button 228. Button 226 can be selected by the patient if the patient does not wish to submit the request or the patient can simply say "no." Button 228 can be selected by the patient if the patient does wish to submit the request or the patient can simply say "yes."

Figure 27:
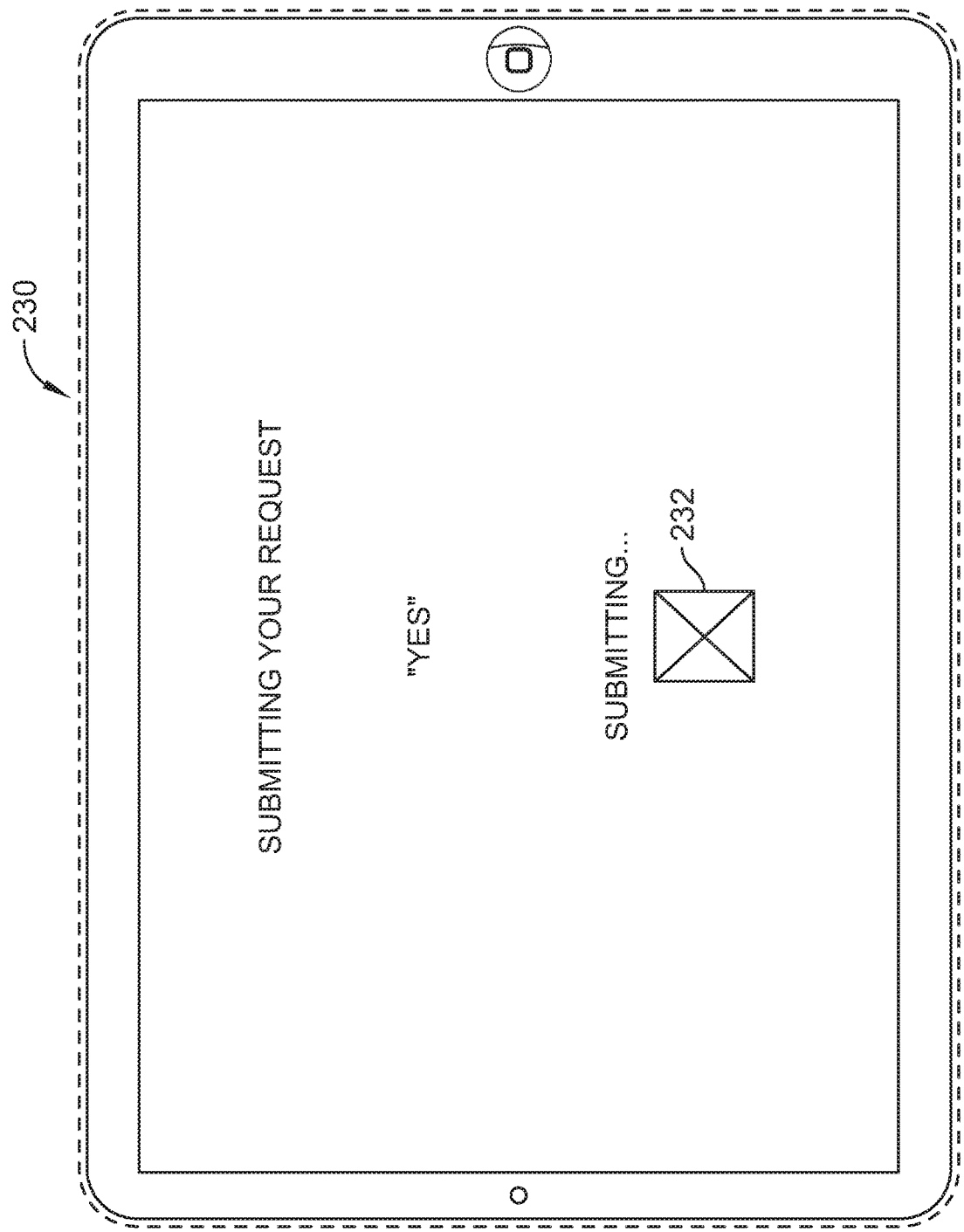
FIG. 27 is a screen shot of a submit voice request screen that appears on the tablet if the patient says "yes" while viewing the second voice request screen of FIG. 26.
Figure 28:
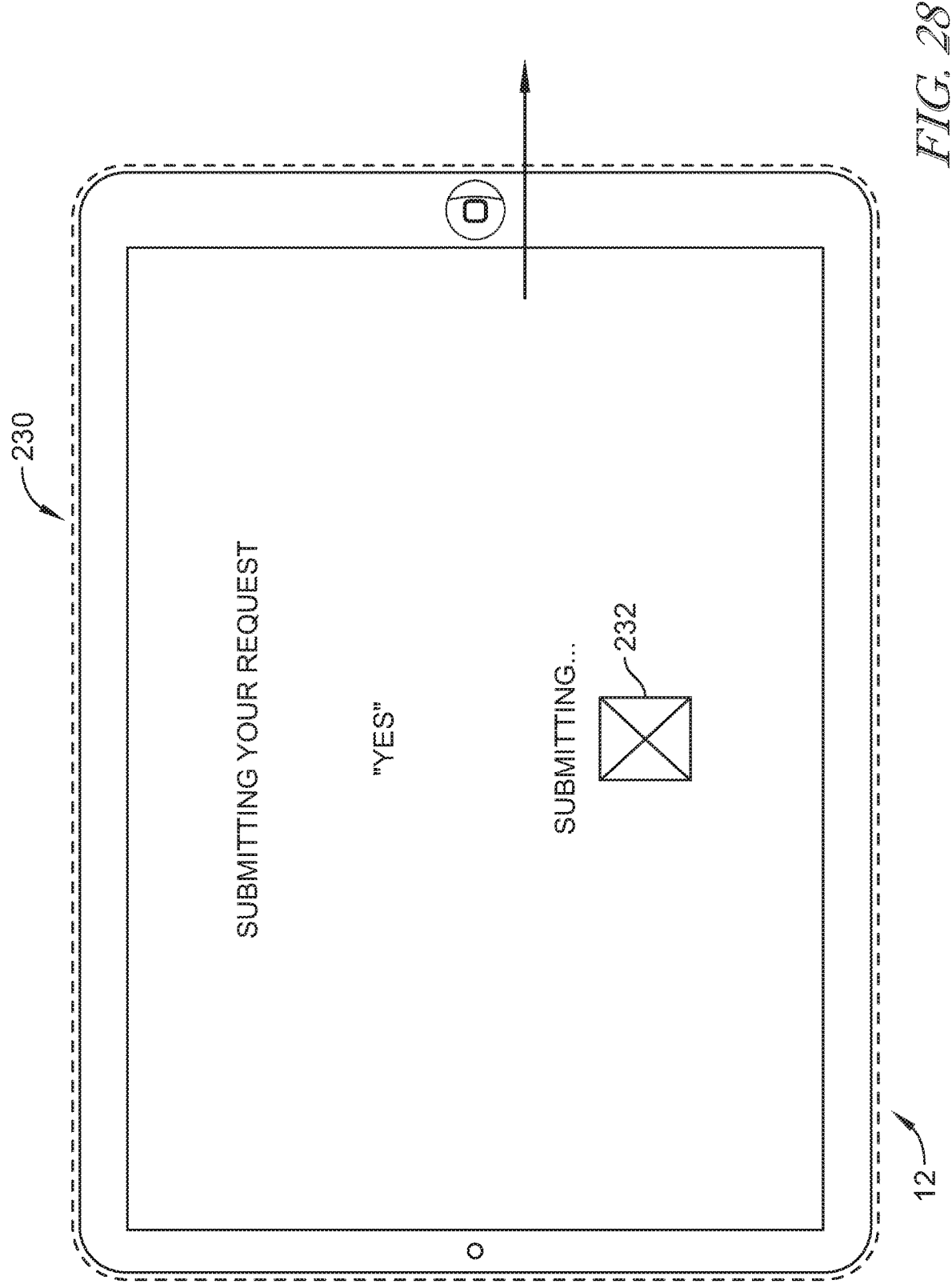
FIG. 28 is a duplicate of FIG. 27.

If the patient selects button 228 or says "yes" while viewing screen 224, then tablet 12 responds by displaying a submit voice request screen 230 as shown in FIG. 27. Screen 230 includes the text "Submitting Your Request" and "Yes" to indicate to the patient that the yes selection or voice entry on screen 224 was successfully made. A submitting icon 232 also appears on screen 230 during the submission process. FIG. 28 is a duplicate of FIG. 27 but is shown on the next drawing sheet for ease of reference.

Figure 29:
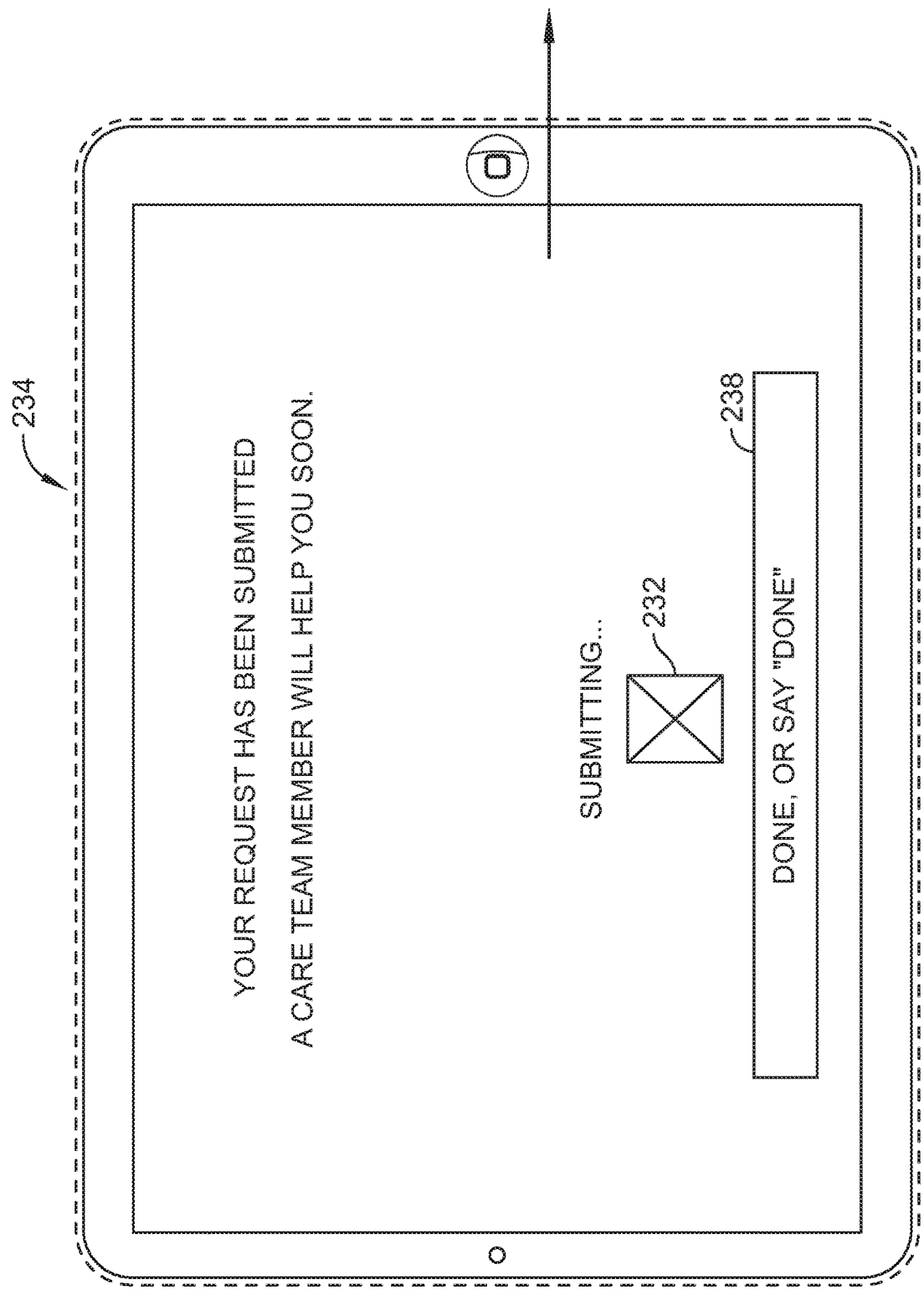
FIG. 29 is a screen shot of a submitted screen indicating that the voice request has been successfully submitted.
Figure 30:
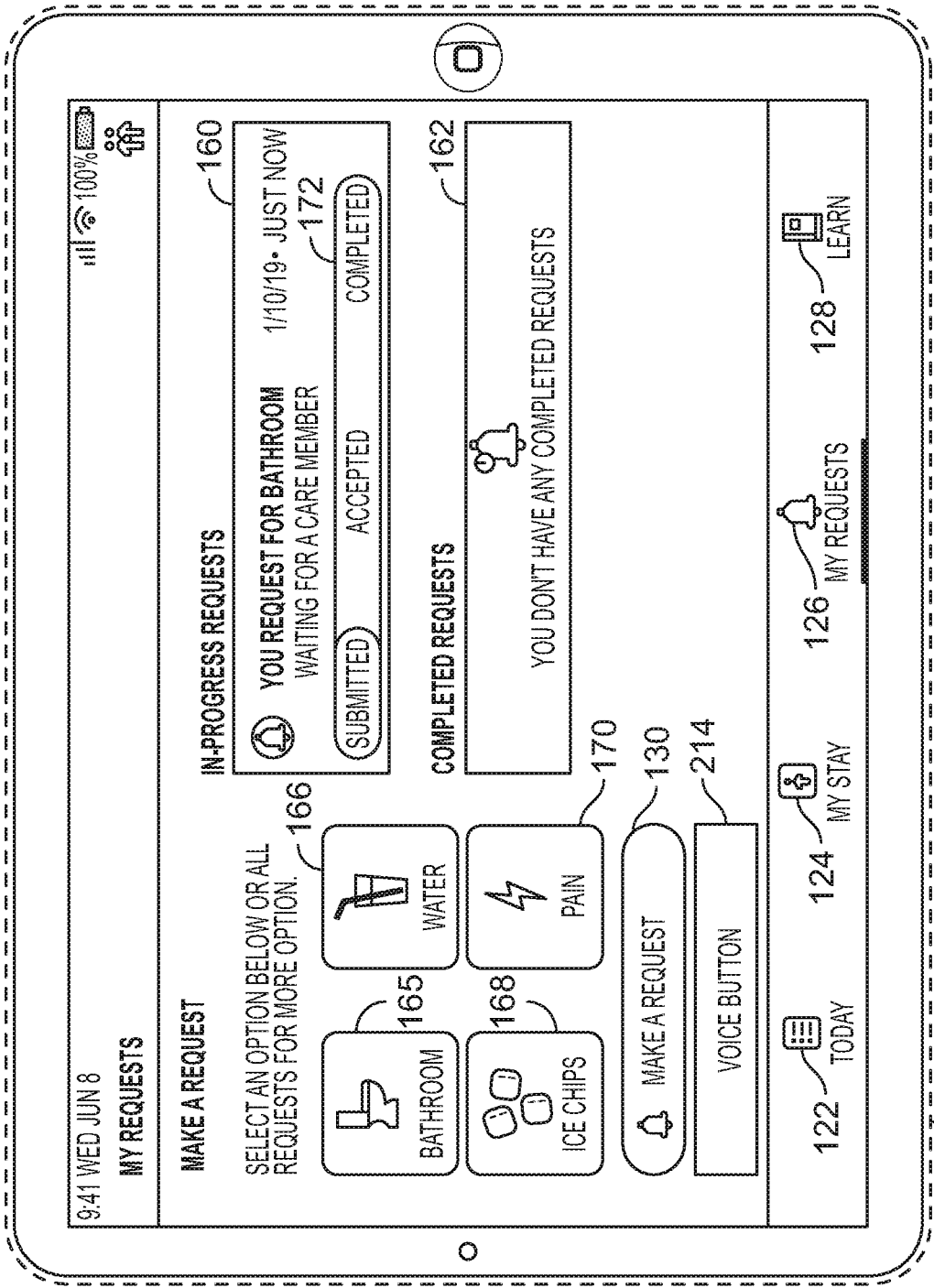
FIG. 30 is a screen shot of an in-progress voice requests screen showing a list of voice requests that have been made by the patient but not yet completed.

After the request submission process is completed at screen 230, tablet 12 displays a submitted screen 234 as shown in FIG. 29. Screen 234 includes the text "Your Request Has Been Submitted" and "A care team member will help you soon." Screen 234 also includes a submitted icon 236 to indicate to the patient that the request has been successfully submitted. Screen 234 further includes a done, or say "done" button 238. The patient can either select button 238 or say "done" and tablet 12 responds with an in-progress voice requests screen 240 as shown in FIG. 30. Screen 240 of FIG. 30 is substantially the same as screen 158 of FIG. 22 and so the same reference numbers are used where appropriate. However, in text box 160 of screen 240, text appears to advise the patient of the in-progress request that was submitted using the voice entry screens of FIGS. 23-29. The progress bar 172 also appears in text box 160 of screen 240 with the word submitted highlighted.

Figure 31:
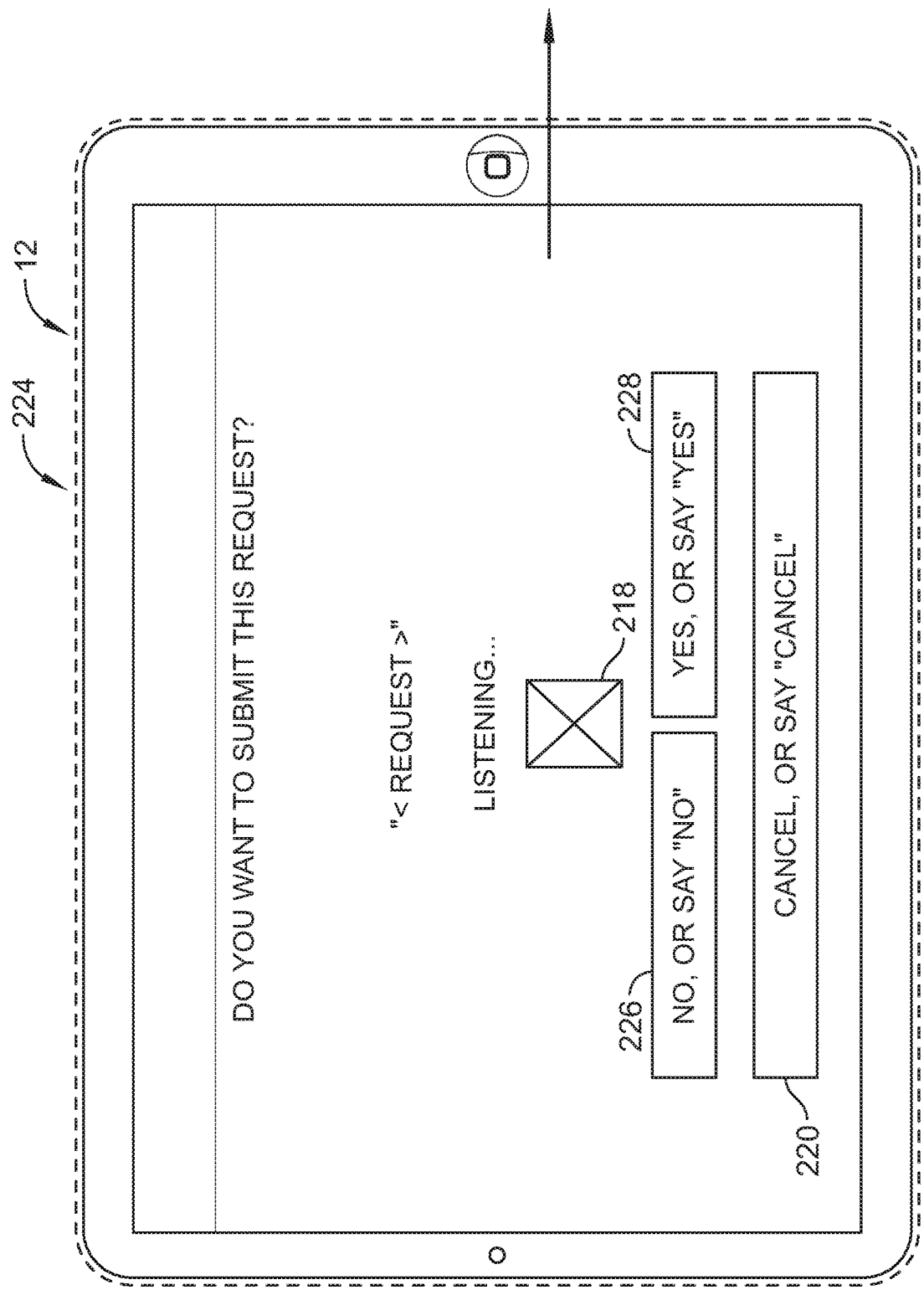
FIG. 31 is a duplicate of FIG. 26.
Figure 32:
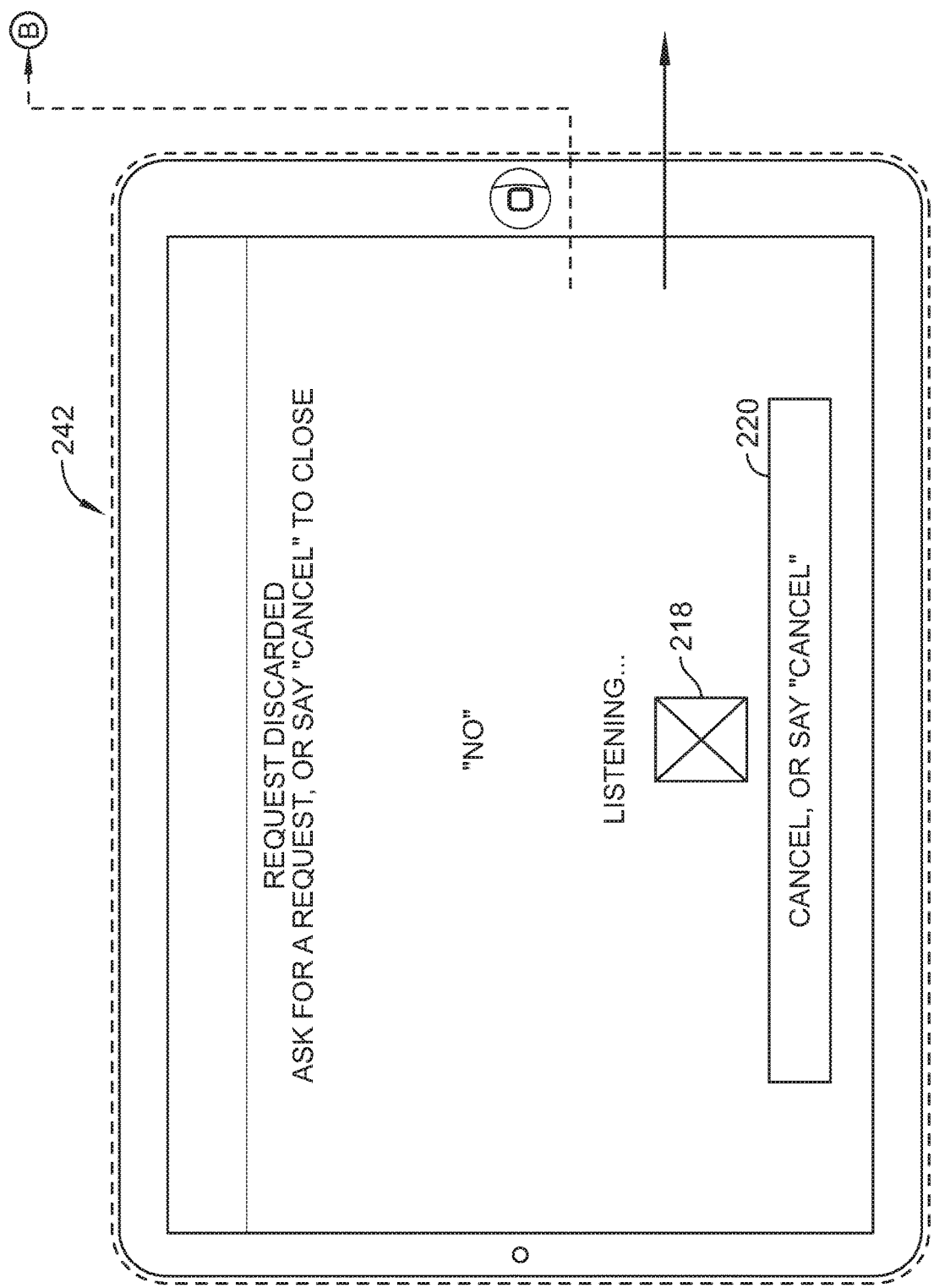
FIG. 32 is a screen shot of a discarded voice request screen that appears on the tablet if the patient says "no" while viewing the second voice request screen of FIG. 26 or FIG. 31.

FIG. 31 is a duplicate of FIG. 26 but is shown on the next drawing sheet for ease of reference. If the patient selects button 226 or says "no" while viewing screen 224, then tablet 12 responds by displaying a discarded voice request screen 242 as shown in FIG. 32. Screen 242 includes the text "Request Discarded" and "Ask for a request, or say 'Cancel' to close." Screen 242 also displays the text "No" to indicate to the patient that the no selection or voice entry on screen 224 was successfully made.

Figure 33:
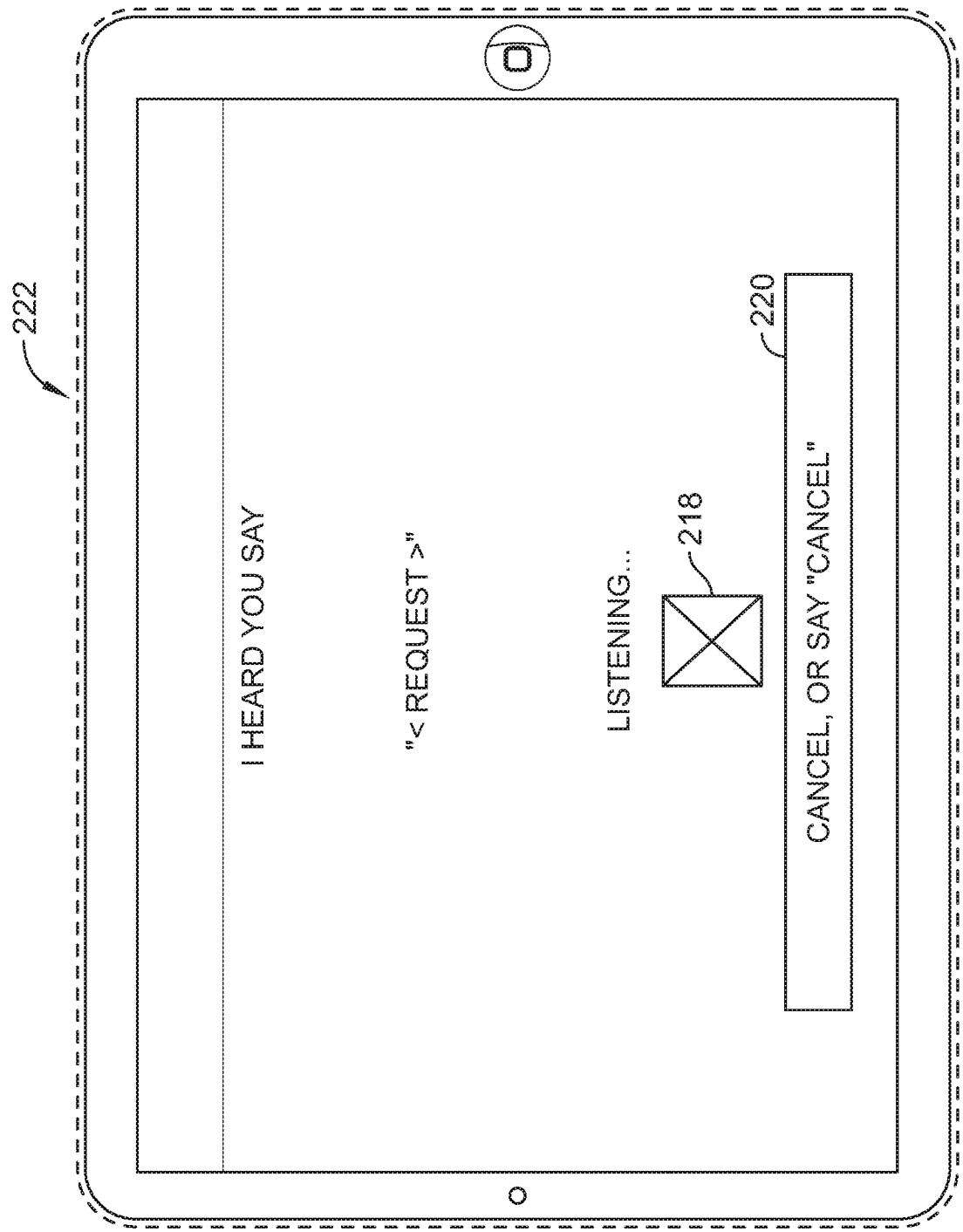
FIG. 33 is a screen shot of a new request screen that appears on the tablet if the patient makes a new request while viewing the discarded voice request screen of FIG. 32.
Figure 34:
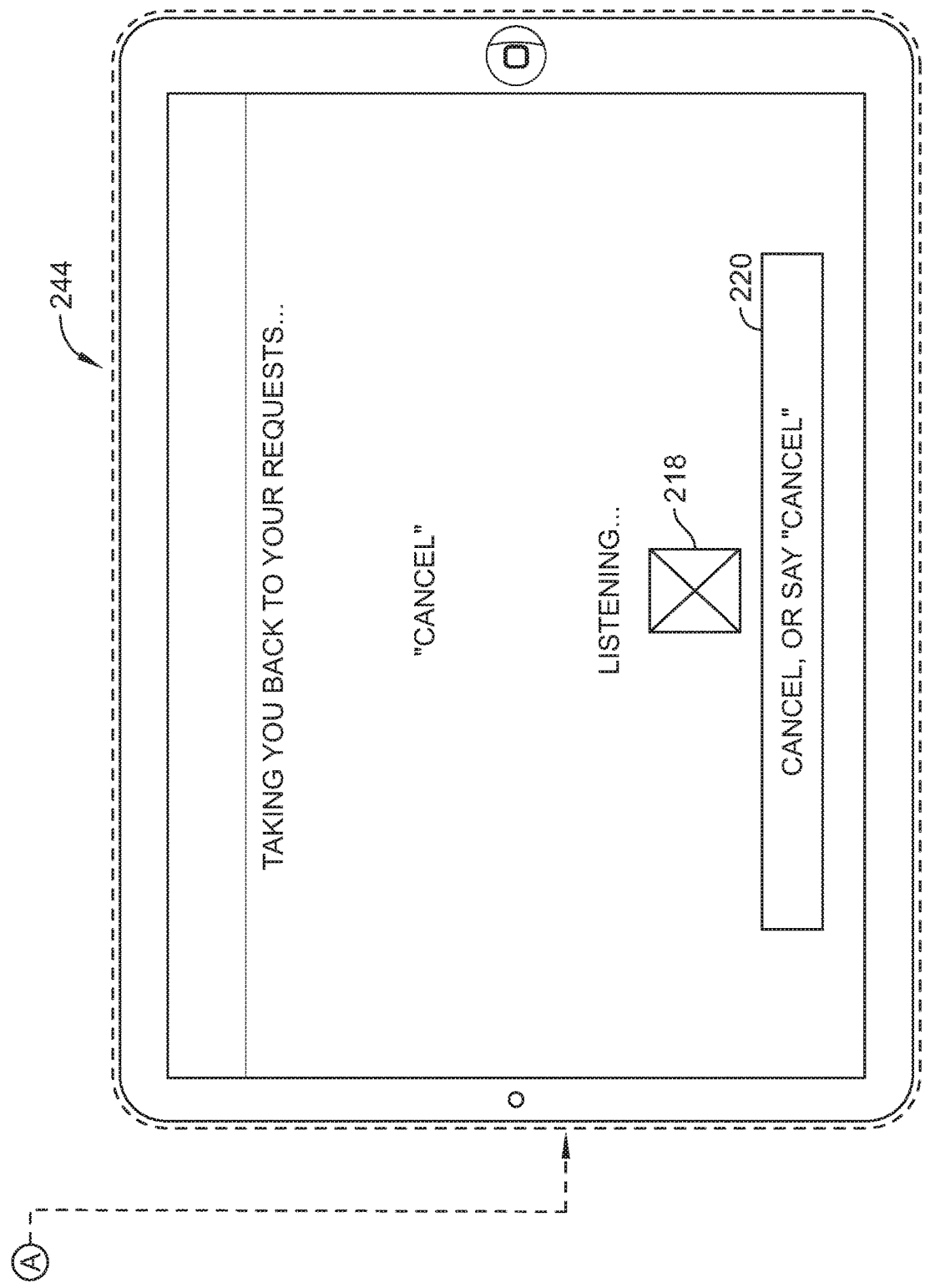
FIG. 34 is a screen shot of a cancel screen that appears on the tablet if the patient cancels the request.

If the patient says a new request while viewing screen 242, then tablet 12 responds by displaying a new request screen 222' which is the same as screen 222 of FIG. 25 discussed above. If the patient navigates to screen 222' from screen 242 of FIG. 32, then the patient is able to proceed as discussed above in connection with FIGS. 25-30. If the patient selects button 220 on screen 222' of FIG. 33 or says cancel while viewing screen 222', then tablet 12 responds by displaying a cancel screen as shown in FIG. 34. Screen 244 includes the text "Taking you back to your requests . . . " and "Cancel" to indicate to the patient that the patient has successfully canceled the request while viewing screen 242 of FIG. 32. After the canceling process is complete, tablet 12 returns to the my requests screen 158 of FIG. 22.

Figure 35:
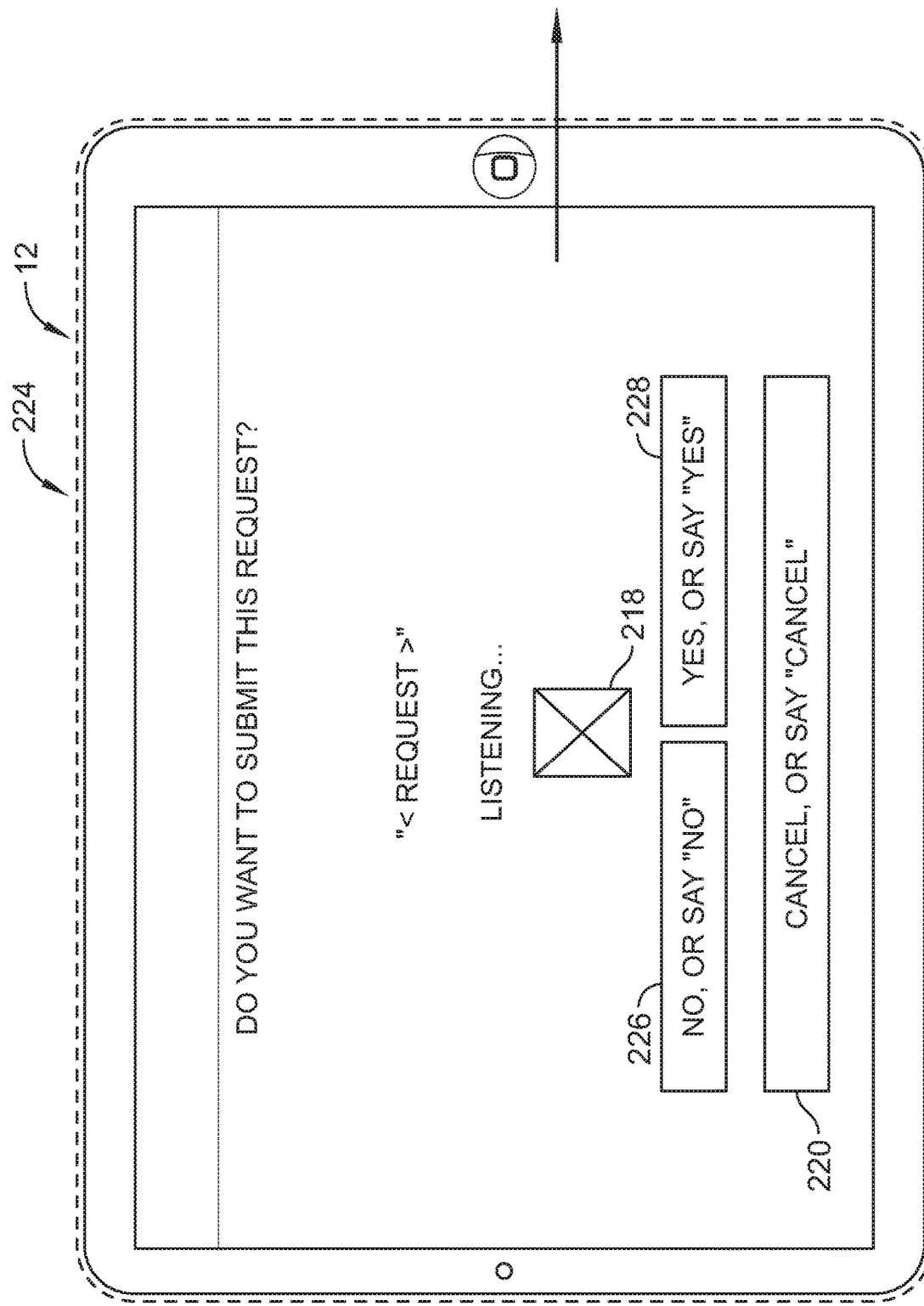
FIG. 35 is a duplicate of FIGS. 26 and 31.
Figure 36:
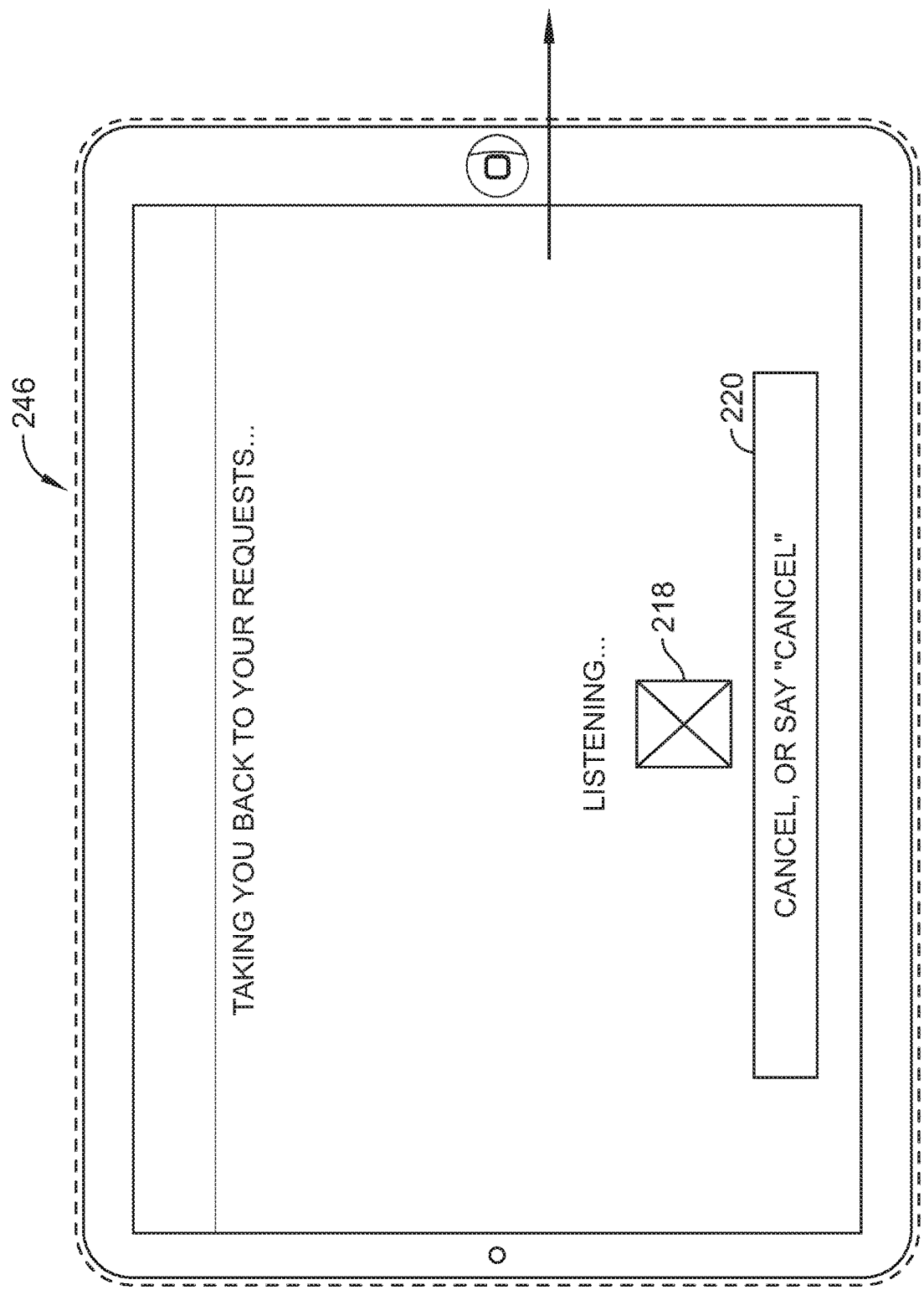
FIG. 36 is a screen shot of a time out redirect screen that appears on the tablet prior to the tablet returning to the my request screen.
Figure 37:
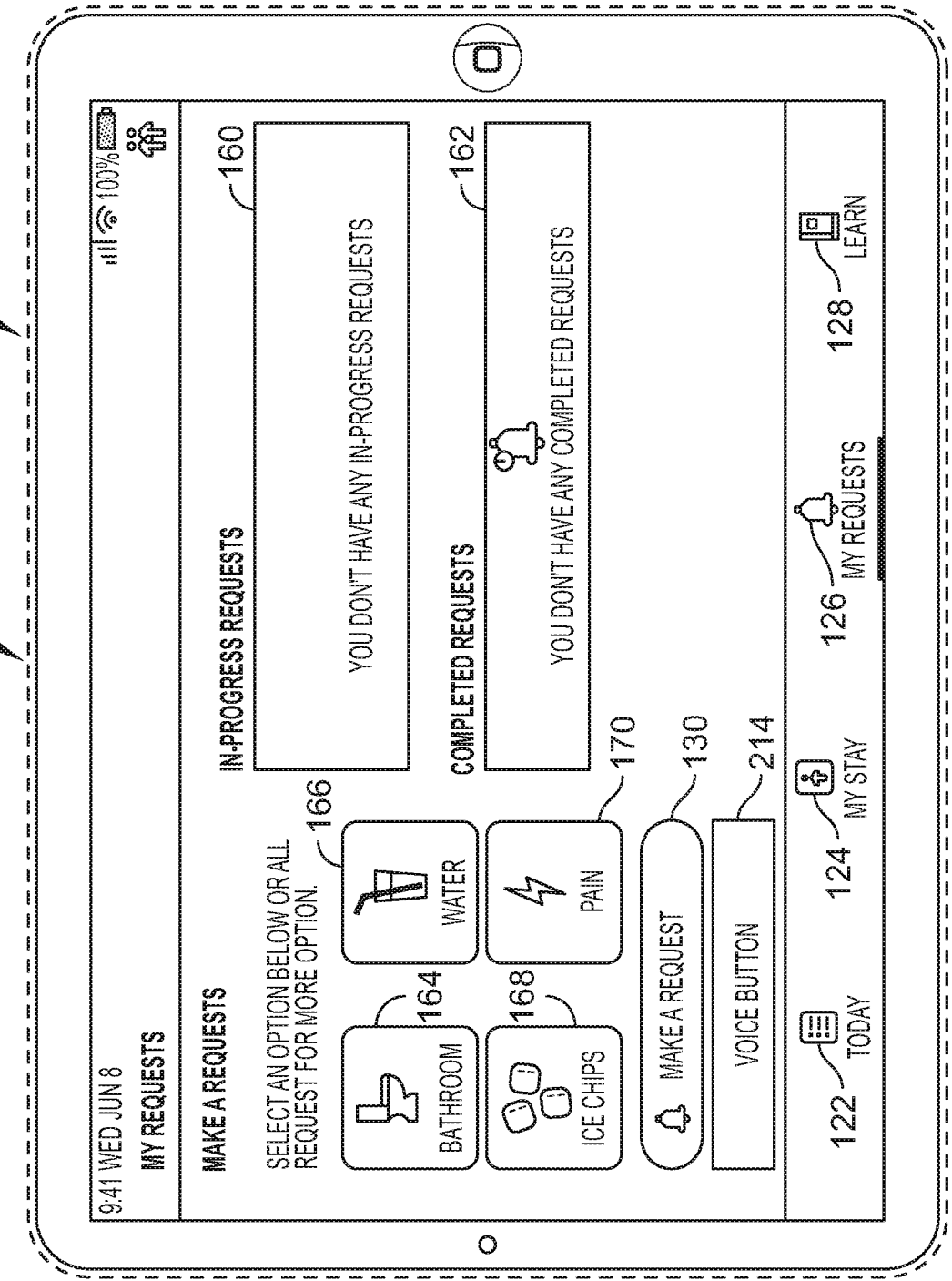
FIG. 37 is a screen shot of the my requests screen to which the tablet returns after the time out redirect screen of FIG. 36.

FIG. 35 is a duplicate of FIGS. 26 and 31 but is shown on the next drawing sheet for ease of reference. If for a predetermined period of time (e.g., two minutes, five minutes, etc.) the patient does not select any of buttons 220, 226, 228 while viewing screen 224, or if the patient does not say cancel, no, or yes within the predetermined period of time, then tablet 12 responds by displaying a time out redirect screen as shown in FIG. 36. Screen 246 includes the text "Taking you back to your requests . . . " After screen 246 is displayed for a short period of time (e.g., five seconds, ten seconds, etc.), tablet 12 once again displays the my requests screen 158 as shown in FIG. 37. FIG. 37 is a duplicate of FIG. 22 and so the same reference numbers are used.

Figure 38:
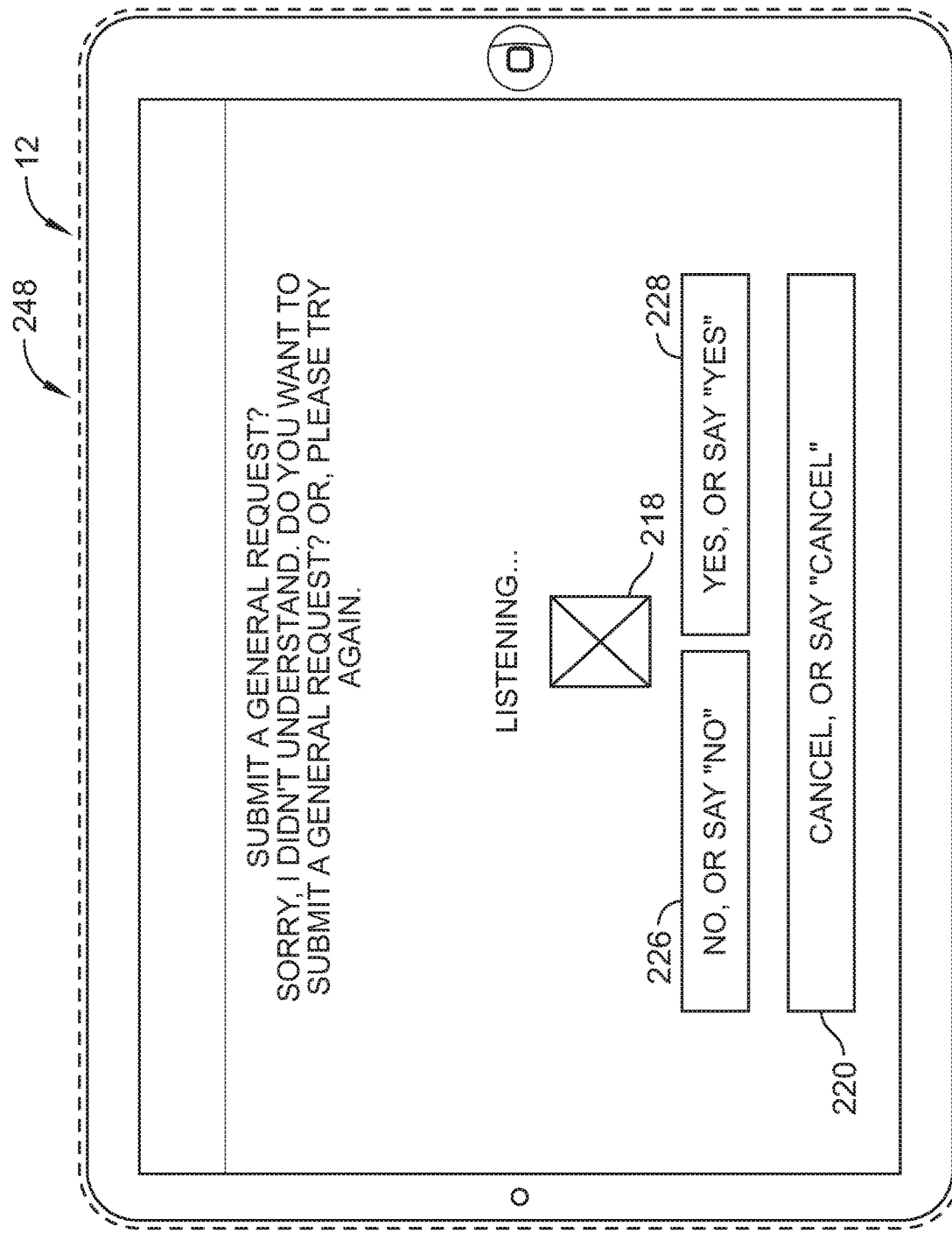
FIG. 38 is a screen shot of a general request screen that appears on the tablet if the voice request is not understood.

Referring now to FIG. 38, an example of a general request screen 248 is shown and includes text that appears on the display screen of tablet 12 if the request spoken by the patient is not recognized or understood by tablet 12. In particular, the screen 248 includes the following text: "Submit a general request? Sorry, I didn't understand. Do you want to submit a general request? Or, please try again." While viewing screen 248, the patient can select the no button 226 or cancel button 220, or say no or cancel, to notify the tablet 12 that the patient does not wish to submit a general request. Alternatively, the patient can select the yes button 228 or say yes to submit a general request from tablet 12 in system 10.

Figure 39:
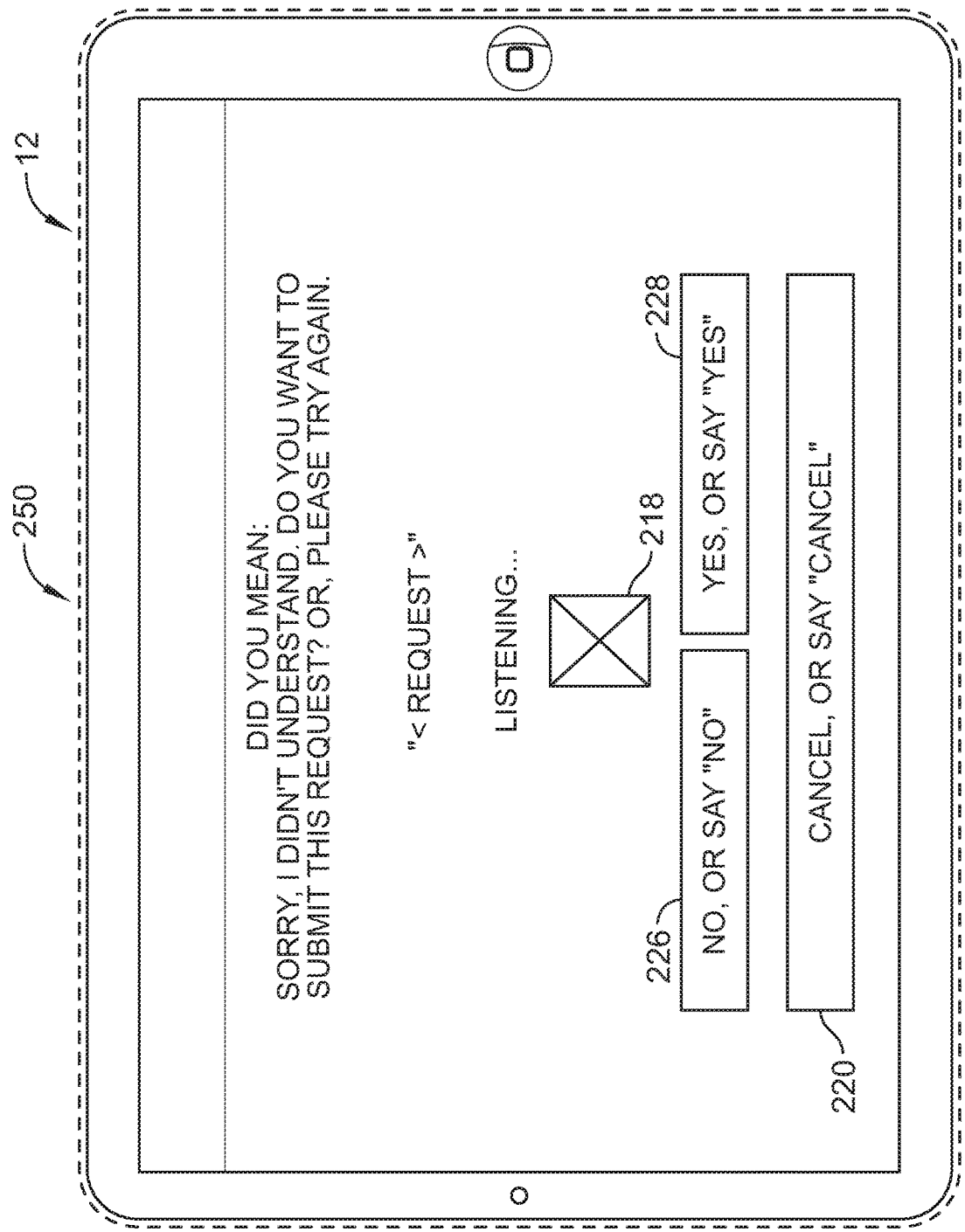
FIG. 39 is a screen shot of a clarification screen that appears on the tablet if the voice request needs to be clarified.

If the request spoken by the patient is similar enough to a patient request that is recognized by tablet 12, then tablet 12 displays a clarification screen 250 as shown in FIG. 39. Screen 39 displays the following text: "Did you mean: Sorry, I didn't understand. Do you want to submit this request? Or, please try again" and then the request that the tablet 12 concludes is close to what was spoken by the patient is displayed. FIG. 39 illustratively uses the place holder text, "<Request>" for the request that the patient is believed to have intended, but in use a recognized request such as bathroom, ice chips, blanket, etc. appears on screen 250 in lieu of the illustrative place holder text. While viewing screen 250, the patient can select the no button 226 or cancel button 220, or say no or cancel, to notify the tablet 12 that the patient does not wish to submit the request appearing on screen 250. Alternatively, the patient can select the yes button 228 or say yes to submit the request shown on screen 250.

Figure 40:
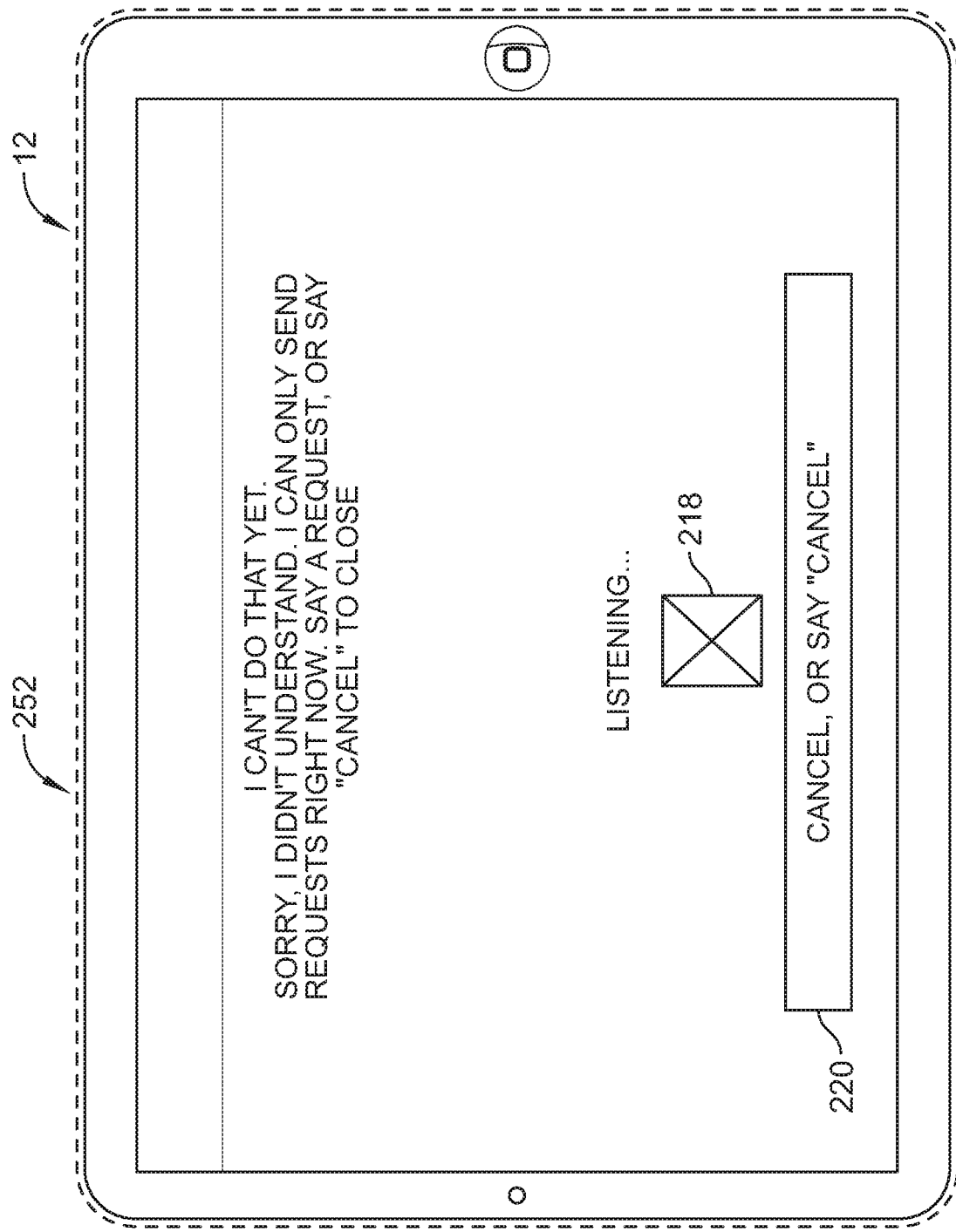
FIG. 40 is a screen shot of a no match screen that appears on the tablet if there is no match for the voice request being made by the patient.

If the patient makes multiple attempts (e.g., two attempts, three attempts, etc.) at speaking a request into tablet 12 and none of the attempts match a request recognized by tablet 12, then a no match screen 252 is displayed on tablet 12 as shown in FIG. 40. Screen 252 of FIG. 40 includes the following text: "I can't do that yet. Sorry, I didn't understand. I can only send requests right now. Say a request, or say 'Cancel' to close." The patient then has the option of making another attempt at saying a request or the patient can cancel by selecting button 220 or saying cancel.

Based on the foregoing, it will be appreciated that the patient engagement software implemented on tablet 12 as well as system 10, in general, are a practical application of a patient request system and method. The patient engagement software permits patients to make specific requests which increases caregiver productivity by eliminating extra time communicating with patients to obtain more information about the requests being made. The patient engagement software also increases patient satisfaction due to requests being responded to more quickly by caregivers and by providing status information regarding the progress of the patient requests being fulfilled.

Hospitals are required to address patient satisfaction issues to meet Centers for Medicaid/Medicare Services (CMS) requirements. Thus, system 10 and the patient engagement software implemented on tablet 12 also serve as a practical application in assuring Medicaid/Medicare reimbursement rates are not decreased due to low patient satisfaction scores. The patient engagement software of tablet 12 enhances patient experience and satisfaction by providing the patient with a sense of control over their care, visibility to their care, reminders about health tasks, education, etc. System 10 operates as a practical application by giving patients the opportunity to become involved in steps that contribute to reducing their length of stay in a healthcare facility.

It is contemplated that the patient request system 10 is configured to provide patient requests to caregiver mobile devices equipped with the LINQ™ mobile application or similar such software developed under the VOALTE™ platform, each of the LINQ™ and VOALTE™ software being available from Hill-Rom Company, Inc. of Batesville, Ind. Additional details of the mobile applications for providing alerts to mobile devices of caregivers in healthcare facilities can be found in U.S. Patent Application Publication No. 2019/0108908 A1, which is hereby incorporated by reference herein in its entirety. The present disclosure contemplates that patient requests are displayed on caregiver mobile devices in a manner substantially similar to the manner in which alerts are displayed on mobile devices as shown in U.S. Patent Application Publication No. 2019/0108908 A1.

Referring once again to FIG. 1, the patient engagement software (aka the patient engagement application or the iOS application or just the application) has two primary forms of configuration. The first is a minimal operational configuration from the Mobile Device Management (MDM) system 16. The second is a clinical and operational information configuration from the Content Management Solution (CMS) 18. The MDM 16 houses configuration related to the host and port on which the application at a customer site needs to connect in addition to customer identifying information needed to access the CMS 18. Without this information, the application does not have enough information to support user authentication or retrieve information needed by a patient.

The CMS 18 contains clinical and operational information specific to a particular customer. While the CMS 18 contains information for multiple customers, the information is organized in a manner that allows the use of MDM provided data to access the relevant subset of information relevant to a patient. This patient information includes the HIPAA usage agreement presented during login, the available request types associated his nursing unit, the URL for weather information, Twitter feed information, and the URL for educational content.

Figure 41:
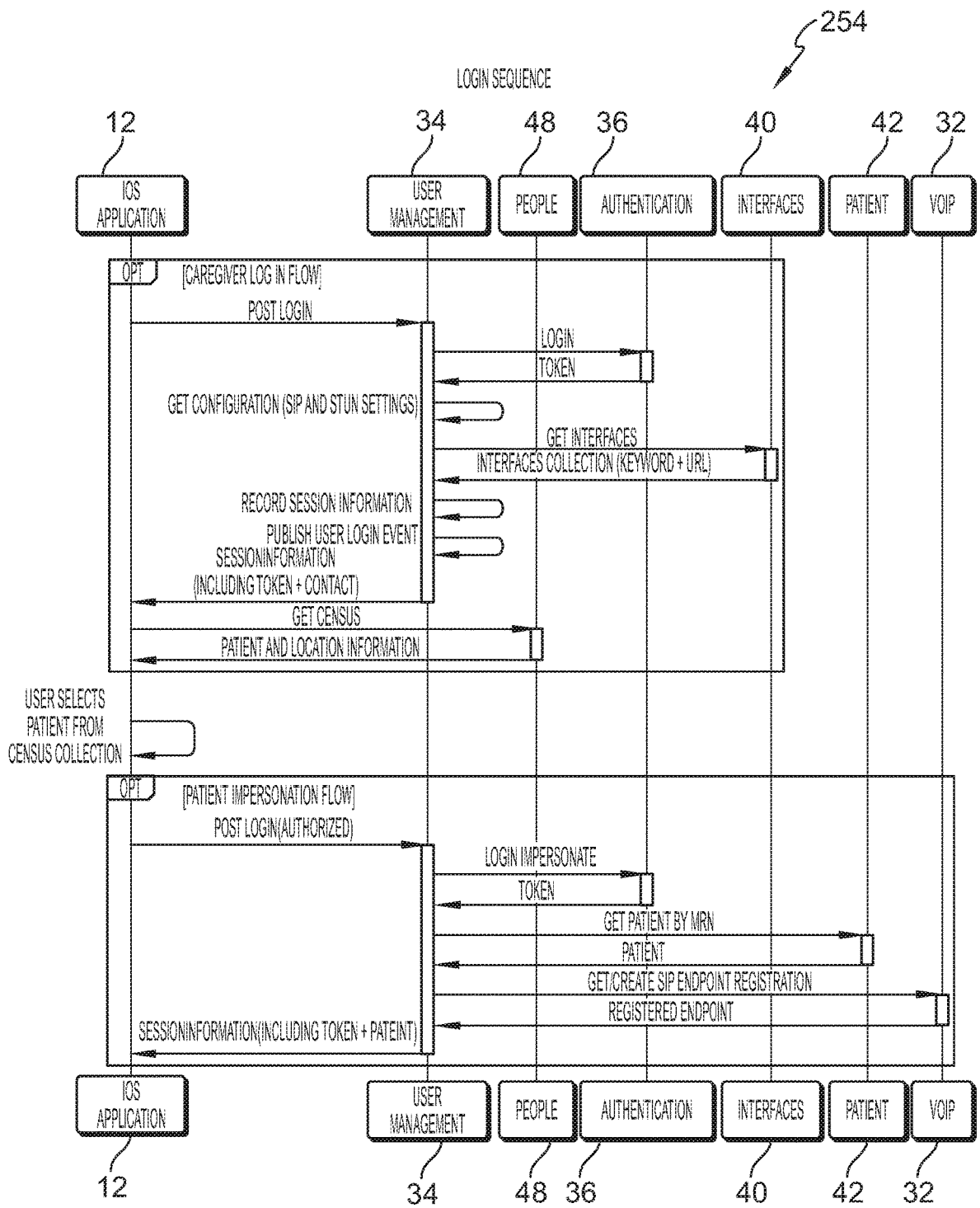
FIG. 41 is a flow diagram of a login sequence implemented by the patient request system of FIG. 1.

Because the end user of the patient engagement application lacks the credentials typically associated with a secured application, an alternative authentication model or login sequence 254 is used. This alternative authentication model 254 is shown diagrammatically in FIG. 41. In FIG. 41, reference number 12 is used for the iOS application block since that block represents the patient engagement application of the respective tablet 12. FIG. 41 shows the interaction that occurs between the application 12 and modules 32, 34, 36, 40, 42, 48, which as shown in FIG. 1, involves the use of server 14.

The login sequence or model 254 takes advantage of care team network user credentials to initiate a session through patient impersonation. As illustrated in FIG. 41, there are two phases for authentication before a patient can use the application 12. The first involves the use of a caregiver's network credentials to perform initial authentication indicated by the heading [Caregiver login flow] in FIG. 41. Once authenticated, the caregiver selects a patient from a provided list in order to perform patient authentication as indicated by the heading [Patient impersonation flow] in FIG. 41.

After the second phase of authentication is complete, the patient can continue to use the application 12 until his session is explicitly ended by a caregiver, the device runs out of power causing it to lose session information, or the application is explicitly closed (up-swipe in iOS). Because there is a desire to keep a patient logged into the application 12, there is no logout control available to the user. Instead, a caregiver must use her login credentials to initiate a patient logout. The flow is the same as the [Caregiver login flow] illustrated above. The only additional step includes a logout request in the application 12.

A patient can initiate a request for help or assistance via an alert as discussed above. The alert (aka patient request) is transmitted to nurse call equipment and mobile care devices in and around a nursing unit as a means to advertise a patient's need. Once satisfied, the alert is cancelled. During the lifecycle of the alert, the patient is provided with an indication of progress on tablet 12 as also discussed above. Much like an order on Amazon or other online retailing site, the alert is shown via the patient engagement application on tablet 12 as created, in progress, and completed.

Figure 42:
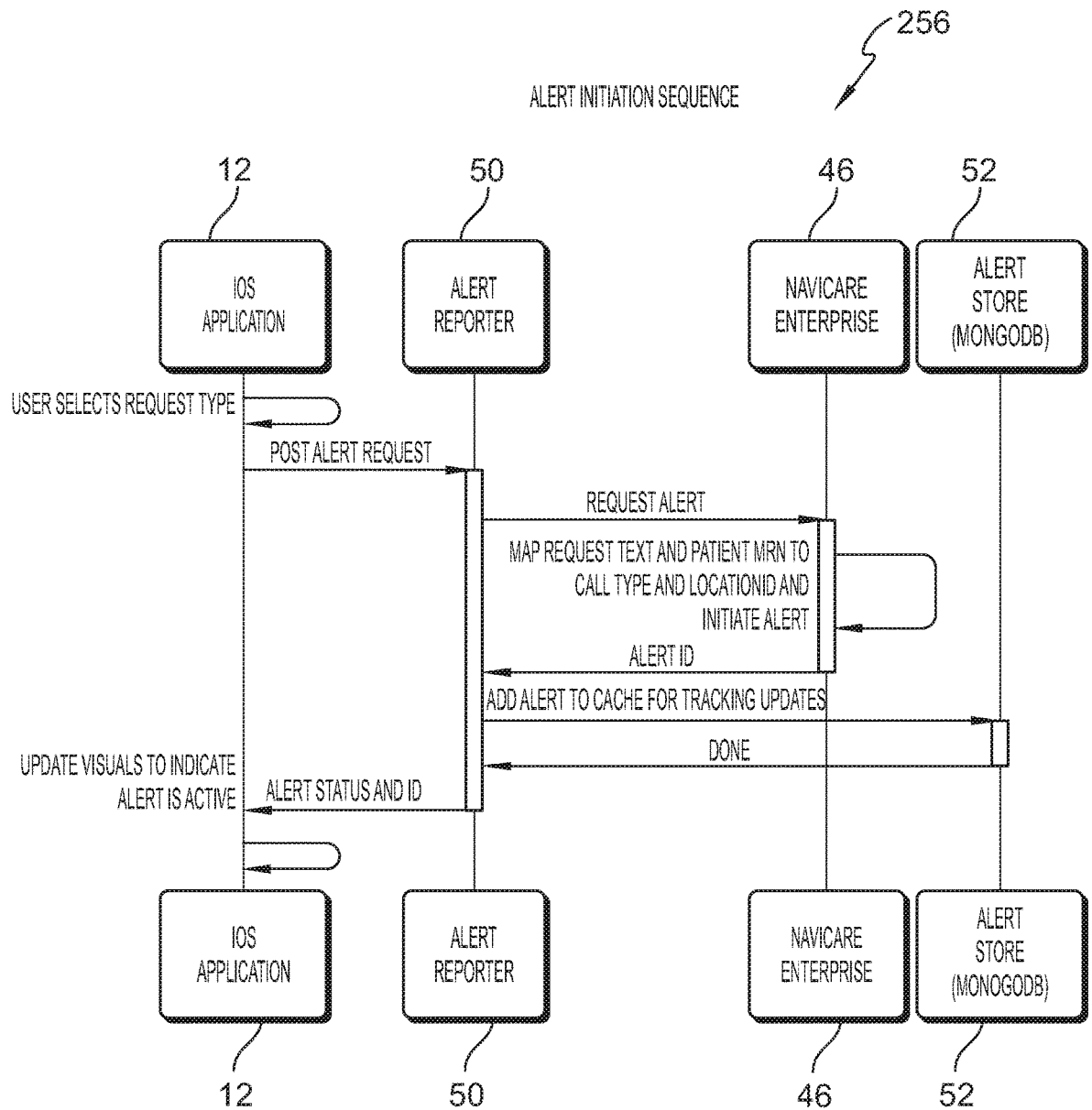
FIG. 42 is a flow diagram of an alert initiation sequence implemented by the patient request system of FIG. 1.

When a patients initiates a request, it is sent to the NaviCare Enterprise server 46 to be fulfilled. An alert initiation sequence 256 is shown diagrammatically in FIG. 42. FIG. 42 shows the interaction that occurs between the application 12 and alert reporter module 50, the NaviCare Enterprise server 46, and the alert store database 52, which involves the use of server 14 as shown in FIG. 1. Elements related to nurse call devices and notification procedure processing are not included as they are internal to the behavior of the NaviCare Enterprise environment which is a pre-existing nurse call system available from Hill-Rom Company, Inc. of Batesville, Ind. as noted above. Information in the Alert Store database 52 provides referential information associated with the original POST (aka patient request). Specifically, a mapping between the NaviCare CallGUID and the networkId of the user in the POST. The networkId is needed because it is used by the Push service 30 during alert status updates to map to the APNS tokens 26.

Figure 43:
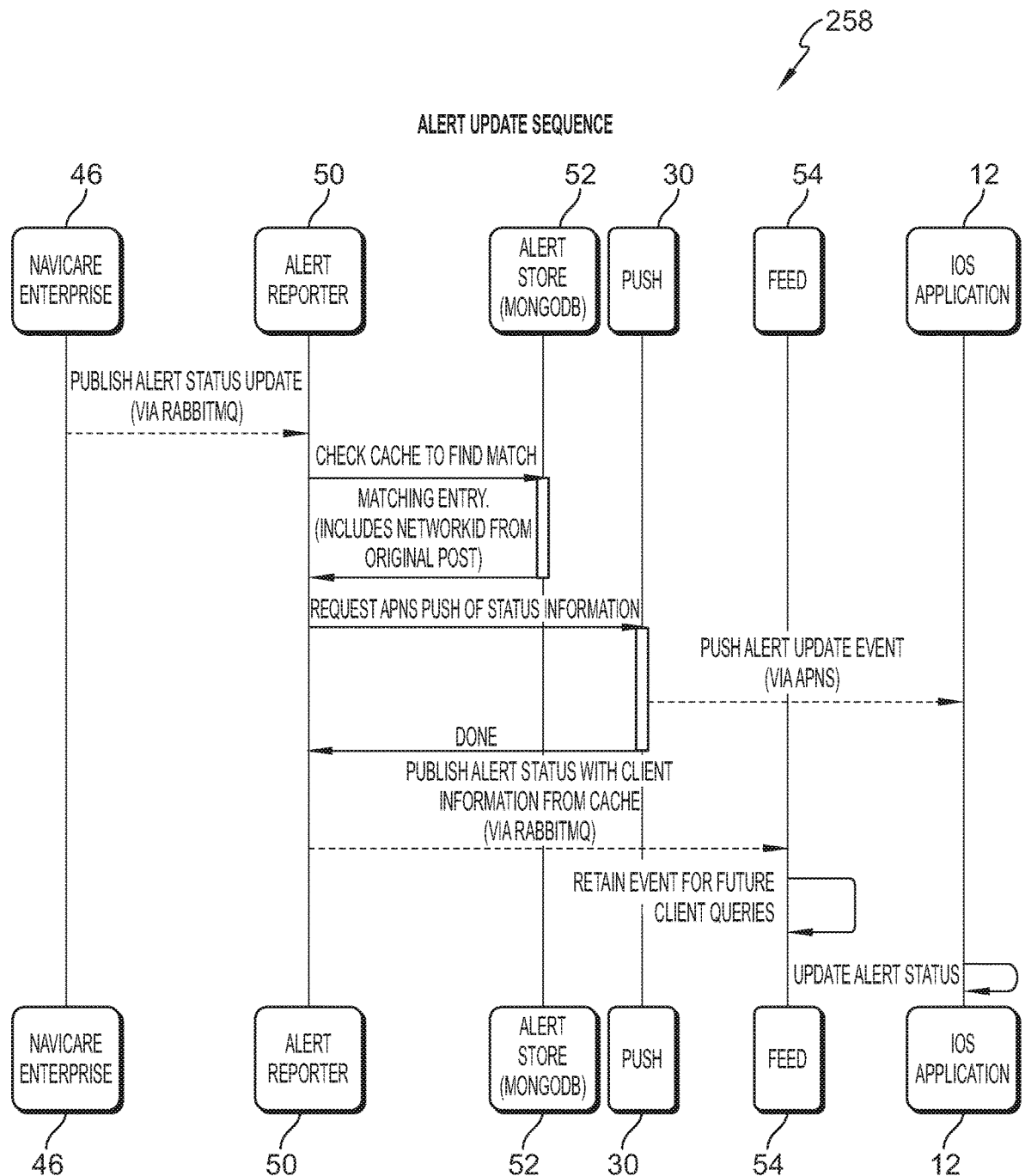
FIG. 43 is a flow diagram of an alert update sequence implemented by the patient request system of FIG. 1.

Status updates are initiated from within the NaviCare Enterprise environment. The status updates may be triggered by mobile device events like a caregiver "Accept" or opened audio session to an audio station of the nurse call system located in the patient's room or to the tablet 12. Alternatively, the status updates may be triggered in NaviCare Nurse Call by placing the request on the Wait List or performing an explicit call cancellation. The Push notification processing of the status updates depends on network login registration during authentication. In any event, FIG. 43 shows an alert update sequence 258 as contemplated by the present application. In the illustrative alert update sequence 258, Feed module 54 is a passive participant in this flow. Feed module 54 is shown diagrammatically in FIG. 43 because it is useful to know that the Feed module 54 receives a revised/embellished alert event rather than utilizing the raw alert event from the NaviCare nurse call system.

In addition to alerts, the present disclosure contemplates that voice communication is provided from a caregiver to a patient. In some embodiments of system 10, voice communication is only supported in response to an alert (aka patient request). However, in other embodiments, voice communication is able to be initiated from the caregiver to the patient (e.g., the patient's tablet 12 or an audio station in the room) at all times at the discretion of the caregiver. In any event, the processing flow associated with establishing voice communication is the same in all cases. In other embodiments, video communication from caregivers to patients using tablets 12 is also provided for in system 10. Video conferencing for purposes of telemedicine is also contemplated for some embodiments of system 10 and tablet 12. Thus, tablets 12 assigned to patients for at-home use is within the scope of the present disclosure.

Events are initiated from multiple sources within system 10 as noted above. A subset of these events are relevant to a patient and are to be communicated to the patient's tablet 12. The Information Feed 54 acts as a repository of historical event information for a tablet 12. These events include changes to alert status, care team assignment, audio call events, twitter feed updates, and weather updates. Within the feed, there are two primary processing models; event processing, and periodic polling. For those sources that are incapable of generating an event, a poll model is employed in order to obtain updates.

Figure 44:
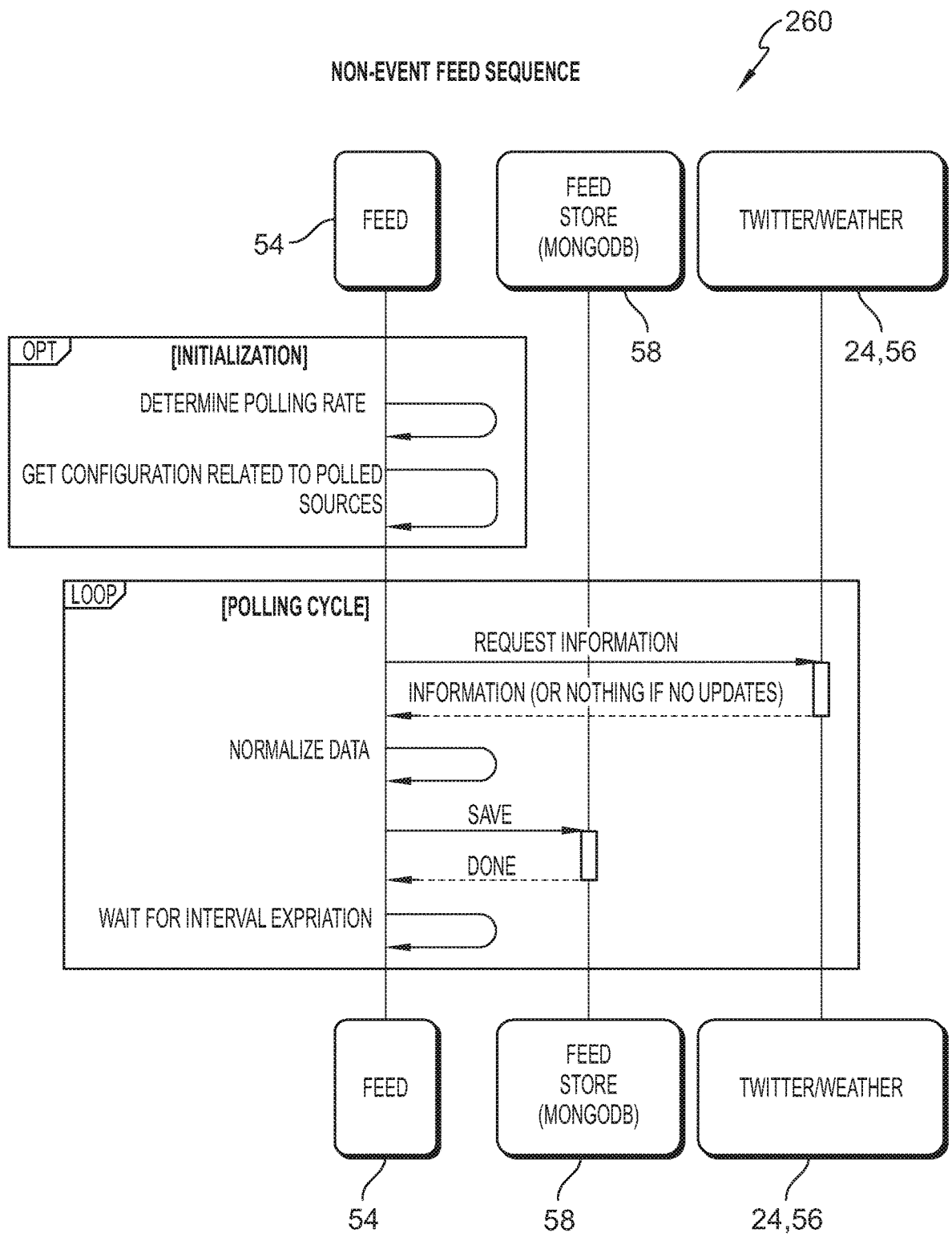
FIG. 44 is a flow diagram of a non-event feed sequence implemented by the patient request system of FIG. 1.

To prevent unending growth in the archived feed collection, the oldest feed content is periodically flushed. The flush rate is configurable at deployment time of system 10. Some feed sources do not, or are incapable of, initiating an event. In these cases, a polled model is employed to gather information that is added to the feed store 54. Examples of these include the Twitter feed 56 and the weather feed 24. An example of a non-event feed sequence 260 pertaining to the weather and Twitter feeds 24, 56 is shown diagrammatically in FIG. 44.

Figure 45:
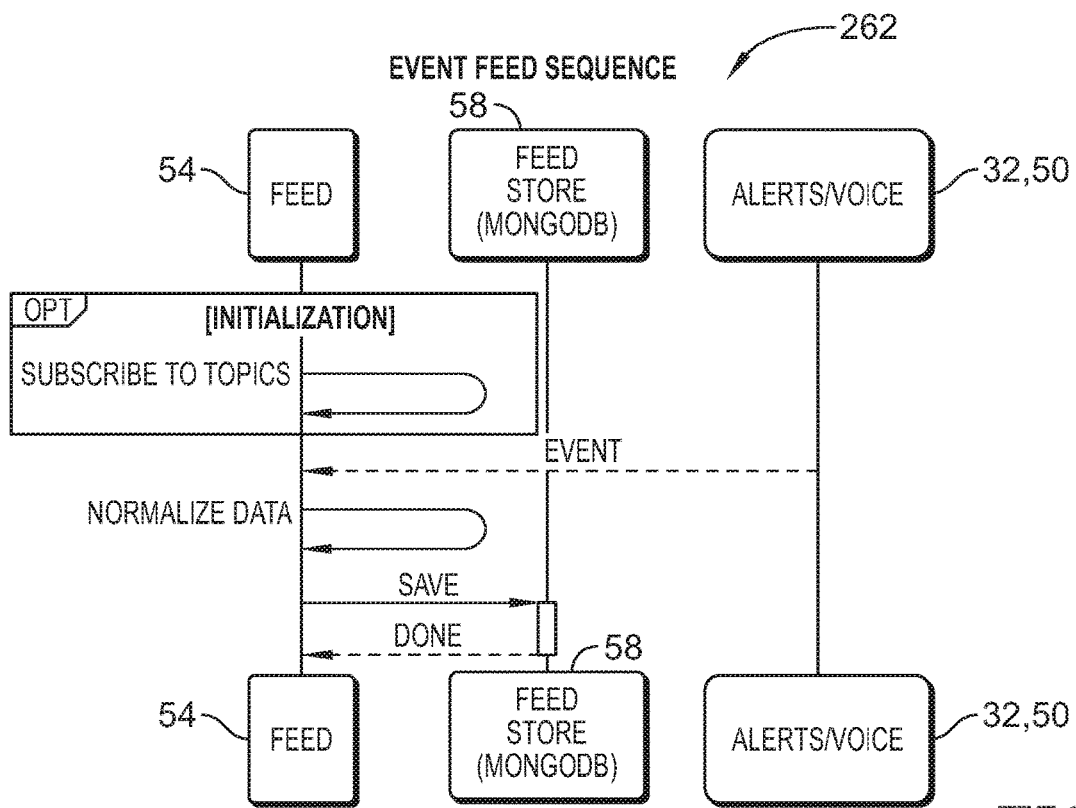
FIG. 45 is a flow diagram of an event feed sequence implemented by the patient request system of FIG. 1.

In the illustrative embodiment of system 10, the Feed module 54 is a subscriber to the RabbitMQ event bus 60. When events arrive at bus 60 from subscribed topics, information associated with the topics are written into the feed store 58. Examples of event-based feeds include alerting and voice call status. An example of an event feed sequence 262 pertaining to the alerts and voice feeds from modules 32, 50 is shown diagrammatically in FIG. 45.

Figure 46:
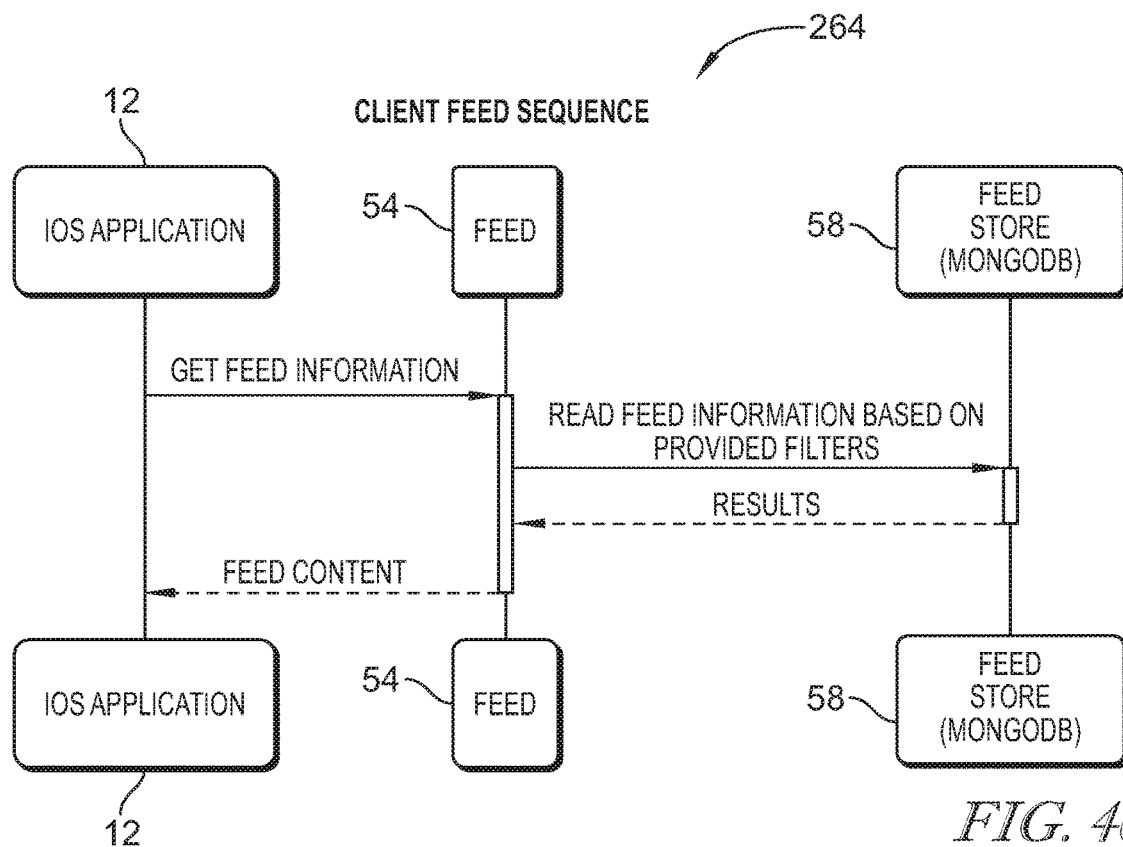
FIG. 46 is a flow diagram of a client feed sequence implemented by the patient request system of FIG. 1.

Outside the process of updating and maintaining the feed store 58, the application 12 RESTfully accesses the feed module 54 in order to obtain content to display to a patient. An example of such a client feed sequence 264 is shown diagrammatically in FIG. 46. Furthermore, educational content is obtained via HealthWise 20 as noted above. In some embodiments of system 10, educational content takes the form of a queryable index of educational items. Once selected, an education item is displayed on the patient's tablet 12.

In some contemplated embodiments of system 10, real-time updates of staff and caregiver visits to the hospital room of patients is displayed on respective tablets 12 via integration of a real time locating system (RTLS) into system 10. The RTLS will provide locating events as feeds to the patient engagement application of tablets 12 in response to individual staff members or caregivers entering the patient's room. The caregivers or staff members entering the room, if desired, may use the notes feature of the patient's tablet or their own mobile devices to append additional information to the RTLS event so that the patient has a clear understanding of who visited them and when, as well as why they were visited.

In some embodiments of system 10, analytics are performed on one or more servers to provide authorized personnel of the healthcare facility with detailed reporting about the types of patient requests submitted, the patterns of usage and needs within specific hospital units, and staffing response times. Based on the analytics, the screens of tablet 12 are customized based on facility data or based on the patient's individual usage and behavior data. For example, the quick request portion (see icons 164, 166, 168, 170 of screen 158 of FIG. 16) displayed on tablet 12 has a pre-set common group of requests when the tablet is initially assigned to the patient. However, if the patient's most commonly requested items differ from the pre-set list, then the quick request group of icons is updated to those corresponding to the individual patient's most common requests.

Based on the foregoing and in accordance with embodiments contemplated herein, the following features of system 10, tablet computer 12, and the associated patient engagement software include the following:

The patient engagement software extends the functionality of a Nurse Call system by enabling iPad®-equipped (e.g., tablet-equipped) patients to interact with a hospital's Nurse Call system. The patient engagement software includes: system software that supplements the Nurse Call software environment, and the patent engagement application (aka "app") that runs on tablet 12, such as an iPad. Patients use the app to receive information and make non-urgent requests for care. The patient engagement app operates on hospital-supplied tablets 12, such as iPads, not on patient-supplied devices.

According to one example of a clinical scenario, an individual is admitted as an inpatient to an acute care hospital. Upon admission, they are oriented to their hospital room and to the patient engagement app on tablet 12, such as an Apple iPad. The patient can select one of many standard requests from any of several categories on the My Requests page. If the patient wants something to drink, for example, they can open the "I'm Thirsty" category and choose an option like "ginger ale" or "water." The patient engagement software provides immediate confirmation of submitted requests on tablet 12 and allows the patient to follow the status of the requests, from "Acceptance" to "Completion."

With known, standard Nurse Call systems, an attendant receives a non-specific request at the staff station (sometimes referred to as a master nurse station or master station) and then the attendant must contact both the patient and an appropriate caregiver. With the patient engagement software, however, incoming requests are specific, such as "water", "bathroom", or "pain", so the attendant's task is simplified. When combined with mobile communications functionality such as the Voalte Platform available from Hill-Rom Company, Inc, the patient engagement software can send specific requests to appropriate caregivers' phones without an attendant's attention.

In some embodiments of system 10, the following guidelines for use are applicable: the patient engagement software is for use in a healthcare environment only; the patient engagement software is for patients who are willing and able to use a tablet 12, such as an iPad, as an additional means of interaction with hospital staff, and who are willing and able to receive verbal and/or demonstrative instructions on its use; in addition to the patient engagement app, a standard bedside call button, such one on a siderail of a hospital bed or on a pillow speaker unit, must also be available to the patients; the patient engagement software is not intended to provide patient care or serve as a substitute for professional healthcare judgment; and the patient engagement software is not intended as a primary notification system for patients or staff.

In some embodiments, the following steps are undertaken in connection with assigning a tablet 12 (referred to as an "iPad" below, but other tablets are within the scope of the present disclosure) to a patient including obtaining an iPad from storage and assigning it to a specific patient: 1. From a Charging Station, select an iPad whose light is solid green (indicating it is fully charged) and carefully detach it from its charging cable; 2. Turn on the iPad by pressing and holding the Start button at the top-right corner; 3. Enter the unit-specific passcode (supplied by the Hospital IT department; 4. Verify again that the iPad is fully charged and if it is not, turn it off by pressing and holding the power button, put it in the return queue for proper charging and handling, and go back to Step 1; 5. Start the patient engagement app by touching a patient engagement icon; 6. On the Welcome screen or panel, press Get Started; 7. On a Care Team Sign In screen or panel, log in to the patient engagement app (using the caregiver's standard Hospital credentials) and if anything goes wrong, contact Hospital IT; 8. After a Patient Selection screen or panel presents a list of patients that a Medical Record System already considers to be in the caregiver's care, the caregiver taps the name of a patient in the list, or uses the search field to find a non-listed patient (to search for a non-listed patient, enter any fragment of the patient's name, medical record number, or birthdate in the form mm/dd/yyyy); 9. On the Assign Patient screen or panel, the caregiver confirms the choice by pressing Assign Patient; 10. The Welcome screen or panel appears and it is directed to the patient, not the caregiver, so the caregiver should not press the Let's Go button; and 11. Hand the iPad to the patient prior to introducing the patient to the patient engagement app.

The following is an example of a script that the caregiver may follow in connection with introducing the patient to the patient engagement app: "During your hospital stay, you are welcome to use the patient engagement app on this tablet to request non-emergency items—like when you're hungry or thirsty, or if you need help going to the bathroom, or if you just want a nurse. When you make a request on this iPad, a caregiver like me will get instant notification on their cellphone! See? I have a hospital phone in my pocket. There is also a health information library available for you to browse. I can bookmark some articles that are specific to your care, if you like." In some embodiments contemplated herein, the landing page of the health information library relates to Covid-19 (aka coronavirus 19 or SARS-CoV-2).

If after pointing to the Let's Get Started button a patient rejects the idea of using tablet 12 with the patient engagement app, the caregiver then undertakes the steps of un-assigning the iPad from the patient. However, if the patient agrees to use the tablet 12 with the patient engagement app, the following is an example of a script that the caregiver may follow: "Let me remind you of one important thing. If you have a true emergency, we still want you to press the bedside Call Button. OK?Here you go. If it's not self-explanatory, let me know. We don't like to use pesky chargers and cords in your room, so If the battery goes down, I'll bring you a fresh iPad. Please don't close the app to play with the iPad unless you know how to get back to the app. This app's icon is called Voalte Engage. Any questions? No, you may not take the iPad home. (Smile). See you later, and don't forget to use the bedside Call Button for true emergencies."

Under some limited circumstances, a caregiver may desire to re-assign an iPad from one patient to another. However, an iPad should not be received from one patient and immediately assigned to another. That is, a "used" iPad and accessories should always be returned and put in the return queue for proper handling. In the event an iPad is assigned to the wrong patient by the caregiver and the caregiver want to immediately transfer it to the right patient, the following steps are performed in some embodiments: 1. The caregiver presses the Care Team icon to access the Care Team Sign-In screen or panel; 2. The caregiver signs in with his or her standard credentials; 3. On the Care Team panel or screen, the caregiver touches (aka selects) the Assign a different patient button; 4. On the Assign a Different Patient panel or screen, the caregiver verifies that the named patient is the one to be un-assigned, and then the caregiver presses the Unassign & Select New Patient button; 5. On the Patient Selection panel or screen, the caregiver picks a listed patient (one that the hospital records system considers to be in the caregiver's care) or the caregiver uses the search tool to find a non-listed patient; 6. On the Assign Patient screen or panel, the caregiver verifies that the named patient is the one the caregiver intends to assign to the particular iPad, and then the caregiver touches the Assign Patient button; and 8. The caregiver introduces the patient engagement app to the patient and points to the Let's Get Started button.

After a patient is finished with the assigned tablet 12, the caregiver undertakes the following steps to unassign the iPad from the patient and return it for proper handling: 1. The caregiver presses the Care Team icon to access the Care Team Sign-In panel or screen; 2. The caregiver signs in with the caregiver's credentials; 3. On the Care Team Panel or screen, the caregiver touches, presses, or selects (these are used interchangeably herein), the unassign patient & return to welcome screen button; 4. On the Unassign & Return to Welcome screen or panel, the caregiver verifies that the named patient is the one that the caregiver wants to un-assign, then the caregiver touches the Unassign & Return To Welcome Screen button; 5. The caregiver turn the iPad off by pressing and holding the power button on the top right corner; and 6. The caregiver puts the iPad in the return queue for proper handling. Thus, a "used" iPad should not immediately be assigned to a new patient. In some embodiments of system 10, if a patient does not use the assigned iPad having the patient engagement app for 24 hours, the patient engagement software of system 10 automatically unassigns that iPad from that patient (even if the iPad's battery has run down).

Some additional notes about assigning and un-assigning tablets 12, such as iPads, in some embodiments of system 10 include the following: 1. On the Patient Selection Panel or screen, a caregiver can select a patient in two ways: (a) from a list of patients already in his or her care (per the Medical Records System), or (b) by searching by first and/or last name, by Medical Record Number (MRN), or by birthdate in the form mm/dd/yyyy; 2. A patient cannot be assigned to more than one iPad at a time; 3. Patients cannot share the patient engagement app on a single iPad; 4. Only one instance of the patient engagement app can run on an iPad at a time; 5. Whenever the patient engagment app is in patient mode, a caregiver can access the Care Team Sign-In panel or screen by pressing the Care Team icon and caregivers must sign in before taking any action on the Care Team Panel or screen; 6. If a caregiver gets locked out of the Care Team Panel or screen because of excessive login failures, they are locked out of all instances of the patient engagement app on all iPads because the unlocking protocol is controlled by the hospital's Active Directory policies (if a caregiver gets locked out, the caregiver should contact the Hospital's IT department).

After a patient request is made using the patient engagement app of an assigned tablet 12, there is a three-step process for receiving and responding to the patient's request, as follows:

1. Receive a request—Receive a request at the staff station and/or a mobile device of a caregiver. When the request is received at a staff station, the most appropriate caregiver must then be notified. When caregivers are equipped with mobile devices such a mobile phones, the request is automatically routed to the most appropriate caregiver.

2. Accept the request—At the staff station, route the request by standard procedure, or from the mobile device (e.g., mobile phone), notify the patient of receipt by "accepting" (e.g., selecting an "Accept" button or icon) the request, and optionally make voice contact with the patient's iPad.

3. Satisfy the request—Go to the room and press Cancel on the wall-mounted room station (to satisfy all requests from that patient), or let the Locating System (if available) cancel the request. If there are requests to multiple caregivers, the Locating System cancels only those requests that are directed to the caregiver that enters the room of the patient making the request.

After an iPad is assigned to a particular patient, the patient is able to begin using the patient engagement app. In this regard, immediately after the caregiver assigns an iPad and hands it to the patient, the patient sees the Welcome panel or screen at which point the patient undertakes the following steps: 1. On the Welcome to [Name of] Hospital panel or screen, the patient presses the Let's Go button: 2. On the Terms of Use screen or panel, the patient reads and presses the I Accept button; and 3. On the Welcome panel or screen, the patient presses ">" on a series of screens to see a several-page introduction; 4. On the last page of the introduction, the patient presses Start My Patient Engagement Experience; and 5. The patient sees a Today screen corresponding to selection of a Today tab (the Today tab corresponds to the first screen a patient sees after completing the introduction; see FIGS. 11-13 and the related discussion above with regard to the Today screens 112, 132, 132' associated with the Today tab 122).

On the Today screen, the following five fields are shown with the following information and/or buttons in the respective fields: 1. The patient's first name, time, date, and local weather; 2. Make a Request and Say a Request buttons (see Making a Request and Saying a Request below; the Make a Request button is similar to Make a Request button 130 of FIGS. 11-13 but is selected to start the voice input process of FIGS. 23-40 similar to voice button 214 of FIG. 22); 3. A list of in-progress requests, if any; 4. A link to re-view the introductory slideshow that appeared when the patient pressed the Let's Go button; and 5. Icon buttons that activate the three other Tabs (e.g., the My Stay icon 124, the My Request icon 126, and the Learn icon 128).

With regard to selection of My Stay tab or icon 124, the following seven fields are shown with the following information (similar to My Stay screens 140, 140' discussed above in connection with FIGS. 14 and 15): 1. My Information—The patient's full name, sex, and birthdate; 2. My Room—The patient's room number and unit name; 3. The Make a Request and Say a Request buttons (see Making a Request and Saying a Request); 4. My Care Team: The names of the Patient's caregivers; 5. Your Room &

Nearby—Information about the hospital, such as a hospital map and hospital cafeteria menu; 6. About the patient engagement app—Overview of the app (e.g., a re-play of the same slideshow that is available from the Today tab, frequently asked questions, Terms of Use, and also a re-play of the fine print the patient saw after pressing Let's Go), along with application settings; and 7. The icon buttons 122, 126, 128 that activate the three other Tabs to show the respective screens.

With regard to selection of My Requests tab or icon 126, the following five fields are shown with the following information (similar to My Requests screens 158, 158' discussed above in connection with FIGS. 16 and 17): 1. Quick access to the most frequently used request buttons—a subset of the choices that are available behind the Make a Request button; 2. The Make a Request button leads to a long list of specific request icons and the Say a Request leads to a voice-activated request tool (See Making a Request and Saying a Request). 3. In-Progress Requests—A summary of requests (whether submitted through Make a Request or Say a Request); 4. Completed Requests—A summary of requests already answered by a caregiver; and 5. Icon buttons 122, 124, 128 that activate the three other Tabs to show the respective screens.

As noted above, the Make A Request button 130 is available from the screens associated with the Today, My Stay, and My Requests tabs 122, 124, 126. Selection of the Make a Request button 130 leads to additional screens permitting the patient to specific requests by touching selectable icons. After selection of the Make a Request button 130, all available requests are categorized into a handful of Request Types. The patient touches one Request Type to expand the list of specific requests. For example, the patient picks a Request Type, like I'm Hungry, to see the specific requests in that category. Then the patient touches one (or more) specific requests, like Popsicle. An icon for each pending request appears at the bottom of the page or screen. If any pending request was chosen in error, the patient is able to cancel it by touching its name in the pending list at the bottom of the page. Once a specific patient request is submitted, however, it cannot be canceled. All Requests is a special category which contains an alphabetical set of all the requests in every other category. It should be noted that the set of Request Types and specific Requests are configurable per nursing unit by the IT department.

The Say a Request button (basically the same as voice button 214 discussed above) is also available on the screens associated the Today, My Stay, and My Requests tabs 122, 124, 126. In response to selection of the Say a Request button, an interactive, voice-controlled method of submitting requests results. A voice will say, for example, "How can I help you?" in response to selection of the Say a Request button.

The patient engagement app includes Learn tab 128, the selection of which offers health information from a commercial knowledgebase as noted above. The information is freely browsable by the patient and can also help a caregiver educate the patient as required by the patient's care plan. The patient (or caregiver) can search for articles and videos and, optionally, bookmark items for viewing (or re-viewing). Under the Learn tab 128, some embodiments of system 10 includes two methods of finding articles of interest as follows: 1. The Explore Topics method, and 2. The Start Searching method.

According to the Explore Topics Method, the following steps are undertaken by the user (patient or caregiver): 1. Pick a health category under the Explore Topics heading, like Allergies, Arthritis, or Flu (Note that even more categories are visible if the user scrolls to the left or right); 2. A set of related articles appears in a scrollable list and a keypad pops up for a more in-depth search of the scrollable list; 3. The user then does one of the following: (a) Scroll the list to find an article to read or save; (b) Narrow the set of listed articles by typing some keywords, then press the Search button on the keypad after which a narrowed set of topics appears and the user can then scroll the list again to find an article to read or save; 4. The user presses Cancel to stop the search; and 5. Note that the Learn page presents a link to every previously saved article.

According to the Start Searching Method the following steps are undertaken by the user (patient or caregiver): 1. Press the Start Searching button which causes a cursor to automatically appear in a Search field. (or, put the cursor in the Search field simply by touching the search field); 2. Type some keywords, then press the Search button on the keypad which results in a set of article titles appearing; 3. Access a specific article or video by touching its Title, and/or save one or more articles by touching one or more Save icons; 4. When the user finishes reading an article, the user presses Close in the top-left corner (if the user has tapped links within an article, the user is able to navigate forward and back by tapping the arrows); and 5. Note that Learn page presents a link to every previously saved article.

If the user wishes to delete an article from the set of saved articles (e.g., delete an article's bookmark), the following steps are undertaken: 1. On the opening page of the Learn tab, locates the set of bookmarks (if any exist) in the Saved Articles & Videos section; 2. Tap a bookmark's Saved symbol; and 3. To confirm the deletion, tap Remove and the bookmark disappears immediately.

Although certain illustrative embodiments have been described in detail above, variations and modifications exist within the scope and spirit of this disclosure as described and as defined in the following claims.

The invention claimed is:

1. A patient request system comprising
a tablet computer configured for entry of patient requests, the tablet computer being configured to display a first menu corresponding to basic request categories for a patient in response to selection of a make a request input on a predecessor screen of the tablet computer, the tablet computer being configured to display a second menu corresponding to specific patient requests that fall under the basic request category selected by the patient using the first menu,
a server configured to receive a specific patient request made by the patient,
a notification device configured to display the specific patient request to a caregiver, and
locating equipment operable to determine a location of the tablet computer in a healthcare facility and the first menu is altered based on the location, wherein if the tablet computer is determined to be located in a maternity ward, then a maternity option is included in the first menu, and if the tablet computer is determined not to be located in the maternity ward, then the maternity option is omitted from the first menu.

2. The patient request system of claim 1, wherein the locating equipment includes (i) wireless access points that are used to determine the location of the tablet computer based on received signal strengths of signals transmitted from the tablet computer, or (ii) a wireless locating tag attached to the tablet computer and locating receivers configured to communicate with the wireless locating tag.

3. The patient request system of claim 1,
wherein the tablet computer also is configured to display a plurality of selectable icons corresponding to most common requests for the healthcare facility, the plurality of selectable icons that are displayed on the tablet computer varying by unit of the healthcare facility in which the tablet computer is located, and
wherein the server is configured to monitor patient requests over time and automatically change the plurality of selectable icons appearing on the tablet computer to match the most common requests that are made in each of unit of the healthcare facility based on historical data for the healthcare facility.

4. The patient request system of claim 1, wherein the tablet computer is configured to display a list of specific patient requests made by the patient and a status of each specific patient request.

5. The patient request system of claim 1, wherein the tablet computer is configured to display a list of caregivers assigned to the patient.

6. The patient request system of claim 1, wherein the tablet computer is configured to display weather information based on a periodically received weather feed.

7. The patient request system of claim 1, wherein the basic categories included in first menu includes one or more of the following options: I'm thirsty, I'm hungry, I feel, help me with, services, room, bring me, or mother/baby.

8. The patient request system of claim 7, wherein in response to selection of the I'm thirsty option on the first menu, the specific patient requests appearing on the second menu include one or more of the following options: water, ice, juice, ginger ale, cola, diet cola, clear soda, clear diet soda, nutritional drink, or other drink.

9. The patient request system of claim 7, wherein in response to selection of the I'm hungry option on the first menu, the specific patient requests appearing on the second menu include one or more of the following options: crackers, meal, Jell-O, other snack, or popsicle.

10. The patient request system of claim 7, wherein in response to selection of the I feel option on the first menu, the specific patient requests appearing on the second menu include one or more of the following options: sick, pain, hot/cold, cold feet, can't sleep, or other need.

11. The patient request system of claim 7, wherein in response to selection of the help me with option on the first menu, the specific patient requests appearing on the second menu include one or more of the following options: get up/move, bandage problem, clothes/gown, blood sugar check, IV hurts, get a bath, bathroom, brush teeth, walk, collect bathroom specimen, or other problem.

12. The patient request system of claim 7, wherein in response to selection of the services option on the first menu, the specific patient requests appearing on the second menu include one or more of the following options: translator, chaplain/clergy, case manager/social worker, visitor information, or other service.

13. The patient request system of claim 7, wherein in response to selection of the room option on the first menu, the specific patient requests appearing on the second menu include one or more of the following options: I can't reach, room hot/cold, TV/remote control issue, adjust bed, machine is beeping, noisy, lights on/off, sheet change, spill, or other environmental.

14. The patient request system of claim 7, wherein in response to selection of the bring me option on the first menu, the specific patient requests appearing on the second menu include one or more of the following options: pen/paper, ice pack, pillow, blanket, or other need.

15. The patient request system of claim 7, wherein in response to selection of the mother/baby option on the first menu, the specific patient requests appearing on the second menu include one or more of the following options: pacifier, baby to/from nursery/bassinet, baby care, swaddling, breast-feeding, breast pump, pad, bottle/formula, diaper, baby wipes, skin time/kangaroo care, baby blanket, other need mother, or other need baby.

16. The patient request system of claim 1, wherein after the patient makes the specific patient request using the tablet computer, the tablet computer is operable to display a status of the specific patient request while the specific patient request is pending.

17. The patient request system of claim 16, wherein the status includes fields that are highlighted to indicate that the specific patient request has been submitted, that the specific patient request has been accepted by a caregiver, and that the specific patient request has been completed.

18. The patient request system of claim 1, wherein the tablet computer is configured to permit the patient to make specific patient requests by voice.

19. The patient request system of claim 1, wherein the tablet computer is configured to permit the patient to make and receive phone calls and video calls.

20. The patient request system of claim 1, wherein the tablet computer is configured to display each of the following: visitor hours, parking information, a cafeteria menu, hospital activities, and a TV channel list.

\* \* \* \* \*